United States Patent
Takaku et al.

(10) Patent No.: US 9,412,963 B2
(45) Date of Patent: Aug. 9, 2016

(54) ORGANIC ELECTROLUMINESCENT ELEMENT, MATERIAL FOR ORGANIC ELECTROLUMINESCENT ELEMENT, AND LIGHT EMITTING DEVICE, DISPLAY DEVICE AND ILLUMINATION DEVICE EACH USING THE ELEMENT

(71) Applicant: UDC Ireland Limited, Dublin (IE)

(72) Inventors: Koji Takaku, Kanagawa (JP); Yasunori Yonekuta, Kanagawa (JP); Katsuyuki Youfu, Kanagawa (JP); Wataru Sotoyama, Kanagawa (JP); Tianhua Ouyang, Kanagawa (JP); Tetsu Kitamura, Kanagawa (JP); Toru Watanabe, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 816 days.

(21) Appl. No.: 13/677,759

(22) Filed: Nov. 15, 2012

(65) Prior Publication Data

US 2013/0119359 A1 May 16, 2013

(30) Foreign Application Priority Data

Nov. 16, 2011 (JP) .................. 2011-250945

(51) Int. Cl.
*H01L 51/50* (2006.01)
*C07D 495/04* (2006.01)
(Continued)

(52) U.S. Cl.
CPC .......... *H01L 51/5092* (2013.01); *C07C 211/54* (2013.01); *C07C 211/58* (2013.01);
(Continued)

(58) Field of Classification Search
CPC ............ C07C 2103/50; C07C 2103/54; C07C 211/54; C07C 211/58; C07C 211/61; C07D 401/10; C07D 407/10; C07D 493/04; C07D 493/06; C07D 495/04; C07F 7/0814; C07F 7/10; C09K 11/06; C09K 2211/1011; H01L 2251/308; H01L 51/0058; H01L 51/0061; H01L 51/0072; H01L 51/0073; H01L 51/5012; H01L 51/5092; H05B 33/14
See application file for complete search history.

(56) References Cited

U.S. PATENT DOCUMENTS

| | | | |
|---|---|---|---|
| 2008/0213624 A1* | 9/2008 | Lecloux | C09K 11/06 428/691 |
| 2010/0244665 A1* | 9/2010 | Herron | C07C 13/66 313/504 |

(Continued)

FOREIGN PATENT DOCUMENTS

| | | |
|---|---|---|
| JP | 2001-167883 A * | 6/2001 |
| JP | 200519219 | 1/2005 |
| JP | 2009514812 | 4/2009 |

OTHER PUBLICATIONS

Machine translation for JP 2001-167883 (publication date: Jun. 2001).*

*Primary Examiner* — Dawn Garrett
(74) *Attorney, Agent, or Firm* — Riverside Law LLP

(57) ABSTRACT

The disclosure relates to organic electroluminescent elements, materials for use in the elements, and devices using the elements, which include a compound represented by the following General Formula (1):

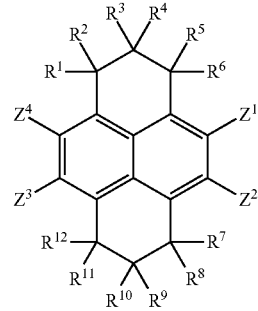

General Formula (1)

where $R^1$ to $R^{12}$ each independently represents a hydrogen atom or a substituent and which may be bound to each other to form a non-aromatic ring, where $Z^1$ to $Z^4$ each independently represents a hydrogen atom or a substituent, and where $Z^1$ and $Z^2$, and $Z^3$ and $Z^4$ may be bound to each other to form a ring.

18 Claims, 1 Drawing Sheet

(51) Int. Cl.

| | |
|---|---|
| *C07D 407/10* | (2006.01) |
| *C07C 211/61* | (2006.01) |
| *C07D 401/10* | (2006.01) |
| *C07D 493/04* | (2006.01) |
| *C07F 7/10* | (2006.01) |
| *C07D 493/06* | (2006.01) |
| *C07C 211/54* | (2006.01) |
| *C07C 211/58* | (2006.01) |
| *C09K 11/06* | (2006.01) |
| *H05B 33/14* | (2006.01) |
| *C07F 7/08* | (2006.01) |
| *H01L 51/00* | (2006.01) |

(52) U.S. Cl.
CPC ............ *C07C211/61* (2013.01); *C07D 401/10* (2013.01); *C07D 407/10* (2013.01); *C07D 493/04* (2013.01); *C07D 493/06* (2013.01); *C07D 495/04* (2013.01); *C07F 7/0814* (2013.01); *C07F 7/10* (2013.01); *C09K 11/06* (2013.01); *H01L 51/0061* (2013.01); *H01L 51/0073* (2013.01); *H05B 33/14* (2013.01); *C07C 2103/50* (2013.01); *C07C 2103/54* (2013.01); *C09K 2211/1011* (2013.01); *H01L 51/0058* (2013.01); *H01L 51/0072* (2013.01); *H01L 51/5012* (2013.01); *H01L 2251/308* (2013.01)

(56) References Cited

U.S. PATENT DOCUMENTS

| | | | |
|---|---|---|---|
| 2012/0211734 A1* | 8/2012 | Herron | C07C 13/66 257/40 |
| 2013/0126835 A1* | 5/2013 | Takaku | H01L 51/0058 257/40 |
| 2015/0076462 A1* | 3/2015 | Kitamura | C07D 307/77 257/40 |

* cited by examiner

ORGANIC ELECTROLUMINESCENT ELEMENT, MATERIAL FOR ORGANIC ELECTROLUMINESCENT ELEMENT, AND LIGHT EMITTING DEVICE, DISPLAY DEVICE AND ILLUMINATION DEVICE EACH USING THE ELEMENT

CROSS-REFERENCE TO RELATED APPLICATIONS

This application claims the benefit of priority to Japanese Patent Application No. 2011-250945, filed Nov. 16, 2011, which is incorporated herein by reference in its entirety.

FIELD OF THE INVENTION

The present invention relates to an organic electroluminescent element and a material for an organic electroluminescent element which can be used in the same. The present invention also relates to a light emitting device, a display device, or an illumination device each using the organic electroluminescent element.

DESCRIPTION OF THE RELATED ART

Since organic electroluminescent elements (which may hereinafter also be referred to as "elements" or "organic EL elements") are capable of high-luminance light emitting using low voltage driving, they have been actively researched and developed. The organic electroluminescent elements have a pair of electrodes and an organic layer between the pair of electrodes, and utilize, for light emitting, energy of the exciton generated as a result of recombination of the electron injected from the cathode and the hole injected from the anode in the organic layer. The organic electroluminescent elements can provide elements having diverse light emitting wavelengths, and since they have a high response speed and are relatively thin and light-weight, it is expected that they can be employed in a wide range of applications. Among these, it is important to develop an organic electroluminescent element having high color purity and luminous efficiency in light of the applications in full-color displays and the like, and the outcomes have been reported of various research and development studies up to now.

For example, Patent Document 1 describes that when an oligonaphthalene compound having the number of naphthalenes of from 4 to 6 is included in a light emitting region layer, it becomes possible to reveal high amorphous properties, light emission with high efficiency in a blue color region, and a longer life.

In addition, Patent Document 2 describes that a binaphthalene derivative is included in any one of a hole injecting layer, a hole transporting layer, a light emitting layer, and an electron transporting layer and also describes that in particular, when a binaphthalene derivative is included in a transporting layer, it becomes possible to achieve light emission of from blue to red colors and to reveal a longer life at a low voltage.

RELATED ART DOCUMENT

Patent Document

Patent Document 1: JP-A-2005-19219
Patent Document 2: JP-T-2009-514812

SUMMARY OF THE INVENTION

However, according to investigations made by the present inventors, it has become clear that in the above-described Patent Document 1, an emission maximum is present on the long wavelength side of from 460 to 480 nm, and a high blue color purity cannot be realized. In addition, it has also become clear that when an organic electroluminescent element in which an oligonaphthalene compound is incorporated into a light emitting region layer is driven, the chromaticity at the time of luminance modulation changes.

An object of the present invention is to solve the above-described problems. That is, an object of the present invention is to provide an organic electroluminescent element capable of realizing a high blue color purity, enhancing the luminous efficiency, and improving a reduction of the chromaticity change during driving of the organic electroluminescent element.

Then, for the purpose of providing an organic electroluminescent element capable of realizing a high blue color purity, enhancing the luminous efficiency, and improving a reduction of the chromaticity change during driving of the organic electroluminescent element, the present inventors made extensive and intensive investigations.

Though it could be expected that by further linking the binaphthalene derivative described in Patent Document 2 with from 2 to 3 naphthalene rings, a high blue color purity is realized, it may also be expected that there is involved such a problem that the crystallinity increases.

Under such circumstances, the present inventors have found that by using a compound having, as a linkage center, a hexahydropyrene ring in which the 1-position and the 8-position, and the 4-position and the 6-position, of the naphthalene ring are bound to each other via an alkylene, respectively, it becomes possible to make both high amorphous properties and blue purity compatible with each other, thereby enabling one to give a sufficient performance as a light emitting material. In particular, the reduction of the chromaticity change after driving deterioration is an effect of a different nature which has not been known in the known documents.

That is, it has been found that the above-described problems can be solved by using a compound having, as a linkage center, a hexahydropyrene ring having a specified structure, leading to accomplishment of the present invention as described below.

Measures for solving the above-described problems are as follows.

[1] An organic electroluminescent element comprising:
a substrate;
a pair of electrodes including an anode and a cathode, disposed on the substrate; and
at least one organic layer including a light emitting layer, disposed between the electrodes, wherein
the organic layer includes a compound represented by the following general formula (1):

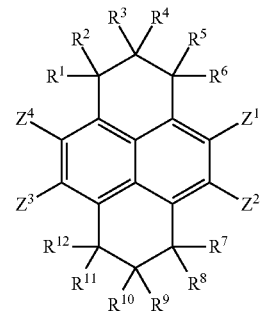

General Formula (1)

(In the general formula (1), $R^1$ to $R^{12}$ each independently represent a hydrogen atom or a substituent, and these may be bound to each other to form a ring, provided that the ring obtained by these being bonded is not an aromatic ring; $Z^1$ to $Z^4$ each independently represent a hydrogen atom or a substituent; and $Z^1$ and $Z^2$, and $Z^3$ and $Z^4$, may be bound to each other to form a ring.)

[2] The organic electroluminescent element as set forth in [1], wherein, in the general formula (1), $R^1$ to $R^{12}$ are preferably selected from a hydrogen atom, an alkyl group, an aryl group, a heteroaryl group, —$NY^1Y^2$, —$OY^3$, —$SY^4$ ($Y^1$ to $Y^4$ each independently represent an alkyl group, an aryl group, or a heteroaryl group, and these may further have substituents), a halogen atom, and a silyl group.

[3] The organic electroluminescent element as set forth in [1] or [2], wherein the compound represented by the general formula (1) is preferably a compound represented by the following general formula (2):

General Formula (2)

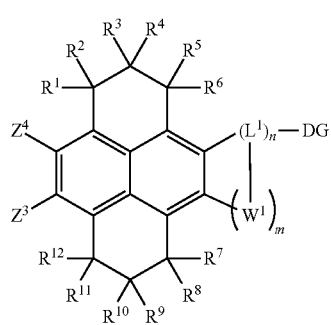

(In the general formula (2), $R^1$ to $R^{12}$ each independently represent a hydrogen atom or a substituent, and these may be bound to each other to form a ring, provided that the ring obtained by these being bonded is not an aromatic ring, $L^1$ represents a divalent or higher linking group, $W^1$ represents O, S, $CY^8Y^9$, or $NY^6$ ($Y^6$, $Y^8$, and $Y^9$ each independently represent an alkyl group, a silyl group, an aryl group, or a heteroaryl group, and these may further have substituents); $Z^3$ and $Z^4$ each independently represent a hydrogen atom or a substituent; $L^1$ and $W^1$, and $Z^3$ and $Z^4$, may be bound to each other to form a ring; DG represents a donor group; n represents an integer of 1 or 2; m represents 0 or 1; and when m is 0, then $L^1$ and $W^1$ are not bound to each other.)

[4] The organic electroluminescent element as set forth in [3], wherein the compound represented by the general formula (2) is preferably a compound represented by the following general formula (3):

General Formula (3)

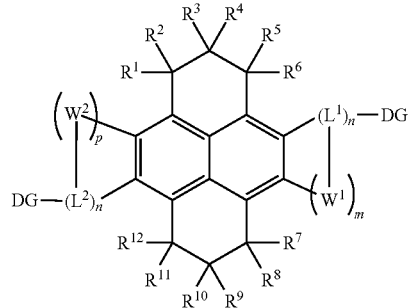

(In the general formula (3), $R^1$ to $R^{12}$ each independently represent a hydrogen atom or a substituent, and these may be bound to each other to form a ring, provided that the ring obtained by these being bonded is not an aromatic ring; $L^1$ and $L^2$ each independently represent a divalent or higher linking group; $W^1$ and $W^2$ each independently represent O, S, $CY^8Y^9$, or $NY^6$ ($Y^6$, $Y^8$, and $Y^9$ each independently represent an alkyl group, a silyl group, an aryl group, or a heteroaryl group, and these may further have substituents); $L^1$ and $W^1$, and $L^2$ and $W^2$, may be bound to each other to form a ring; DG represents a donor group; n represents an integer of 1 or 2; m and p represent an integer of 0 or 1; and when m or p is 0, then $L^1$ and $W^1$, and $L^2$ and $W^2$, are not bonded to each other.)

[5] The organic electroluminescent element as set forth in [3] or [4], wherein, in the general formulae (2) and (3), the donor group preferably represents —$NY^1Y^2$, —$OY^3$, or $SY^4$ ($Y^1$ to $Y^4$ each independently represent an alkyl group, an aryl group, or a heteroaryl group, and these may further have substituents), or is represented by the following general formula (A):

General Formula (A)

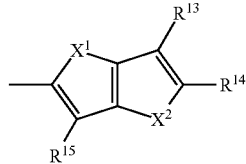

(In the general formula (A), $X^1$ and $X^2$ each independently represent O, S, or $NY^5$; and $R^{13}$ to $R^{15}$ each independently represent a hydrogen atom, an alkyl group, a silyl group, an aryl group, a heteroaryl group, —$NY^1Y^2$, —$OY^3$, or —$SY^4$ ($Y^1$ to $Y^5$ each independently represent an alkyl group, an aryl group, or a heteroaryl group), and all of these may further have substituents.)

[6] The organic electroluminescent element as set forth in any one of [3] to [5], wherein, in the general formulae (2) and (3), $L^1$ and $L^2$ each independently represent an arylene group or a heteroarylene group.

[7] The organic electroluminescent element as set forth in any one of [3] to [6], wherein, in the general formulae (2) and (3), $L^1$ and $L^2$ are each independently preferably represented by any one of following general formulae (4) to (7) (provided that a substituent with a Hammett substituent constant $\sigma_p$ value of 0.1 or more is not included in the linking group represented by the following general formulae (4) to (7)):

General Formula (4)

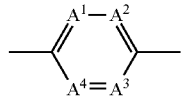

(In the general formula (4), $A^1$ to $A^4$ each independently represent $CY^7$ or N; $A^1$ and $A^2$ may be fused to form an aromatic ring; $Y^7$ represents a hydrogen atom, an alkyl group, an aryl group, or a heteroaryl group, and these may further have substituents; $W^1$ is bound to $A^4$ when m in the general formula (2) is 1; and $W^1$ and $W^2$ are bound to $A^4$ when m and p in the general formula (3) each independently represent 1.)

General Formula (5)

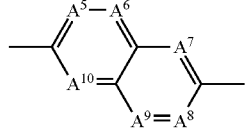

(In the general formula (5), $A^5$ to $A^{10}$ each independently represent $CY^7$ or N; $Y^7$ represents a hydrogen atom, an alkyl group, an aryl group, or a heteroaryl group, and these may further have substituents; $W^1$ is bound to $A^5$ or $A^{10}$ when m in the general formula (2) is 1; and $W^1$ and $W^2$ are bound to $A^5$ or $A^{10}$ when m and p in the general formula (3) each independently represent 1.)

General Formula (6)

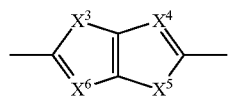

(In the general formula (6), $X^3$ and $X^5$ each independently represent O, S, or $NY^6$; $X^4$ and $X^6$ each independently represent $CY^7$ or N; and $Y^6$ and $Y^7$ each independently represent a hydrogen atom, an alkyl group, an aryl group, or a heteroaryl group, and these may further have substituents. However, m and p in the general formula (2) or (3) are 0.)

General Formula (7)

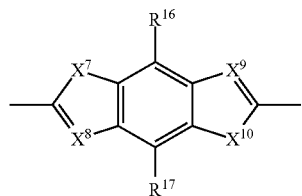

(In the general formula (7), $X^7$ and $X^{10}$ each independently represent O, S or $NY^6$; $X^8$ and $X^9$ each independently represent $CY^7$ or N; $Y^6$ and $Y^7$ each independently represent a hydrogen atom, an alkyl group, an aryl group, or a heteroaryl group, and these may further have substituents; and $R^{16}$ and $R^{17}$ each independently represent a hydrogen atom, a fluorine atom, an alkyl group, a silyl group, an aryl group, a heteroaryl group, $-NY^1Y^2$, $-OY^3$, or $-SY^4$ ($Y^1$ to $Y^4$ each independently represent an alkyl group, an aryl group, or a heteroaryl group), and these may further have substituents. However, m and p in the general formula (2) or (3) are 0.)

[8] The organic electroluminescent element as set forth in any one of [3] to [7], wherein the compound represented by the general formula (2) is preferably a compound represented by any one of following general formulae (8) to (11):

General Formula (8)

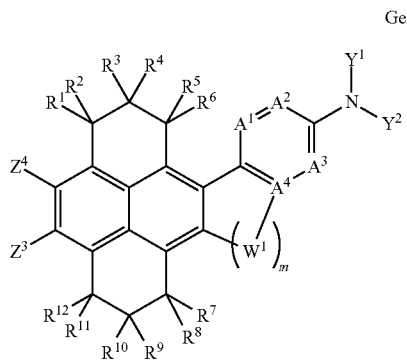

(In the general formula (8), $R^1$ to $R^{12}$ each independently represent a hydrogen atom or a substituent, and these may be bound to each other to form a ring, provided that the ring obtained by these being bonded is not an aromatic ring; $A^1$ to $A^4$ each independently represent $CY^7$ or N; $A^1$ and $A^2$ may be fused to form an aromatic ring; $Y^7$ represents a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; $W^1$ represents O, S, $CY^8Y^9$, or $NY^6$ ($Y^6$, $Y^8$, and $Y^9$ each independently represent an alkyl group, a silyl group, an aryl group, or a heteroaryl group, and these may further have substituents); $Z^3$ and $Z^4$ each independently represent a hydrogen atom or a substituent; $A^4$ and $W^1$, and $Z^3$ and $Z^4$, may be bound to each other to form a ring; m represents 0 or 1; and $A^4$ and $W^1$ are not bound to each other when m is 0.)

General Formula (9)

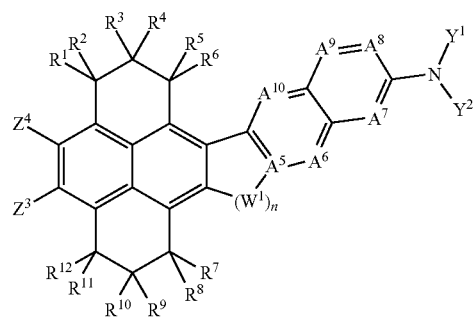

(In the general formula (9), $R^1$ to $R^{12}$ each independently represent a hydrogen atom or a substituent and may be bound to each other to form a ring to form a ring, provided that the ring obtained by these being bonded is not an aromatic ring; $A^5$ to $A^{10}$ each independently represent $CY^7$ or N; $Y^7$ represents a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; $W^1$ represents O, S, $CY^8Y^9$, or $NY^6$ ($Y^6$, $Y^8$, and $Y^9$ each independently represent an alkyl group, a silyl group, an aryl group, or a heteroaryl group, and these may further have substituents); $Z^3$ and $Z^4$ each independently represent a hydrogen atom or a substituent; $A^5$ and $W^1$ and $Z^3$ and $Z^4$, may be bound to each other to form a ring; m represents 0 or 1; and $A^5$ and $W^1$ are not bound to each other when m is 0.)

General Formula (10)

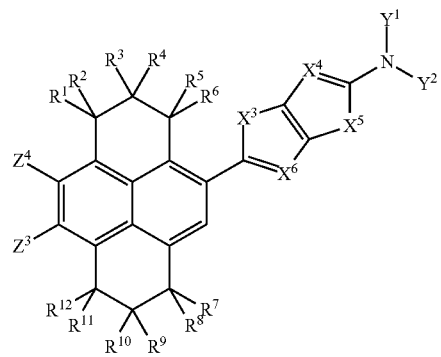

(In the general formula (10), $R^1$ to $R^{12}$ each independently represent a hydrogen atom or a substituent and may be bound to each other to form a ring, provided that the ring obtained by these being bonded is not an aromatic ring; $X^3$ and $X^5$ each independently represent O, S, or $NY^6$; $X^4$ and $X^6$ each independently represent $CY^7$ or N; $Y^6$ and $Y^7$ each independently represent a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; $Z^2$ to $Z^4$ each independently represent a hydrogen atom or a substituent; and $Z^3$ and $Z^4$ may be bound to each other to form a ring.)

General Formula (11)

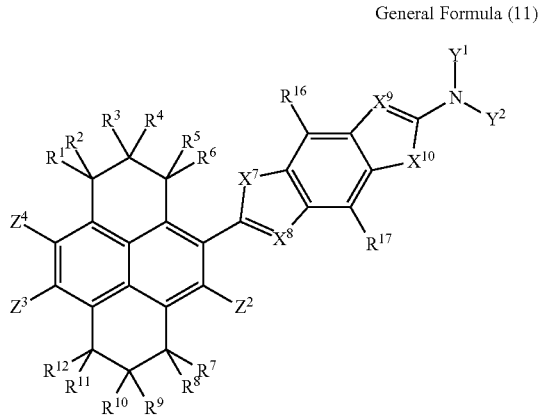

(In the general formula (11), $R^1$ to $R^{12}$ each independently represent a hydrogen atom or a substituent and may be bound to each other to form a ring, provided that the ring obtained by these being bonded is not an aromatic ring; $X^7$ and $X^{10}$ each independently represent O, S, or $NY^6$; $X^8$ and $X^9$ each independently represent $CY^7$ or N; $Y^6$ and $Y^7$ each independently represent a hydrogen atom, an alkyl group, an aryl group, or a heteroaryl group, and these may further have substituents; $R^{16}$ and $R^{17}$ each independently represent a hydrogen atom, a fluorine atom, an alkyl group, a silyl group, an aryl group, a heteroaryl group, $-NY^1Y^2$, $-OY^3$, or $-SY^4$ ($Y^1$ to $Y^4$ each independently represent an alkyl group, an aryl group, or a heteroaryl group), and these may further have substituents; $Y^1$ and $Y^2$ each independently represent an alkyl group, an aryl group, or a heteroaryl group, and these may further have substituents and may be bound to each other to form a ring; $Z^2$ to $Z^4$ each independently represent a hydrogen atom or a substituent; and $Z^3$ and $Z^4$ may be bound to each other to form a ring.)

[9] The organic electroluminescent element as set forth in [8], wherein the compound represented by the general formula (8) is preferably a compound represented by the following general formula (12):

General Formula (12)

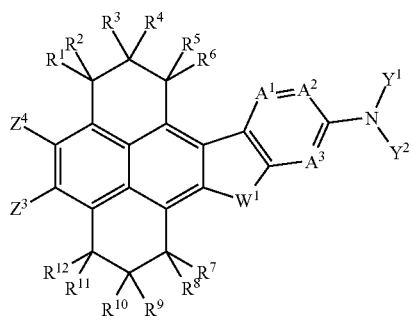

(In the general formula (12), $R^1$ to $R^{12}$ each independently represent a hydrogen atom or a substituent, and these may be bound to each other to form a ring, provided that the ring obtained by these being bonded is not an aromatic ring; $A^1$ to $A^4$ each independently represent $CY^7$ or N; $A^1$ and $A^2$ may be fused to form an aromatic ring; $Y^7$ represents a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; $W^1$ represents O, S, $CY^8Y^9$, or $NY^6$ ($Y^6$, $Y^8$, and $Y^9$ each independently represent an alkyl group, a silyl group, an aryl group, or a heteroaryl group, and these may further have substituents); $Z^3$ and $Z^4$ each independently represent a hydrogen atom or a substituent; and $Z^3$ and $Z^4$ may be bound to each other to form a ring.)

[10] The organic electroluminescent element as set forth in [8], wherein the compound represented by the general formula (9) is preferably a compound represented by the following general formula (13):

General Formula (13)

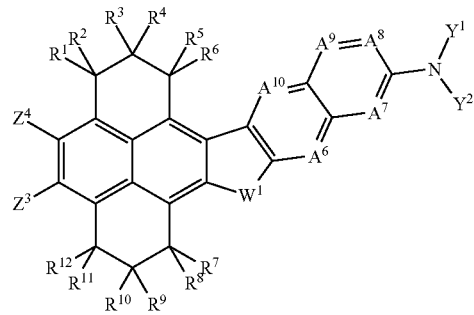

(In the general formula (13), $R^1$ to $R^{12}$ each independently represent a hydrogen atom or a substituent and may be bound to each other to form a ring to form a ring, provided that the ring obtained by these being bonded is not an aromatic ring; $A^5$ to $A^{10}$ each independently represent $CY^7$ or N; $Y^7$ represents a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; $W^1$ represents O, S, $CY^8Y^9$, or $NY^6$ ($Y^6$, $Y^8$, and $Y^9$ each independently represent an alkyl group, a silyl group, an aryl group, or a heteroaryl group, and these may further have substituents); $Z^3$ and $Z^4$ each independently represent a hydrogen atom or a substituent; and $Z^3$ and $Z^4$ may be bound to each other to form a ring.)

[11] The organic electroluminescent element as set forth in [8], wherein the compound represented by the general formula (2) is preferably a compound represented by any one of following general formulae (8') to (11'):

General Formula (8')

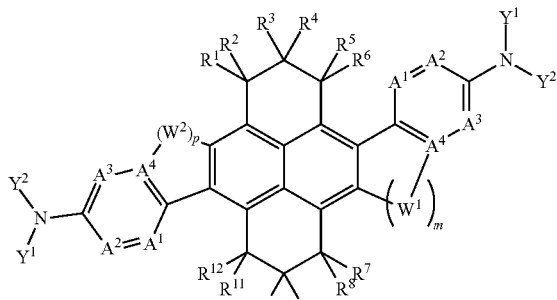

(In the general formula (8'), $R^1$ to $R^{12}$ each independently represent a hydrogen atom or a substituent and may be bound to each other to form a ring to form a ring, provided that the ring obtained by these being bonded is not an aromatic ring; $A^1$ to $A^4$ each independently represent $CY^7$ or N; $A^1$ and $A^2$ may be fused to form an aromatic ring; $Y^7$ represents a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; $W^1$ and $W^2$ each independently represent O, S, $CY^8Y^9$, or $NY^6$ ($Y^6$, $Y^8$, and $Y^9$ each independently represent an alkyl group, a silyl group, an aryl group, or a heteroaryl group, and these may further have substituents); m represents 0 or 1; $A^4$ and $W^1$ are not bound to each other when m is 0; p represents 0 or 1; and $A^4$ and $W^2$ are not bound to each other when p is 0.)

General Formula (10')

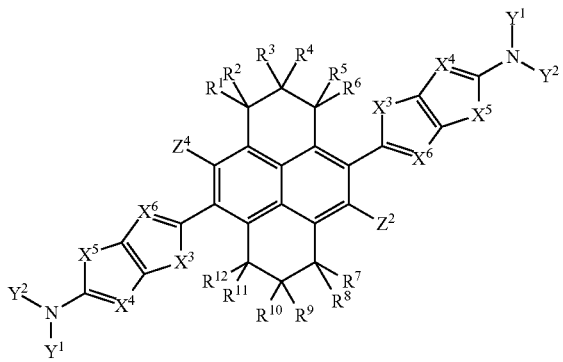

(In the general formula (10'), $R^1$ to $R^{12}$ each independently represent a hydrogen atom or a substituent and may be bound to each other to form a ring to form a ring, provided that the ring obtained by these being bonded is not an aromatic ring; $X^3$ and $X^5$ each independently represent O, S, or $NY^6$; $X^4$ and $X^6$ each independently represent $CY^7$ or N; $Y^6$ and $Y^7$ each independently represent a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; and $Z^2$ and $Z^4$ each independently represent a hydrogen atom or a substituent.)

General Formula (9')

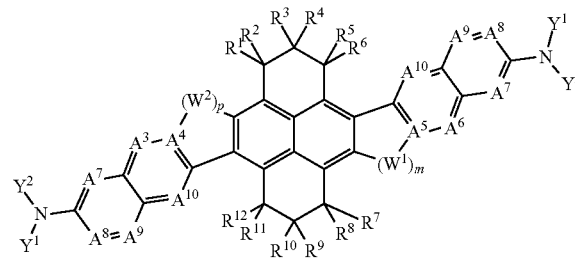

(In the general formula (9'), $R^1$ to $R^{12}$ each independently represent a hydrogen atom or a substituent and may be bound to each other to form a ring to form a ring, provided that the ring obtained by these being bonded is not an aromatic ring; $A^5$ to $A^{10}$ each independently represent $CY^7$ or N; $Y^7$ represents a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; $W^1$ and $W^2$ each independently represent O, S, $CY^8Y^9$, or $NY^6$ ($Y^6$, $Y^8$, and $Y^9$ each independently represent an alkyl group, a silyl group, an aryl group, or a heteroaryl group, and these may further have substituents); m represents 0 or 1; $A^5$ and $W^1$ are not bound to each other when m is 0; p represents 0 or 1; and $A^5$ and $W^2$ are not bound to each other when p is 0.)

General Formula (11')

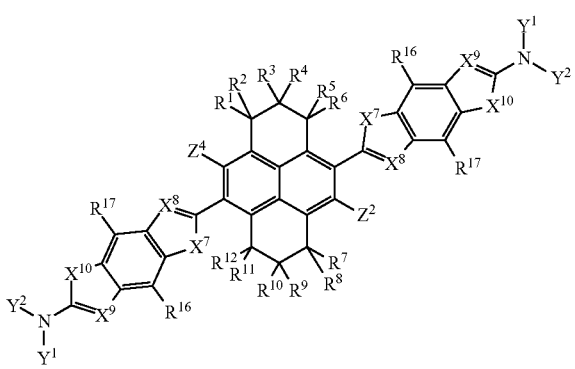

(In the general formula (11'), $R^1$ to $R^{12}$ each independently represent a hydrogen atom or a substituent and may be bound to each other to form a ring to form a ring, provided that the ring obtained by these being bonded is not an aromatic ring; $X^7$ and $X^{10}$ each independently represent O, S, or $NY^6$; $X^8$ and $X^9$ each independently represent $CY^7$ or N; $Y^6$ and $Y^7$ each independently represent a hydrogen atom, an alkyl group, an aryl group, or a heteroaryl group, and these may further have substituents; $R^{16}$ and $R^{17}$ each independently represent a hydrogen atom, a fluorine atom, an alkyl group, a silyl group, an aryl group, a heteroaryl group, —$NY^1Y^2$, —$OY^3$, or —$SY^4$ ($Y^1$ to $Y^4$ each independently represent an alkyl group, an aryl group, or a heteroaryl group), and these may further have substituents; $Y^1$ to $Y^2$ each independently represent an alkyl group, an aryl group, or a heteroaryl group, and these may further have substituents and may be bound to each other to form a ring; and $Z^2$ and $Z^4$ each independently represent a hydrogen atom or a substituent.)

[12] The organic electroluminescent element as set forth in [11], wherein the compound represented by the general formula (8') is preferably a compound represented by the following general formula (14):

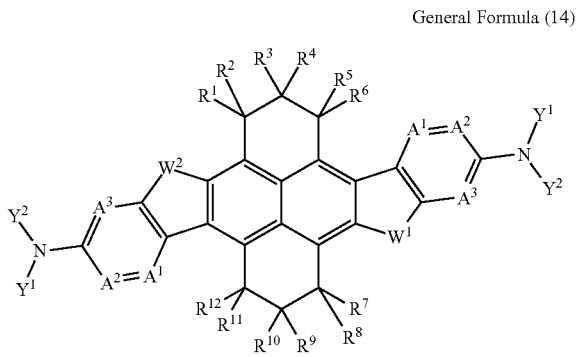

General Formula (14)

(In the general formula (14), $R^1$ to $R^{12}$ each independently represent a hydrogen atom or a substituent and may be bound to each other to form a ring to form a ring, provided that the ring obtained by these being bonded is not an aromatic ring; $A^1$ to $A^3$ each independently represent $CY^7$ or N; $A^1$ and $A^2$ may be fused to form an aromatic ring; $Y^7$ represents a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; and $W^1$ and $W^2$ each independently represent O, S, $CY^8Y^9$, or $NY^6$ ($Y^6$, $Y^8$, and $Y^9$ each independently represent an alkyl group, a silyl group, an aryl group, or a heteroaryl group, and these may further have substituents).)

[13] The organic electroluminescent element as set forth in [11], wherein the compound represented by the general formula (9') is preferably a compound represented by the following general formula (15):

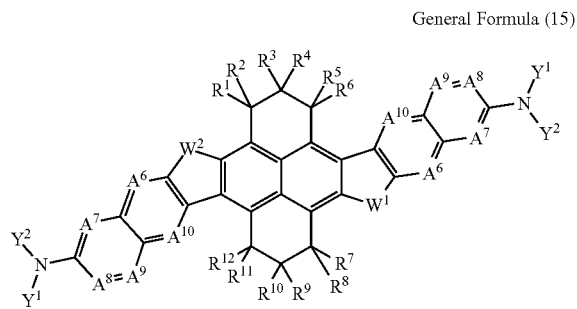

General Formula (15)

(In the general formula (15), $R^1$ to $R^{12}$ each independently represent a hydrogen atom or a substituent and may be bound to each other to form a ring to form a ring, provided that the ring obtained by these being bonded is not an aromatic ring; $A^5$ to $A^{10}$ each independently represent $CY^7$ or N; $Y^7$ represents a hydrogen atom, an alkyl group, an aryl group, or a heteroaryl group, and these may further have substituents; $Y^1$ and $Y^2$ each independently represent an alkyl group, an aryl group, or a heteroaryl group, and these may further have substituents and may be bound to each other to form a ring; and $W^1$ and $W^2$ each independently represent O, S, $CY^8Y^9$, or $NY^6$ ($Y^6$, $Y^8$, and $Y^9$ each independently represent an alkyl group, a silyl group, an aryl group, or a heteroaryl group, and these may further have substituents).)

[14] The organic electroluminescent element as set forth in any one of [1] to [13], wherein the light emitting layer preferably includes an anthracene-based host material.

[15] The organic electroluminescent element as set forth in any one of [1] to [14], wherein the light emitting layer is preferably formed by a vacuum deposition process.

[16] The organic electroluminescent element as set forth in any one of [1] to [15], wherein the light emitting layer is preferably formed by a wet process.

[17] A light emitting device using the organic electroluminescent element as set forth in anyone of [1] to [16].

[18] A display device using the organic electroluminescent element as set forth in any one of [1] to [16].

[19] An illumination device using the organic electroluminescent element as set forth in any one of [1] to [16].

[20] A material for an organic electroluminescent element represented by the following general formula (1):

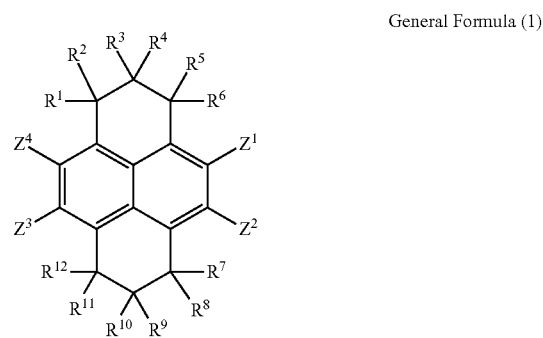

General Formula (1)

(In the general formula (1), $R^1$ to $R^{12}$ each independently represent a hydrogen atom or a substituent and may be bound to each other to form a ring to form a ring, provided that the ring obtained by these being bonded is not an aromatic ring; $Z^1$ to $Z^4$ each independently represent a hydrogen atom or a substituent; and $Z^1$ and $Z^2$, and $Z^3$ and $Z^4$, may be bound to each other to form a ring.)

According to the present invention, it is possible to provide an organic electroluminescent element capable of realizing a high blue color purity, enhancing the luminous efficiency, and improving a reduction of the chromaticity change during driving of the organic electroluminescent element.

DETAILED DESCRIPTION OF THE INVENTION

Figure 1:
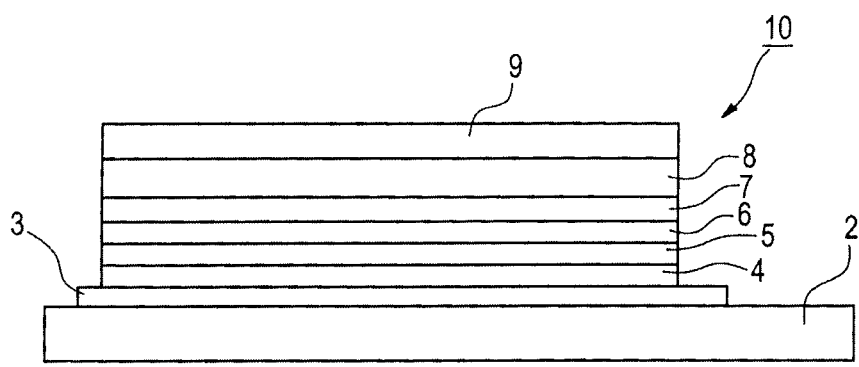
FIG. 1 is a schematic view showing one example of a configuration of the organic electroluminescent element according to the present invention.

The details of the present invention are hereunder described. The description of the configuration requirements below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

[Organic Electroluminescent Element]

The organic electroluminescent element according to the present invention comprises a substrate; a pair of electrodes including an anode and a cathode, disposed on the substrate; and at least one organic layer including a light emitting layer, disposed between the electrodes, wherein the organic layer includes a compound represented by the foregoing general formula (1).

In the organic electroluminescent element according to the present invention, it is preferable that the compound represented by the general formula (1) is used as a light emitting material.

Here, in the case of driving the organic electroluminescent element, an applied voltage is different between at the time of low luminance and at the time of high luminance. In an organic electroluminescent element using an organic layer, it is general that the voltage dependency of a rate for transporting electrons and the voltage dependency of a rate for transporting holes are different from each other. Accordingly, it may be considered that when the applied voltage is different, a relative difference between the transporting rate of electrons and the transporting rate of holes changes, so that a position at which recombination occurs within the light emitting layer is different. Since the organic electroluminescent device is a laminate of plural organic layers, and metal electrodes are used, if a light emitting position is different, then an optical interference effect is also different. Here, when the element thickness is one used in usual organic EL elements, it may be considered that if a blue luminous spectrum is broad, or a peak other than a main peak is present, the components on the long wavelength side are strengthened, and the chromaticity does not become constant.

On the other hand, according to the organic electroluminescent element using the compound represented by the general formula (1) as a light emitting material, light emission with a high-purity blue color purity is obtained as compared with those using a conventionally known analogous compound. Not wishing to be restricted to any theory, there is exemplified a reason that since the association is inhibited, or a structural change in the excited state is small, the spectrum is sharp. In addition, for example, in view of the fact that the spectrum shape is sharp (a shape in which the half-value width is narrow, and a peak other than the main peak is small), it has been noted that the chromaticity change between at the time of driving at a low luminance and at the time of driving at a high luminance is extremely small.

In addition, shortening of the light emitting wavelength by a substituent is synonymous with instabilization of the compound, and in many cases, a lowering of the durability by cleavage of the substituent or the like is brought. Accordingly, shortening of the light emitting wavelength of a mother skeleton or narrowing of the spectrum was required.

On the other hand, in the compound represented by the general formula (1), its mother skeleton itself contributes to shortening of the light emitting wavelength and inhibition of the chromaticity change at the time of luminance modulation. Accordingly, in the compound represented by the general formula (1), the substituent on its mother skeleton is not substantially restricted, and the above-described effects can be obtained. However, in preferred embodiments according to the present invention, the shortening of the light emitting wavelength and the inhibition of the chromaticity change at the time of luminance modulation may be more improved by using a specified substituent.

<Compound Represented by the General Formula (1)>

In the present invention, the hydrogen atom in the description of the general formula (1) also includes isotopes (a deuterium atom and the like), and the atoms constituting the substituent are also intended to include isotopes of the atoms.

In the present invention, the "substituent" at each occurrence may be further substituted. For example, in the present invention, the "alkyl group" at each occurrence includes an alkyl group substituted with a fluorine atom (for example, a trifluoromethyl group), an alkyl group substituted with an aryl group (for example, a triphenylmethyl group), and the like, but "an alkyl group having from 1 to 6 carbon atoms" represents one having from 1 to 6 carbon atoms, as any group also including substituted groups thereof.

The "alkyl group" in the description of the present invention may be linear, branched, or cyclic. In general, the alkyl group is an alkyl group having from 1 to 30 carbon atoms, preferably from 1 to 20 carbon atoms, more preferably from 1 to 10 carbon atoms, still more preferably from 1 to 6 carbon atoms, and most preferably from 1 to 4 carbon atoms. Examples thereof include a methyl group, an ethyl group, an n-propyl group, an isopropyl group, an n-butyl group, an isobutyl group, a sec-butyl group, a t-butyl group, an n-pentyl group, an isopentyl group, a neopentyl group, an n-hexyl group, an n-octyl group, an n-decyl group, an n-hexadecyl group, a cyclopropyl group, a cyclopentyl group, and a cyclohexyl group, with a methyl group, an ethyl group, an n-propyl group, an n-butyl group, a t-butyl group, a cyclopentyl group, and a cyclohexyl group being preferable. For example, a methyl group, an isopropyl group, a t-butyl group, a cyclopentyl group, and a cyclohexyl group can be preferably adopted. The alkyl group may further have a substituent. Examples thereof include substituents of Substituent Group A as described later.

It is preferable that the "silyl group" in the description of the present invention is substituted, and as the substituent, an alkyl group and an aryl group are preferable. In the case where the silyl group is substituted with an alkyl group or an aryl group, it is more preferable that all of the hydrogen atoms are substituted with an alkyl group or an aryl group to form a trialkylsilyl group or a triarylsilyl group. Still more preferably, a trimethylsilyl group or a triphenylsilyl group is formed.

As the "heteroaryl group" in the description of the present invention, a nitrogen atom-containing 5- or 6-membered heterocyclic ring is preferable. Examples of the nitrogen atom-containing 5- or 6-membered heterocyclic ring include a pyridine ring, a pyrimidine ring, a pyrazine ring, a triazine ring, an imidazole ring, a pyrazole ring, an oxazole ring, a triazole ring, a triazole ring, an oxadiazole ring, and a thiadiazole ring. Above all, the nitrogen atom-containing 5- or 6-membered heterocyclic ring is more preferably a pyridine ring, a pyrazine ring, an imidazole ring, or a pyrazole ring; especially preferably a pyridine ring, an imidazole ring, or a pyrazine ring; still more preferably a pyridine ring or an imidazole ring are; and most preferably a pyridine ring.

The "aryl group" in the description of the present invention has preferably from 6 to 30 carbon atoms, more preferably from 6 to 20 carbon atoms, and especially preferably from 6 to 12 carbon atoms, and examples thereof include a phenyl group, a naphthyl group, and an anthranyl group. The aryl group may be any of a monocyclic aryl group or an aryl group having a fused ring. In the case of a monocyclic aryl group, the aryl group is preferably a phenyl group, and in the case of an aryl group having a fused ring, the aryl group is preferably a naphthylene group.

The aryl group or the heteroaryl group may be further substituted with the substituent described in Substituent Group A as described later. Examples thereof include those substituted with an alkyl group, an aryl group, a heteroaryl group, an amino group, a fluorine atom, or a silyl group. Above all, those substituted with an alkyl group, an aryl group, or an amino group are preferable, and those substituted with an amino group are more preferable.

The compound represented by the general formula (1) is hereunder described in detail.

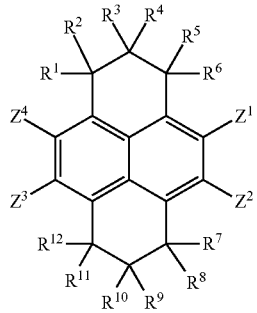

General Formula (1)

In the general formula (1), $R^1$ to $R^{12}$ each independently represent a hydrogen atom or a substituent, and these may be bound to each other to form a ring, provided that the ring obtained by these being bonded is not an aromatic ring; $Z^1$ to $Z^4$ each independently represent a hydrogen atom or a substituent; and $Z^1$ and $Z^2$, and $Z^3$ and $Z^4$, may be bound to each other to form a ring.

In the general formula (1), $R^1$ to $R^{12}$ each independently represent a hydrogen atom or a substituent, and these may be bound to each other to form a ring, provided that the ring obtained by these being bonded is not an aromatic ring. In the general formula (1), examples of the substituents represented by $R^1$ to $R^{12}$ include those in Substituent Group A as described below.

<<Substituent Group A>>

An alkyl group (having preferably from 1 to 30 carbon atoms, more preferably from 1 to 20 carbon atoms, and especially preferably from 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (having preferably from 2 to 30 carbon atoms, more preferably from 2 to 20 carbon atoms, and especially preferably from 2 to 10 carbon atoms; for example, vinyl, allyl, 2-butenyl, and 3-pentenyl), an alkynyl group (having preferably from 2 to 30 carbon atoms, more preferably from 2 to 20 carbon atoms, and especially preferably from 2 to 10 carbon atoms; for example, propargyl, and 3-pentynyl), an aryl group (having preferably from 6 to 30 carbon atoms, more preferably from 6 to 20 carbon atoms, and especially preferably from 6 to 12 carbon atoms; for example, phenyl, p-methylphenyl, naphthyl, and anthranyl), an amino group (having preferably from 0 to 30 carbon atoms, more preferably from 0 to 20 carbon atoms, and especially preferably from 0 to 10 carbon atoms; for example, amino, methylamino, dimethylamino, diethylamino, dibenzylamino, diphenylamino, and ditolylamino), an alkoxy group (having preferably from 1 to 30 carbon atoms, more preferably from 1 to 20 carbon atoms, and especially preferably from 1 to 10 carbon atoms; for example, methoxy, ethoxy, butoxy, and 2-ethylhexyloxy), an aryloxy group (having preferably from 6 to 30 carbon atoms, more preferably from 6 to 20 carbon atoms, and especially preferably from 6 to 12 carbon atoms; for example, phenyloxy, 1-naphthyloxy, and 2-naphthyloxy), a heterocyclic oxy group (having preferably from 1 to 30 carbon atoms, more preferably from 1 to 20 carbon atoms, and especially preferably from 1 to 12 carbon atoms; for example, pyridyloxy, pyrazyloxy, pyrimidyloxy, and quinolyloxy), an acyl group (having preferably from 2 to 30 carbon atoms, more preferably from 2 to 20 carbon atoms, and especially preferably from 2 to 12 carbon atoms; for example, acetyl, benzoyl, formyl, and pivaloyl), an alkoxycarbonyl group (having preferably from 2 to 30 carbon atoms, more preferably from 2 to 20 carbon atoms, and especially preferably from 2 to 12 carbon atoms; for example, methoxycarbonyl, and ethoxycarbonyl), an aryloxycarbonyl group (having preferably from 7 to 30 carbon atoms, more preferably from 7 to 20 carbon atoms, and especially preferably from 7 to 12 carbon atoms; for example, phenyloxycarbonyl), an acyloxy group (having preferably from 2 to 30 carbon atoms, more preferably from 2 to 20 carbon atoms, and especially preferably from 2 to 10 carbon atoms; for example, acetoxy and benzoyloxy), an acylamino group (having preferably from 2 to 30 carbon atoms, more preferably from 2 to 20 carbon atoms, and especially preferably from 2 to 10 carbon atoms; for example, acetylamino and benzoylamino), an alkoxycarbonylamino group (having preferably from 2 to 30 carbon atoms, more preferably from 2 to 20 carbon atoms, and especially preferably from 2 to 12 carbon atoms; for example, methoxycarbonylamino), an aryloxycarbonylamino group (having preferably from 7 to 30 carbon atoms, more preferably from 7 to 20 carbon atoms, and especially preferably from 7 to 12 carbon atoms; for example, phenyloxycarbonylamino), a sulfonylamino group (having preferably from 1 to 30 carbon atoms, more preferably from 1 to 20 carbon atoms, and especially preferably from 1 to 12 carbon atoms; for example, methanesulfonylamino and benzenesulfonylamino), a sulfamoyl group (having preferably from 0 to 30 carbon atoms, more preferably from 0 to 20 carbon atoms, and especially preferably from 0 to 12 carbon atoms; for example, sulfamoyl, methyl sulfamoyl, dimethyl sulfamoyl, and phenyl sulfamoyl), a carbamoyl group (having preferably from 1 to 30 carbon atoms, more preferably from 1 to 20 carbon atoms, and especially preferably from 1 to 12 carbon atoms; for example, carbamoyl, methyl carbamoyl, diethyl carbamoyl, and phenyl carbamoyl), an alkylthio group (having preferably from 1 to 30 carbon atoms, more preferably from 1 to 20 carbon atoms, and especially preferably from 1 to 12 carbon atoms; for example, methylthio and ethylthio), an arylthio group (having preferably from 6 to 30 carbon atoms, more preferably from 6 to 20 carbon atoms, and especially preferably from 6 to 12 carbon atoms; for example, phenylthio), a heterocyclic thio group (having preferably from 1 to 30 carbon atoms, more preferably from 1 to 20 carbon atoms, and especially preferably from 1 to 12 carbon atoms; for example, pyridylthio, 2-benzimizolylthio, 2-benzoxazolylthio, and 2-benzthiazolylthio), a sulfonyl group (having preferably from 1 to 30 carbon atoms, more preferably from 1 to 20 carbon atoms, and especially preferably from 1 to 12 carbon atoms; for example, mesyl and tosyl), a sulfinyl group (having preferably from 1 to 30 carbon atoms, more preferably from 1 to 20 carbon atoms, and especially preferably from 1 to 12 carbon atoms; for example, methane sulfinyl and benzene sulfinyl), a ureido group (having preferably from 1 to 30 carbon atoms, more preferably from 1 to 20 carbon atoms, and especially preferably from 1 to 12 carbon atoms; for example, ureido, methylureido, and phenylureido), a phosphoramide group (having preferably from 1 to 30 carbon atoms, more preferably from 1 to 20 carbon atoms, and especially preferably from 1 to 12 carbon atoms; for example, diethylphosphoramide and phenylphosphoramide), a hydroxyl group, a mercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazino group, an imino group, a heterocyclic group (inclusive of an aromatic heterocyclic group, which has preferably from 1 to 30 carbon atoms, and more preferably from 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, and a silolyl group), a silyl group (having preferably from 3 to 40 carbon atoms, more preferably from 3 to 30 carbon atoms, and especially preferably from 3 to 24 carbon atoms; for example, trimethylsilyl, triphenylsilyl, and the like), a silyloxy group (having preferably from 3 to 40 carbon atoms, more preferably from 3 to 30 carbon atoms, and especially preferably from 3 to 24 carbon atoms; for example, trimethylsilyloxy and triphenylsilyloxy), a phosphoryl group (for example, diphenylphosphoryl group and dimethylphosphoryl group). These substituents may be further substituted, and examples of the further substituent include the groups selected from the Substituent Group A as described above. In addition, the substituent substituted on the substituent may be further substituted, and examples of the further substituent include the groups selected from the Substituent Group A as described above. In addition, the substituent substituted on the substituent that has been substituted with the substituent may be still further substituted, and examples of the still further substituent include the groups selected from the Substituent Group A as described above.

$R^1$ to $R^{12}$ each preferably represent a hydrogen atom, an alkyl group, an aryl group, a heteroaryl group, $-NY^1Y^2$, $-OY^3$, $-SY^4$ ($Y^1$ to $Y^4$ each independently represent an alkyl group, an aryl group, or a heteroaryl group, and these may further have substituents), a halogen atom, or a silyl group, and more preferably represent a hydrogen atom.

In $R^1$ to $R^{12}$, when the ring obtained by these being bonded is not an aromatic ring, these may be bound to each other to form a ring. In that case, the ring to be formed is preferably a 5- or 6-membered ring. Examples of the 5- or 6-membered ring to be formed include, in addition to a cycloalkenyl ring, those containing from 1 to 3 hetero atoms selected from the group consisting of a nitrogen atom, an oxygen atom, and a sulfur atom among the atoms constituting the ring. The 5- or 6-membered ring to be formed may have a substituent, and examples of the substituent on the carbon atom include the groups selected from the Substituent Group A as described above, and examples of the substituent on the hetero atom include those in Substituent Group B as described below.

<<Substituent Group B>>

An alkyl group (having preferably from 1 to 30 carbon atoms, more preferably from 1 to 20 carbon atoms, and especially preferably from 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (having preferably from 2 to 30 carbon atoms, more preferably from 2 to 20 carbon atoms, and especially preferably from 2 to 10 carbon atoms; for example, vinyl, allyl, 2-butenyl, and 3-pentenyl), an alkynyl group (having preferably from 2 to 30 carbon atoms, more preferably from 2 to 20 carbon atoms, and especially preferably from 2 to 10 carbon atoms; for example, propargyl and 3-pentynyl), an aryl group (having preferably from 6 to 30 carbon atoms, more preferably from 6 to 20 carbon atoms, and especially preferably from 6 to 12 carbon atoms; for example, phenyl, p-methylphenyl, naphthyl, and anthranyl), a cyano group, and a heterocyclic group (inclusive of an aromatic heterocyclic group, which has preferably from 1 to 30 carbon atoms, and more preferably from 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, and a silolyl group). These substituents may be further substituted, and examples of the further substituent include the groups selected from the Substituent Group B as described above. In addition, the substituent substituted on the substituent may be further substituted, and examples of the further substituent include the groups selected from the Substituent Group B as described above. In addition, the substituent substituted on the substituent that has been substituted with the substituent may be still further substituted, and examples of the still further substituent include the groups selected from the Substituent Group B as described above.

$Z^1$ to $Z^4$ each independently represent a hydrogen atom or a substituent, and $Z^1$ and $Z^2$, and $Z^3$ and $Z^4$, may be bound to each other to form a ring. Examples of the substituents represented by $Z^1$ to $Z^4$ include an alkyl group, an aryl group, a silyl group, $-NY^1Y^2$, $-OY^3$, $-SY^4$ ($Y^1$ to $Y^4$ each independently represent an alkyl group, an aryl group, or a heteroaryl group, and these may further have substituents), and a group linked with a donor group via a divalent linking group.

Above all, $Z^1$ to $Z^4$ are each independently preferably a hydrogen atom, an alkyl group, an aryl group, a silyl group, $-OY^3$, $-SY^4$, or a group linked with a donor group via a divalent linking group (at that time, when $Z^1$ to $Z^4$ each represent $-OY^3$ or $-SY^4$, it is preferable that $Y^3$ or $Y^4$ is removed to serve as $-O-$ or $-S-$, thereby forming a fused ring together with the adjacent substituent among $Z^1$ to $Z^4$).

As for the substituents which the substituents represented by $Z^1$ to $Z^4$ may further have, examples of the substituent on the carbon atom include those of the Substituent Group A as described above, and examples of the substituent on the nitrogen atom include those of the Substituent Group B as described above. Above all, from the viewpoint of inhibition of association, it is preferable that the substituents which the substituents represented by $Z^1$ to $Z^4$ may further have, have an alkyl group, a silyl group, an aryl group, or a heteroaryl group.

Furthermore, it is preferable that $Z^1$ to $Z^4$ have two hydrogen atoms.

In the present invention, as for the compound represented by the general formula (1), $Z^1$ to $Z^4$ preferably have a group linked with a donor group via at least one divalent linking group, more preferably have a group linked with a donor group via one or two divalent linking groups, and especially preferably have a group linked with a donor group via two divalent linking groups.

When $Z^1$ to $Z^4$ have the donor group, the compound represented by the general formula (1) is able to make the luminous spectrum narrow and to increase the blue color purity. Here, the "donor group" as referred to in the present specification means an electron donating substituent and means a "substituent in which a σp value of the Hammett's rule exhibits a negative value". The Hammett's rule is a rule of thumb advocated by L. P. Hammett in 1935 for the purpose of quantitatively discussing influences of benzene derivatives against the reaction or equilibrium, appropriateness of which is widely admitted at present. The substituent constant as required in the Hammett's rule includes a $\sigma_p$ value and a σm value, and these values can be found out in a lot of documents. For example, the details are commentated in, INAMOTO, Naoki, *Hametto Soku—Kozo to Hannosei*—(Hammett's Rule—Structure and Reactivity—) (Maruzen Co., Ltd.); The Chemical Society of Japan Ed., *Shin Jikken Kagaku Koza* (New Courses in Experimental Chemistry) 14: Syntheses and Reactions of Organic Compounds V, page 2605 (Maruzen Co., Ltd.); NAKAYA, Tadao, *Riron Yuki Kagaku Kaisetsu* (Commentary on Theoretical Organic Chemistry), page 217 (Tokyo Kagaku Dojin Co., Ltd.); and *Chemical Review*, Vol. 91, pages 165 to 195 (1991) and the like.

Examples of the donor group include $-NY^1Y^2$, $-OY^3$, $-SY^4$ ($Y^1$ to $Y^4$ each independently represent an alkyl group, an aryl group, or a heteroaryl group, and these may further have substituents; and $Y^1$ and $Y^2$ may be bound to each other to form a ring), and a group represented by the following general formula (A).

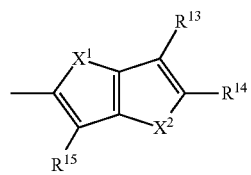

General Formula (A)

In the general formula (A), $X^1$ and $X^2$ each independently represent O, S, or $NY^5$; and $R^{13}$ to $R^{15}$ each independently represent a hydrogen atom, an alkyl group, a silyl group, an aryl group, a heteroaryl group, $-NY^1Y^2$, $-OY^3$, or $-SY^4$ ($Y^1$ to $Y^5$ each independently represent an alkyl group, an aryl group, or a heteroaryl group), and all of these may further have substituents.

$X^1$ and $X^2$ each independently represent O, S, or $NY^5$; and $Y^5$ each independently represents an alkyl group, an aryl group, or a heteroaryl group), and all of these may further have substituents. As for the substituents which these groups may further have, examples of the substituent on the carbon atom include the groups selected from the Substituent Group A as described above, and examples of the substituent on the nitrogen atom include those in the Substituent Group B as described above.

$X^1$ and $X^2$ are preferably O or S, and more preferably S.

$R^{13}$ to $R^{15}$ each independently represent a hydrogen atom, an alkyl group, a silyl group, an aryl group, a heteroaryl group, $-NY^1Y^2$, $-OY^3$, or $-SY^4$; and $Y^1$ to $Y^4$ each independently represent an alkyl group, an aryl group, or a heteroaryl group, and all of these may further have substituents. $R^{13}$ to $R^{15}$ are preferably a hydrogen atom, an alkyl group, an aryl group, or $-NY^1Y^2$, and more preferably an alkyl group or $-NY^1Y^2$.

As for the substituents which these groups may further have, examples of the substituent on the carbon atom include the groups selected from the Substituent Group A as described above, and examples of the substituent on the nitrogen atom include those in the Substituent Group B as described above. Above all, from the viewpoint of inhibition of association, it is preferable that the substituents which the substituents may further have, have an alkyl group, a silyl group, an aryl group, or a heteroaryl group.

The donor group which $Z^1$ to $Z^4$ in the general formula (1) preferably have via a divalent linking group is preferably $-NY^1Y^2$, $-OY^3$, or the group represented by the general formula (A), and more preferably $-NY^1Y^2$. Furthermore, from the viewpoint of inhibition of association, the donor group preferably has an alkyl group, a silyl group, an aryl group, or a heteroaryl group.

The compound represented by the general formula (1) is preferably a compound represented by the following general formula (2).

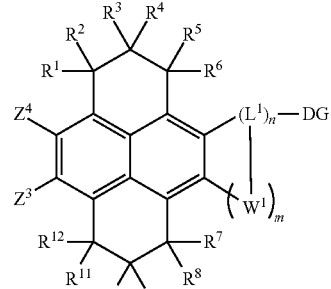

General Formula (2)

In the general formula (2), the definitions of the respective symbols which are common to those in the general formula (1) are synonymous with those in the general formula (1), respectively, and preferred examples thereof are also the same. $L^1$ represents a divalent or higher linking group; $W^1$ represents O, S, $CY^8Y^9$, or $NY^6$ ($Y^6$, $Y^8$, and $Y^9$ each independently represent an alkyl group, a silyl group, an aryl group, or a heteroaryl group, and these may further have substituents); $L^1$ and $W^1$, and $Z^3$ and $Z^4$, may be bound to each other to form a ring; DG represents a donor group; n represents an integer of 1 or 2; m represents 0 or 1; and when m is 0, then $L^1$ and $W^1$ are not bound to each other.

The compound represented by the general formula (2) is preferably a compound represented by the following general formula (3).

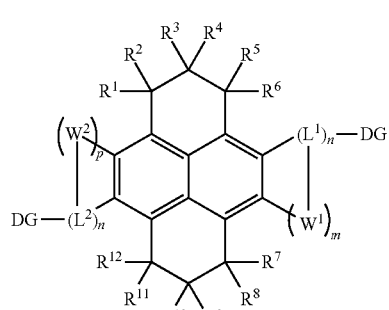

General Formula (3)

In the general formula (3), the definitions of the respective symbols which are common to those in the general formula (1) are synonymous with those in the general formula (1), respectively, and preferred examples thereof are also the same. $L^1$ and $L^2$ each independently represent a divalent or higher linking group; $W^1$ and $W^2$ each independently represent O, S, $CY^8Y^9$, or $NY^6$ ($Y^6$, $Y^8$, and $Y^9$ each independently represent an alkyl group, a silyl group, an aryl group, or a heteroaryl group, and these may further have substituents); $L^1$ and $W^1$, and $L^2$ and $W^2$, may be bound to each other to form a ring; DG represents a donor group; n represents an integer of 1 or 2; m and p represent an integer of 0 or 1; and when m or p is 0, then $L^1$ and $W^1$, and $L^3$ and $W^2$, are not bonded to each other.

$W^1$ and $W^2$ each independently represent O, S, $CY^8Y^9$, or $NY^6$; and $Y^6$, $Y^8$, and $Y^9$ each independently represent an alkyl group, a silyl group, an aryl group, or a heteroaryl group, and these may further have substituents. $W^1$ and $W^2$ are each independently preferably O, $CY^8Y^9$, or $NY^6$, and more preferably O or $CY^8Y^9$. In particular, preferred examples thereof include $C(CH_3)_2$ and $C(CH_2)_5$. As for the substituents which these groups may further have, examples of the substituent on the carbon atom include the groups selected from the Substituent Group A as described above, and examples of the substituent on the nitrogen atom include those in the Substituent Group B as described above.

$L^1$ and $L^2$ each independently represent a divalent or higher linking group; in the general formula (2), $L^1$ and $W^1$, and $Z^3$ and $Z^4$, may be bound to each other to form a ring; and in the general formula (3), $W^1$ and $L^1$, and $W^2$ and $L^2$, may be bound to each other to form a ring.

Examples of $L^1$ and $L^2$ include an arylene group, a heteroarylene group, an alkenylene group, and an alkynylene group. Of these, an arylene group or a heteroarylene group is preferable; an arylene group having the number of ring members of from 6 to 18 or a heteroarylene group having the number of ring members of from 5 to 20 is more preferable; and an arylene group having the number of ring members of from 6 to 12 or a heteroarylene group having the number of ring members of from 5 to 16 is especially preferable.

In the case where $L^1$ and $L^2$ represent an arylene group or a heteroarylene group, the arylene group or the heteroarylene group may have a substituent. At that time, though the substituent is not particularly limited, a substituent having a Hammett substituent constant σp value of not more than 0.1 is preferable, and a substituent having a Hammett substituent constant σp value of from –0.6 to 0 is more preferable.

Above all, in the case where $L^1$ and $L^2$ represent an arylene group or a heteroarylene group, the substituent which the arylene group and the heteroarylene group have is preferably a hydrogen atom, a fluorine atom, an alkyl group, a silyl group, an aryl group, a heteroaryl group, —$NY^1Y^2$, —$OY^3$, or —$SY^4$ ($Y^1$ to $Y^4$ each independently represent an alkyl group, an aryl group, or a heteroaryl group), and more preferably an alkyl group, an aryl group, or a heteroaryl group. These may further have a substituent.

In the case where $L^1$ and $L^2$ represent an arylene group or a heteroarylene group, $L^1$ and $L^2$ are each independently preferably a group represented by any one of the following general formulae (4) to (7) or a combination of two or more groups represented by the following general formulae (4) to (7), and especially preferably a group represented by any one of the following general formulae (4) to (7) (provided that a substituent with a Hammett substituent constant $\sigma_p$ value of 0.1 or more is not included in the linking group represented by the following general formulae (4) to (7).)

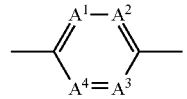

General Formula (4)

In the general formula (4), $A^1$ to $A^4$ each independently represent $CY^7$ or N; $A^1$ and $A^2$ may be fused to form an aromatic ring; $Y^7$ represents a hydrogen atom, an alkyl group, an aryl group, or a heteroaryl group, and these may further have substituents; $W^1$ is bound to $A^4$ when m in the general formula (2) is 1; and $W^1$ and $W^2$ are bound to $A^4$ when m and p in the general formula (3) each independently represent 1.

$A^1$ to $A^4$ each independently represent $CY^7$ or N; and $Y^7$ represents a hydrogen atom, an alkyl group, an aryl group, or a heteroaryl group, and these may further have substituents. $A^1$ to $A^4$ are each independently preferably CH, CR (R represents an alkyl group), CAr (Ar represents an aryl group), or N, and more preferably CH or N. The number of N atoms in $A^1$ to $A^4$ is preferably from 0 to 3, more preferably from 0 to 2, especially preferably 0 or 1, and more especially preferably 0.

As for the substituents which these groups may further have, examples of the substituent on the carbon atom include the groups selected from the Substituent Group A as described above, and examples of the substituent on the nitrogen atom include those in the Substituent Group B as described above.

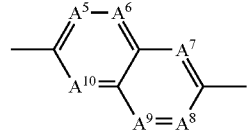

General Formula (5)

In the general formula (5), $A^5$ to $A^{10}$ each independently represent $CY^7$ or N; $Y^7$ represents a hydrogen atom, an alkyl group, an aryl group, or a heteroaryl group, and these may further have substituents; $W^1$ is bound to $A^5$ or $A^{10}$ when m in the general formula (2) is 1; and $W^1$ and $W^2$ are bound to $A^5$ or $A^{10}$ when m and p in the general formula (3) each independently represent 1.

The description and preferred ranges of $A^5$ to $A^{10}$ in the general formula (5) are the same as the description and preferred ranges of $A^1$ to $A^4$ in the general formula (4).

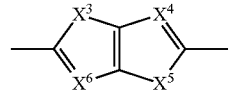

General Formula (6)

In the general formula (6), $X^3$ and $X^5$ each independently represent O, S, or $NY^6$; $X^4$ and $X^6$ each independently represent $CY^7$ or N; and $Y^6$ and $Y^7$ each independently represent a hydrogen atom, an alkyl group, an aryl group, or a heteroaryl group, and these may further have substituents. However, m and p in the general formula (2) or (3) are 0.

$X^3$ and $X^5$ each independently represent O, S, or $NY^6$; and $Y^6$ represents a hydrogen atom, an alkyl group, an aryl group, or a heteroaryl group, and these may further have substituents. $X^3$ and $X^5$ are each independently preferably S, NR (R represents an alkyl group), or NAr (Ar represents an aryl group), and more preferably S.

As for the substituents which these groups may further have, examples of the substituent on the carbon atom include the groups selected from the Substituent Group A as described above, and examples of the substituent on the nitrogen atom include those in the Substituent Group B as described above.

$X^4$ and $X^6$ each independently represent $CY^7$ or N; and $Y^7$ each independently represent a hydrogen atom, an alkyl group, an aryl group, or a heteroaryl group, and these may further have substituents. $X^4$ and $X^6$ are each preferably CH, CAr (Ar represents an aryl group), or N, and more preferably CH or N.

As for the substituents which these groups may further have, examples of the substituent on the carbon atom include the groups selected from the Substituent Group A as described above, and examples of the substituent on the nitrogen atom include those in the Substituent Group B as described above.

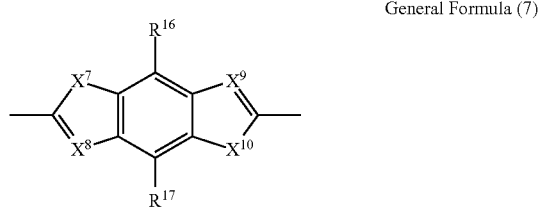

General Formula (7)

In the general formula (7), $X^7$ and $X^{10}$ each independently represent O, S or $NY^6$; $X^8$ and $X^9$ each independently represent $CY^7$ or N; $Y^6$ and $Y^7$ each independently represent a hydrogen atom, an alkyl group, an aryl group, or a heteroaryl group, and these may further have substituents; and $R^{16}$ and $R^{17}$ each independently represent a hydrogen atom, a fluorine atom, an alkyl group, a silyl group, an aryl group, a heteroaryl group, $-NY^1Y^2$, $-OY^3$, or $-SY^4$ ($Y^1$ to $Y^4$ each independently represent an alkyl group, an aryl group, or a heteroaryl group), and these may further have substituents, However, m and p in the general formula (2) or (3) are 0.

The description and preferred ranges of $X^7$ and $X^{10}$ in the general formula (7) are the same as the description and preferred ranges of $X^3$ and $X^5$ in the general formula (6).

The description and preferred ranges of $X^8$ and $X^9$ in the general formula (7) are the same as the description and preferred ranges of $X^4$ and $X^6$ in the general formula (6).

$R^{16}$ and $R^{17}$ each independently represent a hydrogen atom, a fluorine atom, an alkyl group, a silyl group, an aryl group, a heteroaryl group, $-NY^1Y^2$, $-OY^3$, or $-SY^4$ ($Y^1$ to $Y^4$ each independently represent an alkyl group, an aryl group, or a heteroaryl group), and these may further have substituents. $R^{16}$ and $R^{17}$ are each independently preferably a hydrogen atom, a fluorine atom, an alkyl group, an aryl group, or $-NY^1Y^2$, and more preferably a hydrogen atom, a fluorine atom, an alkyl group, or an aryl group.

As for the substituents which these groups may further have, examples of the substituent on the carbon atom include the groups selected from the Substituent Group A as described above, and examples of the substituent on the nitrogen atom include those in the Substituent Group B as described above.

However, $R^{16}$ and $R^{17}$ are preferably a substituent having a Hammett substituent constant σp value of not more than 0.1, and more preferably a substituent having a σp value of from −0.5 to 0.1.

In the general formulae (2) and (3), $L^1$ and $L^2$ are each preferably a linking group represented by any one of the general formulae (4), (5), and (7), and more preferably a linking group represented by the general formula (4) or (5) among the liking groups represented by the general formulae (4) to (7) from the viewpoint that the DG (donor group) linked with the pyrene skeleton via $L^1$ and $L^2$, as described later.

In addition, in the case where $L^1$ and $L^2$ are each a combination of two or more linking groups represented by the following general formulae (4) to (7), it is preferable that at least one compound represented by the general formula (4) or the general formula (5) is included. In that case, it is preferable that the compound represented by the general formula (4) contains one or two nitrogen atoms in $A^1$ to $A^4$, and it is preferable that the compound represented by the general formula (5) contains one nitrogen atom in $A^5$ to $A^{10}$.

DG in the general formulae (2) and (3) represents a donor group, and the description and a preferred range of the donor group are the same as the description and preferred range of the donor group in the description regarding the substituents represented by $Z^1$ to $Z^4$ in the general formula (1).

In addition, the general formula (2) preferably has two donor groups and has a donor group preferably in either one of $Z^3$ and $Z^4$, and more preferably in $Z^3$.

Incidentally, the donor group may be bound, as a substituent of the substituents represented by the Substituent Group B, to $L^1$ via a linking group derived from the Substituent Group B.

n represents an integer of 1 or 2.

m represents an integer of 0 or 1.

p represents an integer of 0 or 1, and when m or p is 0, then $Z^2$ and $L^1$, and $Z^4$ and $L^2$, are not bonded to each other.

The compound represented by the general formula (2) is preferably a compound represented by any one of the following general formulae (8) to (11), more preferably a compound represented by any one of the following general formulae (8), (9), and (11), and especially preferably a compound represented by the following general formula (8) or (9).

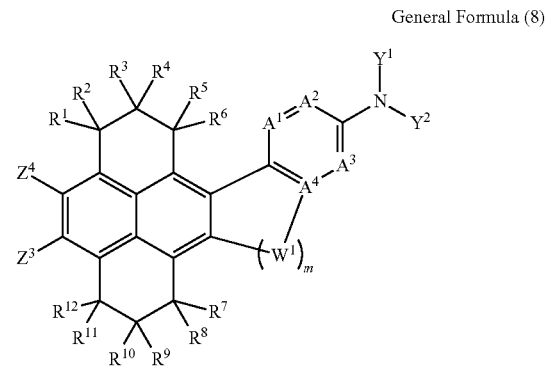

General Formula (8)

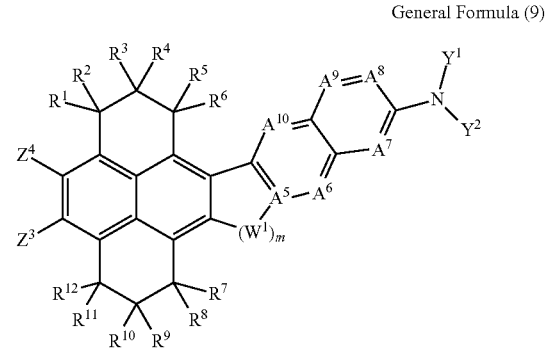

General Formula (9)

General Formula (10)

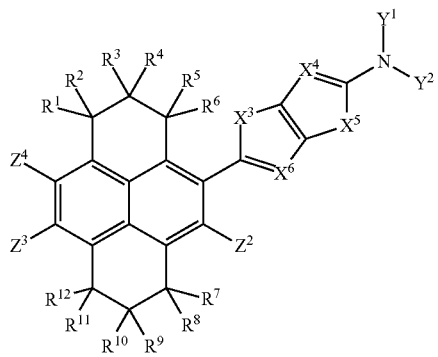

General Formula (11)

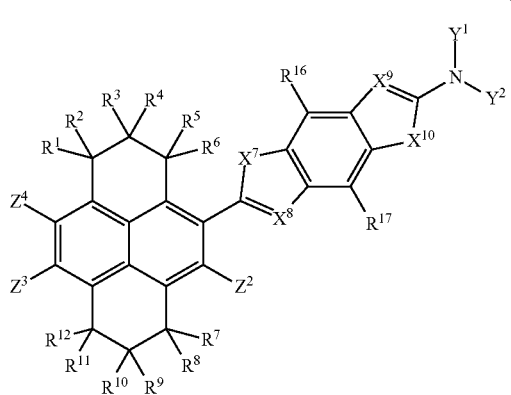

In the general formulae (8) to (11), the definitions of the respective symbols which are common to those in the general formulae (1) to (7) are synonymous with those in the general formulae (1) to (7), respectively, and preferred examples thereof are also the same. $Y^1$ and $Y^2$ each independently represent an alkyl group, an aryl group, or a heteroaryl group, and these may further have substituents and may be bound to each other to form a ring.

In the general formulae (8) to (11), $Y^1$ and $Y^2$ are each independently preferably a phenyl group, a naphthyl group, or a phenanthryl group, and more preferably a phenyl group or naphthyl group. As for the substituents which these groups may further have, examples of the substituent on the carbon atom include the groups selected from the Substituent Group A as described above, and examples of the substituent on the nitrogen atom include those in the Substituent Group B as described above. From the viewpoints of durability and inhibition of association, the substituent is preferably a deuterium atom, an alkyl group, a fluorine atom, a silyl group, an aryl group, or a heteroaryl group; more preferably a deuterium atom, a methyl group, an isopropyl group, a t-butyl group, a fluorine atom, a phenyl group ($—C_6H_5$ or $—C_6D_5$), a p-methylphenyl group (tolyl group), a p-isopropylphenyl group, an m-methylphenyl group, an o-methylphenyl group, a trimethylsilyl group, or a cyano group; and especially preferably a deuterium atom, a methyl group, an isopropyl group, a t-butyl group, a fluorine atom, a phenyl group ($—C_6H_5$ or $—C_6D_5$), a p-methylphenyl group (tolyl group), an m-methylphenyl group, or an o-methylphenyl group.

The compound represented by the general formula (8) is preferably a compound represented by the following general formula (8'). Here, the definitions of the respective symbols in the following general formula (8') are synonymous with those in the general formula (8), respectively, and preferred ranges thereof are also the same.

General Formula (8')

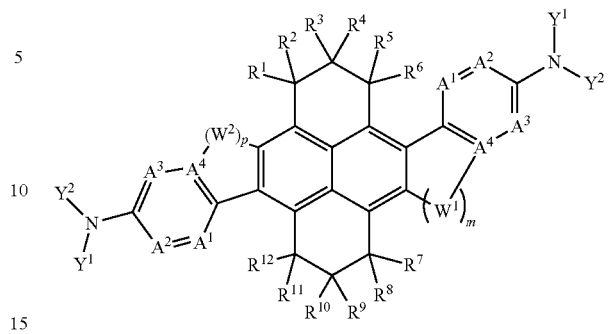

The compound represented by the general formula (9) is preferably a compound represented by the following general formula (9'). Here, the definitions of the respective symbols in the following general formula (9') are synonymous with those in the general formula (9), respectively, and preferred ranges thereof are also the same.

General Formula (9')

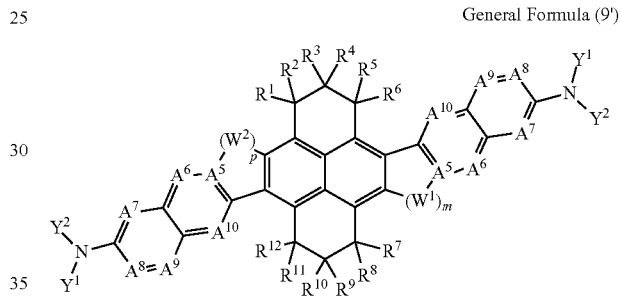

The compound represented by the general formula (10) is preferably a compound represented by the following general formula (10'). Here, the definitions of the respective symbols in the following general formula (10') are synonymous with those in the general formula (10), respectively, and preferred ranges thereof are also the same.

General Formula (10')

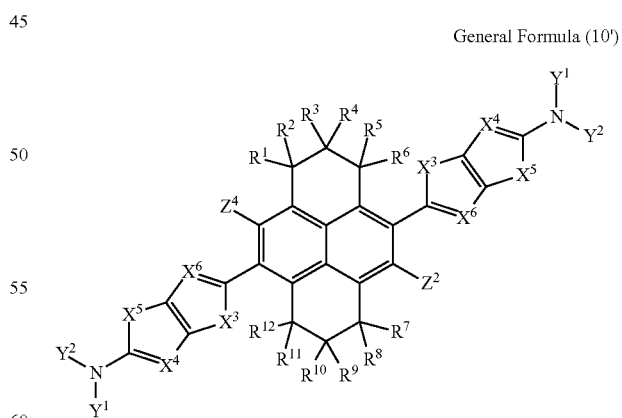

The compound represented by the general formula (11) is preferably a compound represented by the following general formula (11'). Here, the definitions of the respective symbols in the following general formula (11') are synonymous with those in the general formula (11), respectively, and preferred ranges thereof are also the same.

General Formula (11')

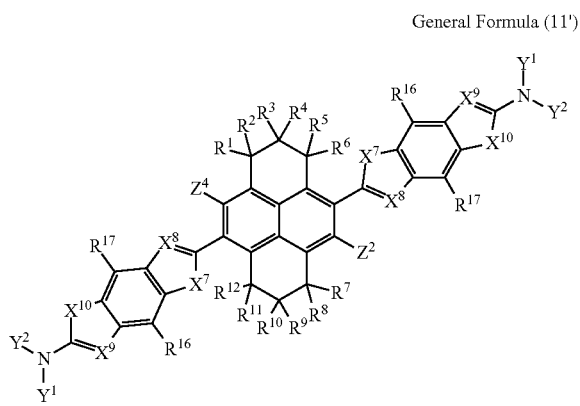

The compound represented by the general formula (8) is preferably a compound represented by the following general formula (12).

General Formula (12)

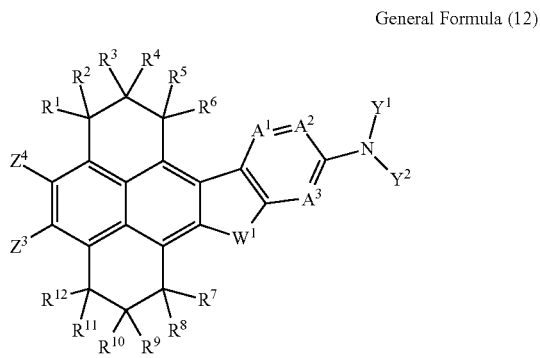

The definitions of the respective symbols in the general formula (12) are synonymous with those in the general formula (8), respectively, and preferred ranges thereof are also the same.

The compound represented by the general formula (9) is preferably a compound represented by the following general formula (13).

General Formula (13)

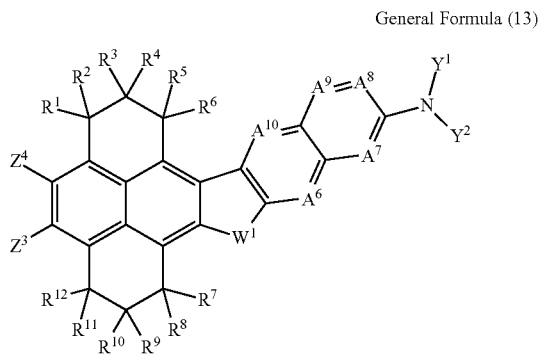

The definitions of the respective symbols in the general formula (13) are synonymous with those in the general formula (9), respectively, and preferred ranges thereof are also the same.

The compound represented by the general formula (8') or the general formula (12) is preferably a compound represented by the following general formula (14).

General Formula (14)

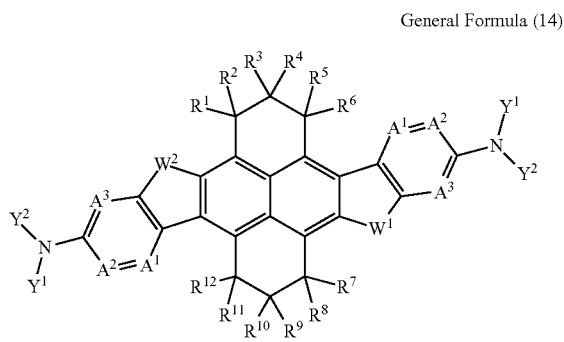

The definitions of the respective symbols in the general formula (14) are synonymous with those in the general formula (8') or the general formula (12), respectively, and preferred ranges thereof are also the same.

The compound represented by the general formula (9') or the general formula (13) is preferably a compound represented by the following general formula (15).

General Formula (15)

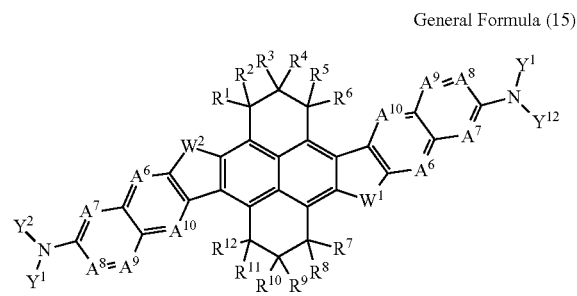

The definitions of the respective symbols in the general formula (15) are synonymous with those in the general formula (9') or the general formula (13), respectively, and preferred ranges thereof are also the same.

The organic electroluminescent element using the compound represented by the general formula (1) has a maximum light emitting wavelength of usually from 400 nm to 480 nm, preferably from 420 nm to 470 nm, and more preferably from 430 nm to 460 nm. In the present invention, in particular, when the compound represented by any one of the general formulae (8) to (13) is adopted as the compound represented by the general formula (1), the maximum light emitting wavelength of the organic electroluminescent element is from about 430 nm to 460 nm, and in particular, blue light emission with a high color purity is obtained, and therefore, such is preferable. From the viewpoint of the fact that blue light emission with a high color purity is obtained, the maximum light emitting wavelength of the organic electroluminescent element using the compound represented by the general formula (1) is most preferably 440 nm or more and less than 455 nm.

The compound represented by the general formula (1) has a molecular weight of preferably not more than 1,000, more preferably not more than 900, and still more preferably not more than 850. By lowering the molecular weight, the sublimation temperature can be lowered, and therefore, the thermal decomposition of the compound at a time of deposition can be prevented. In addition, by shortening the deposition time, energy required for the deposition can be suppressed.

Specific examples of the compound represented by the general formula (1) are shown below, but it should not be construed that the compound represented by the general formula (1) which can be used in the present invention is limited to these specific examples.

Compound 1

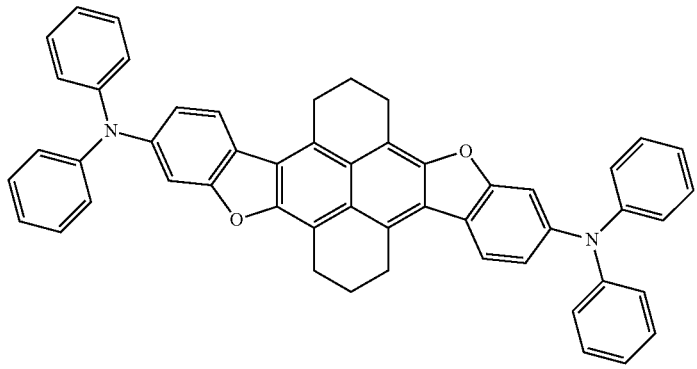

Compound 2

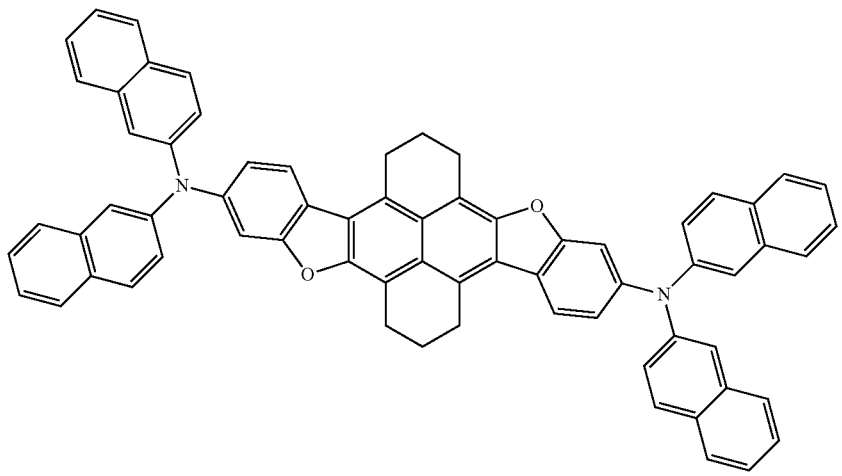

Compound 3

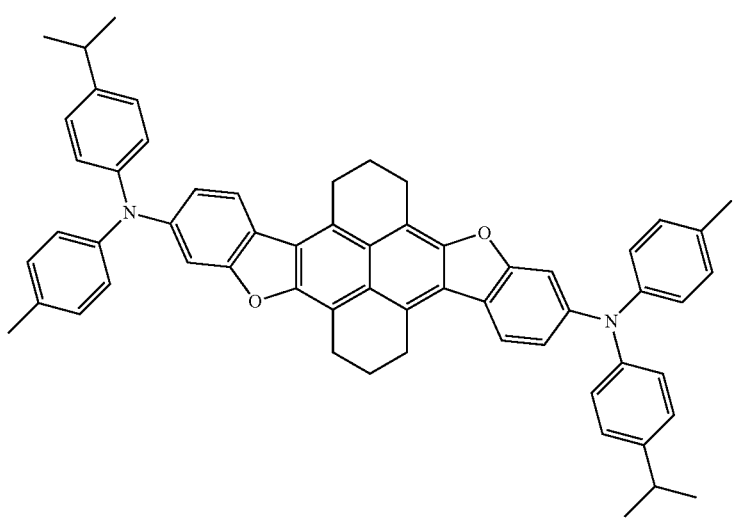

-continued
Compound 4
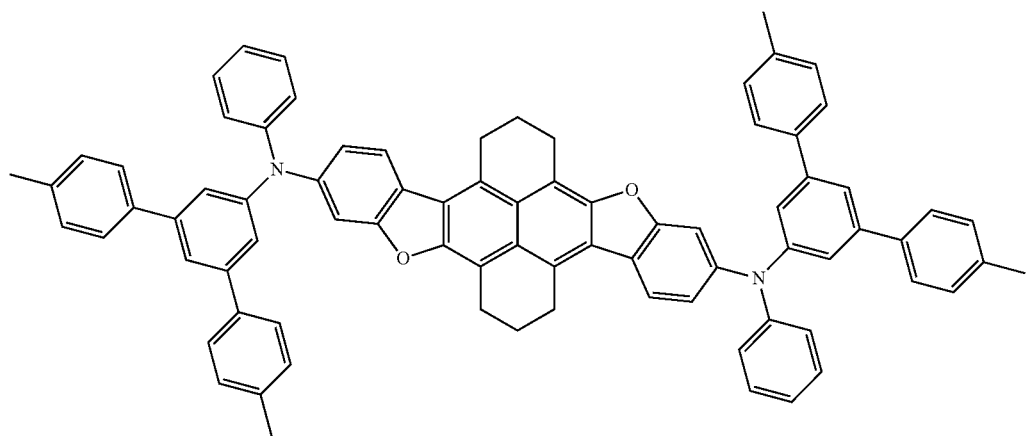
Compound 5
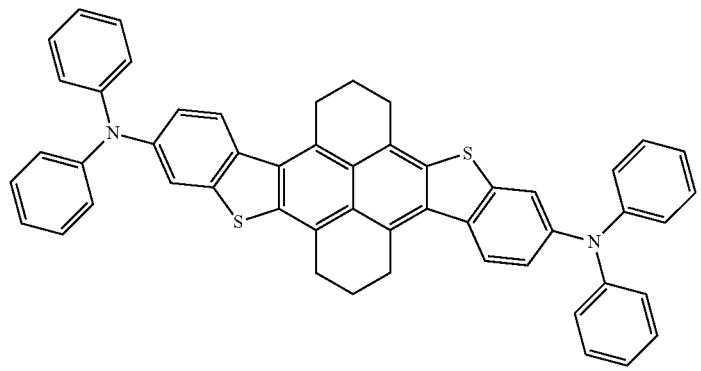
Compound 6
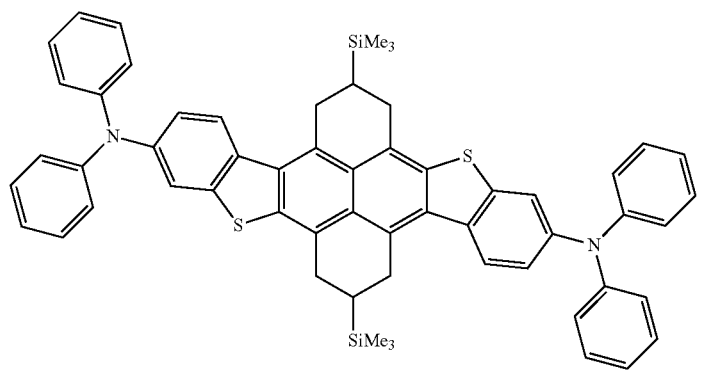

Compound 7
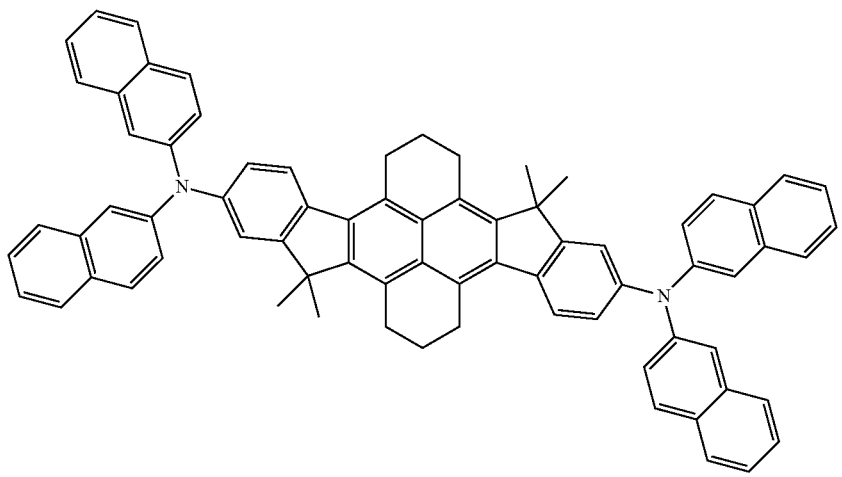
Compound 8
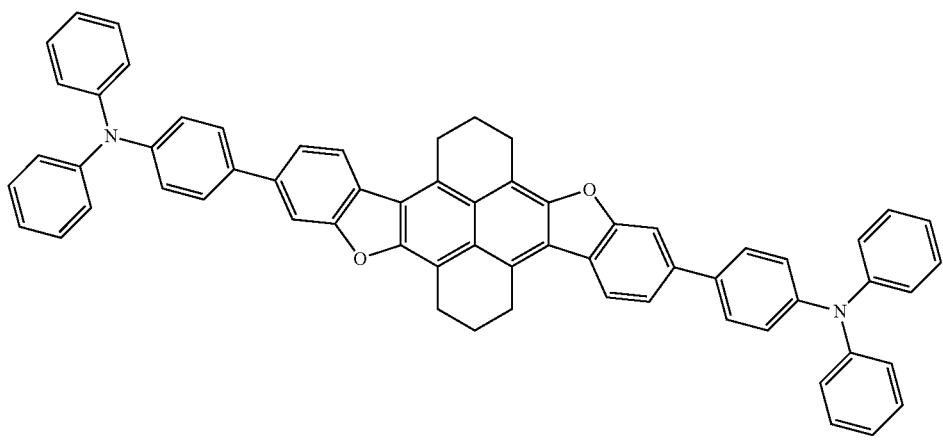
Compound 9
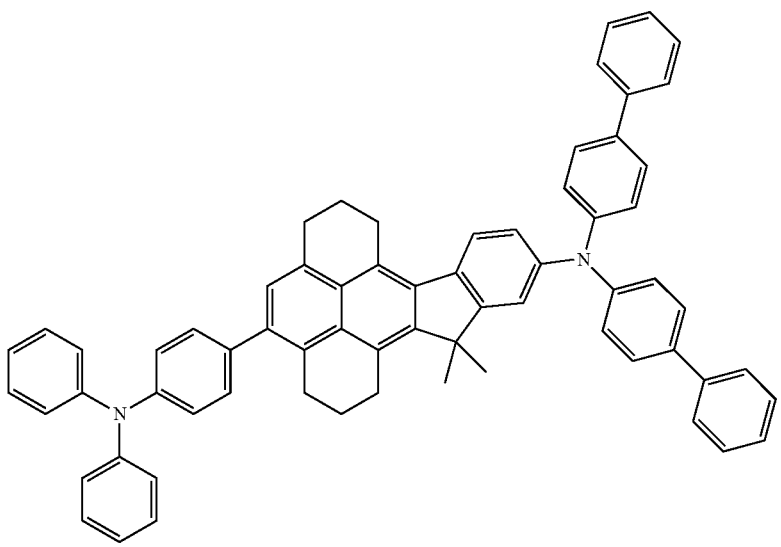

-continued
Compound 10
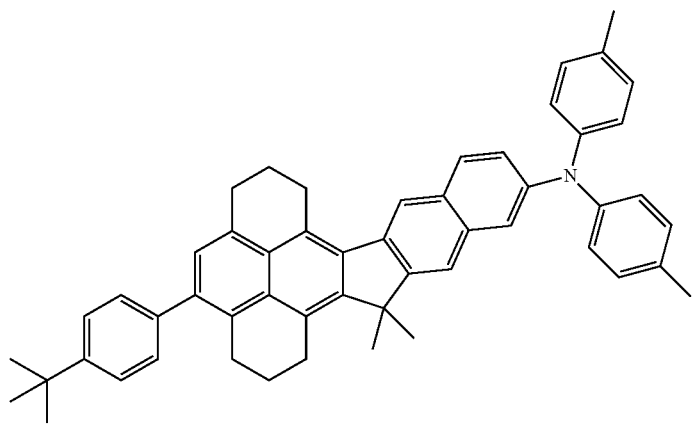
Compound 11
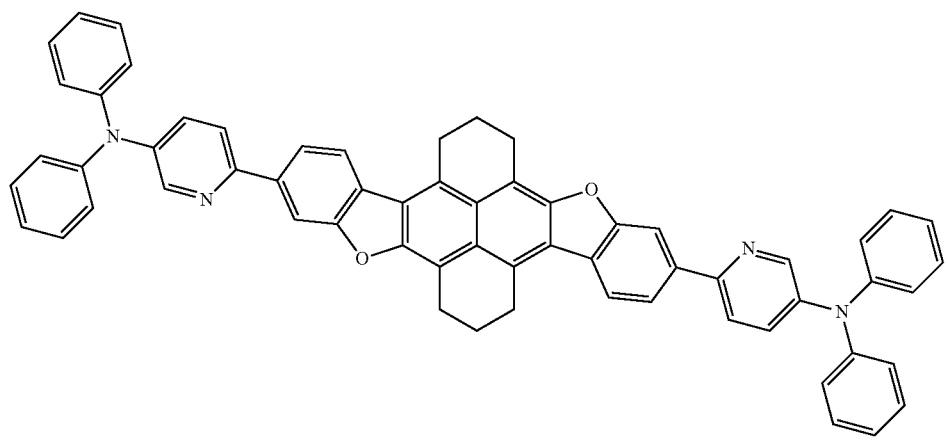
Compound 12
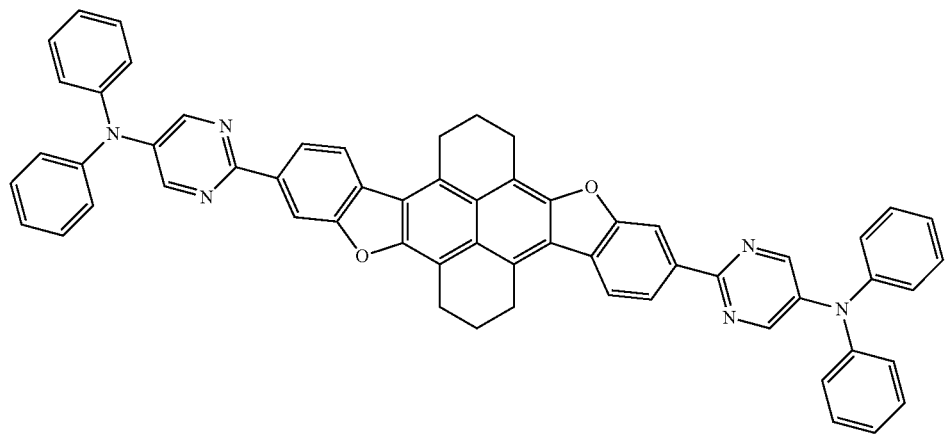

Compound 13
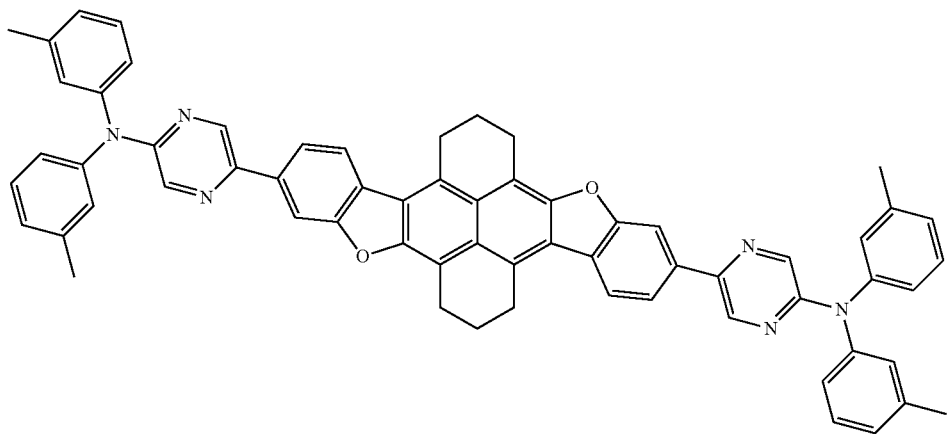
Compound 14
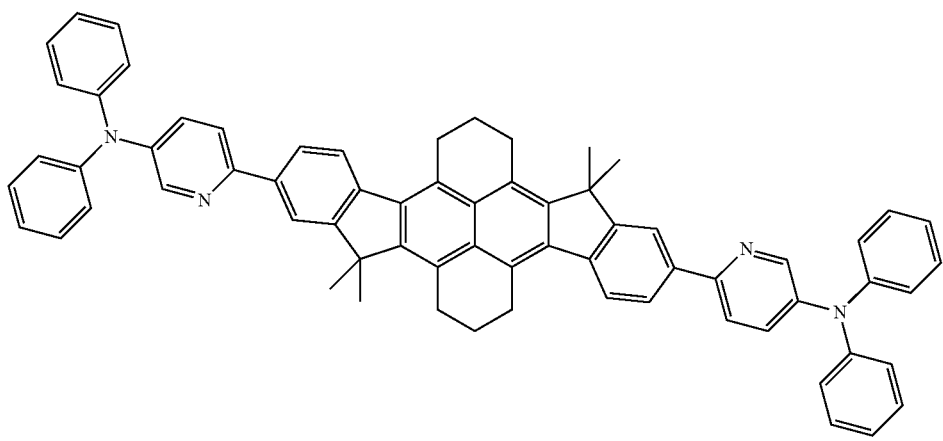
Compound 15
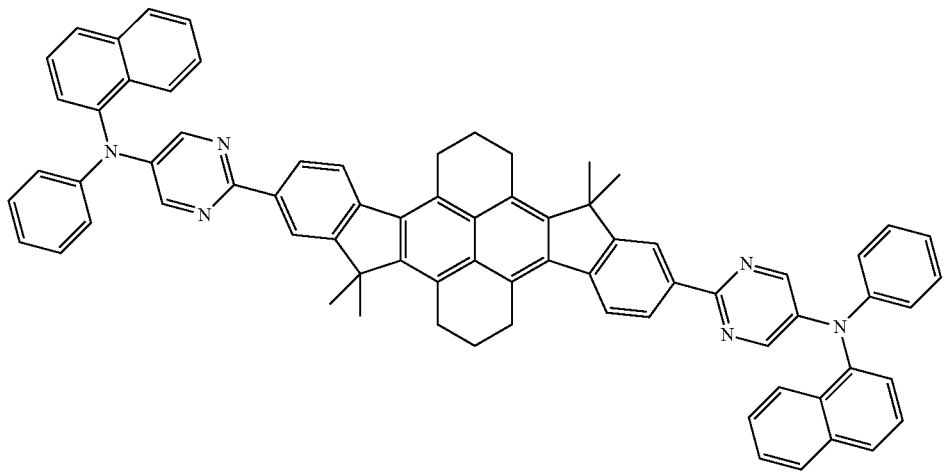

-continued
Compound 16
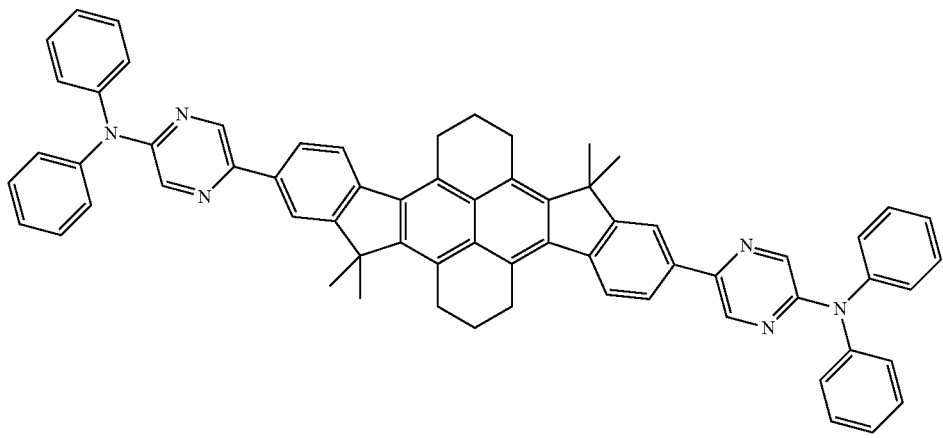
Compound 17
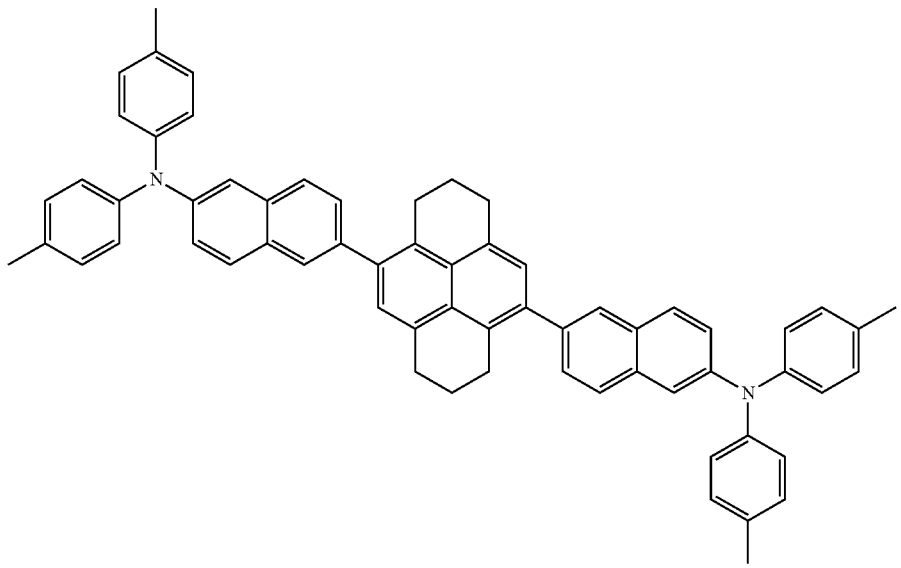
Compound 18
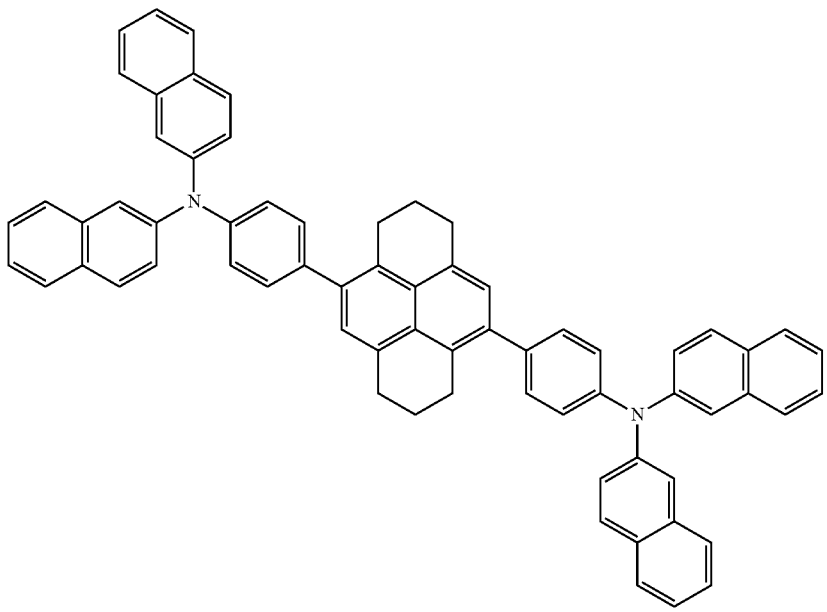

-continued
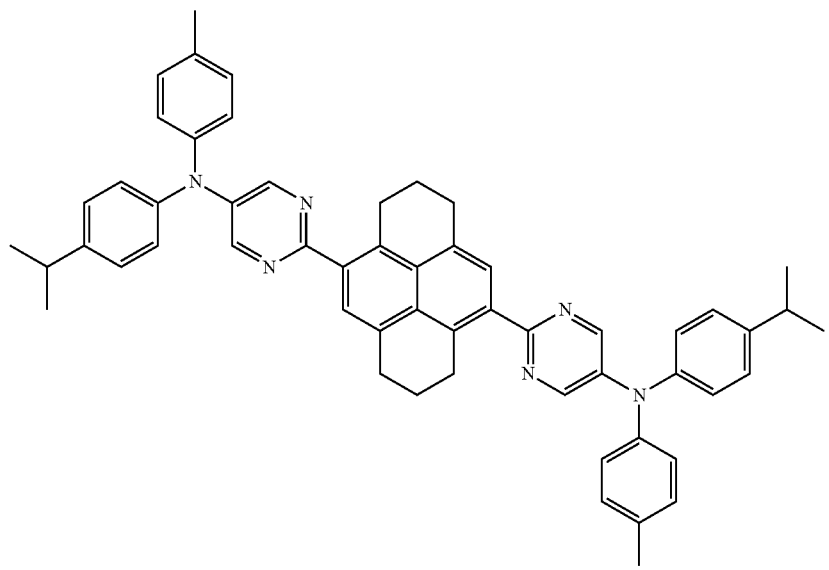
Compound 19
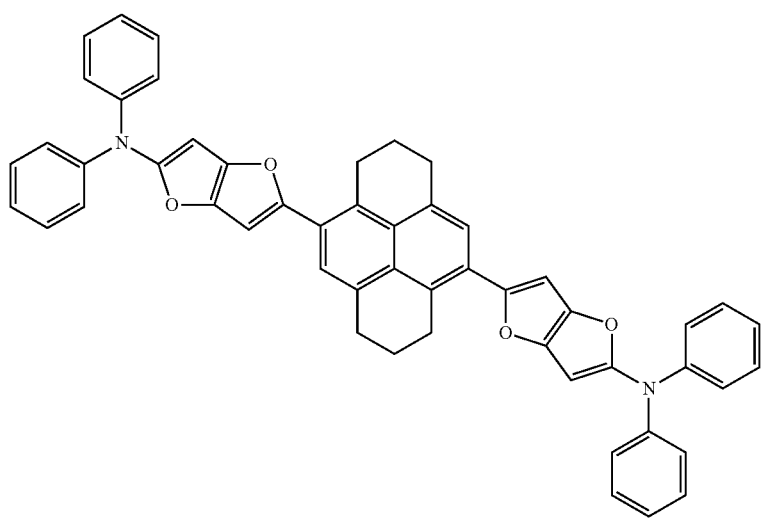
Compound 20

-continued
Compound 11
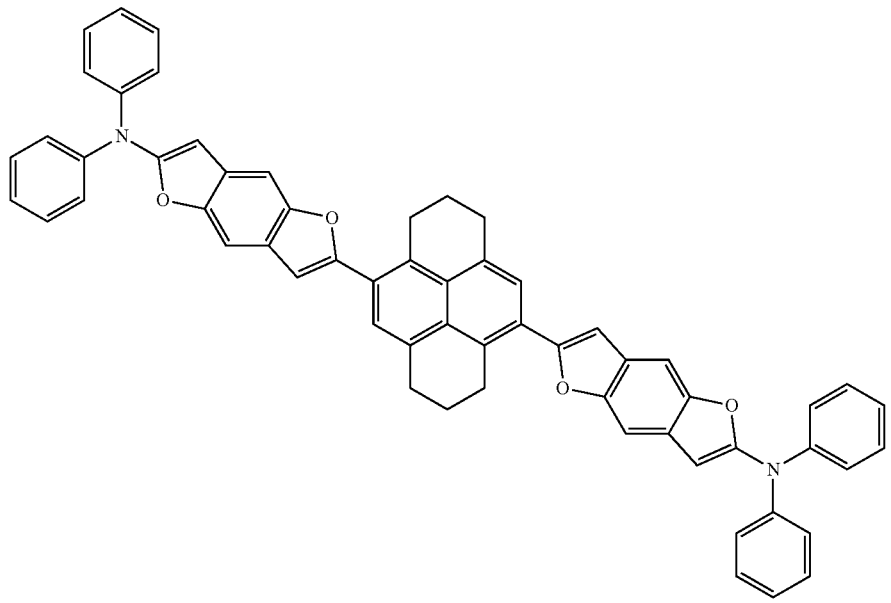
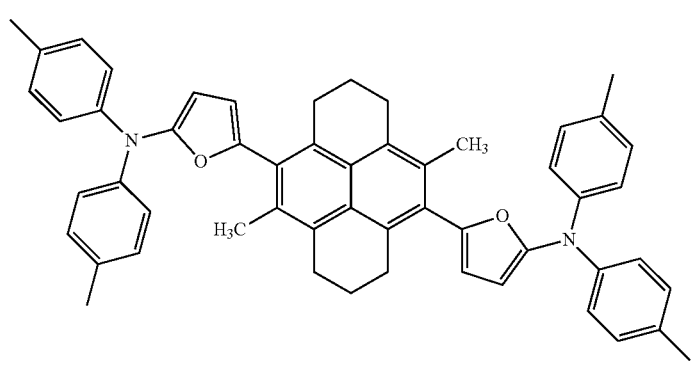
Compound 21
Compound 22
Compound 23
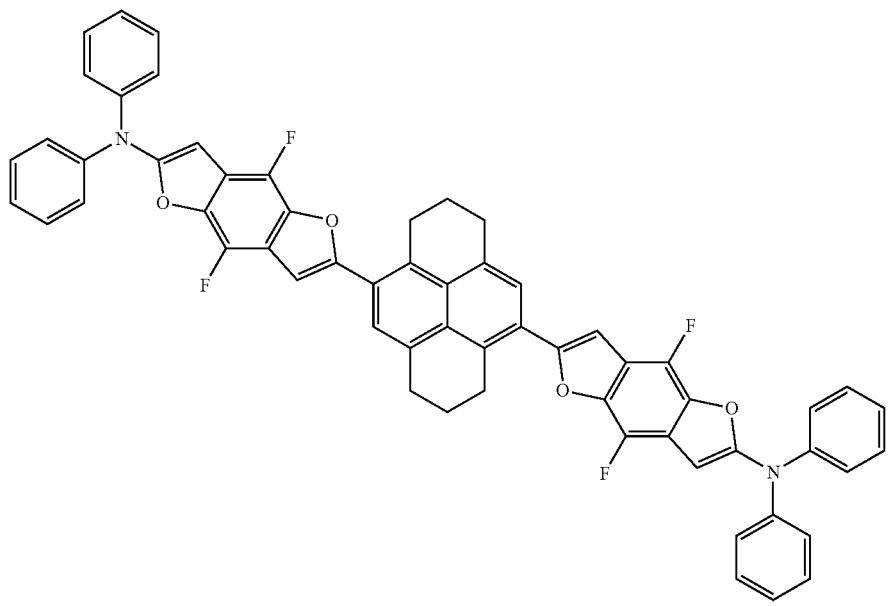

Compound 24
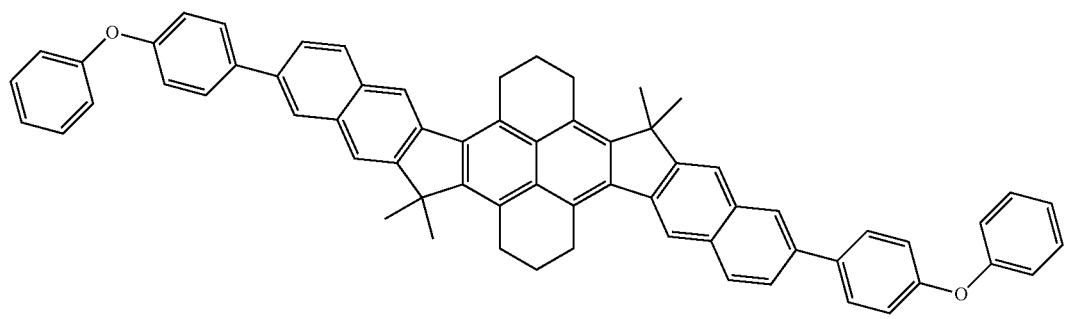
Compound 25
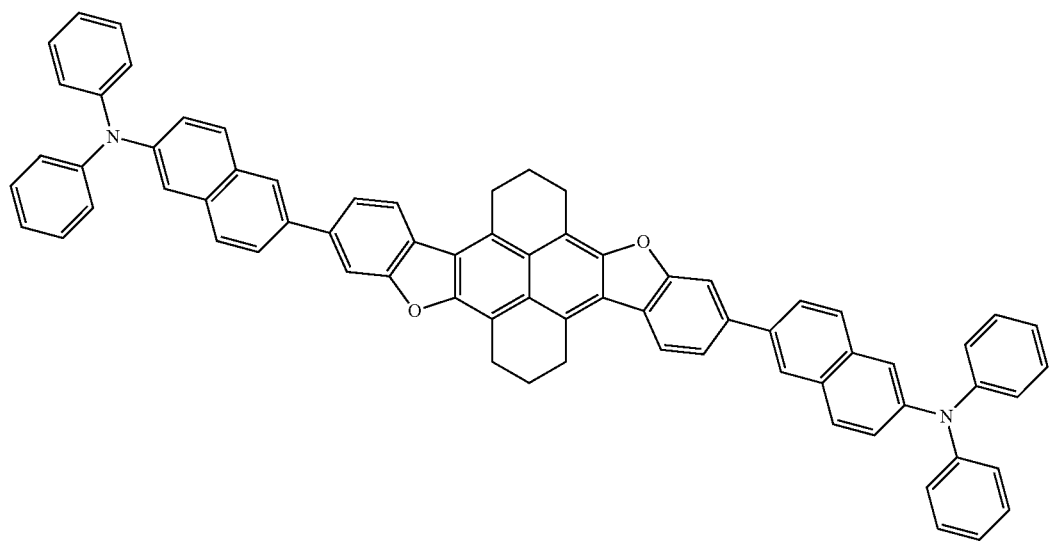
Compound 26
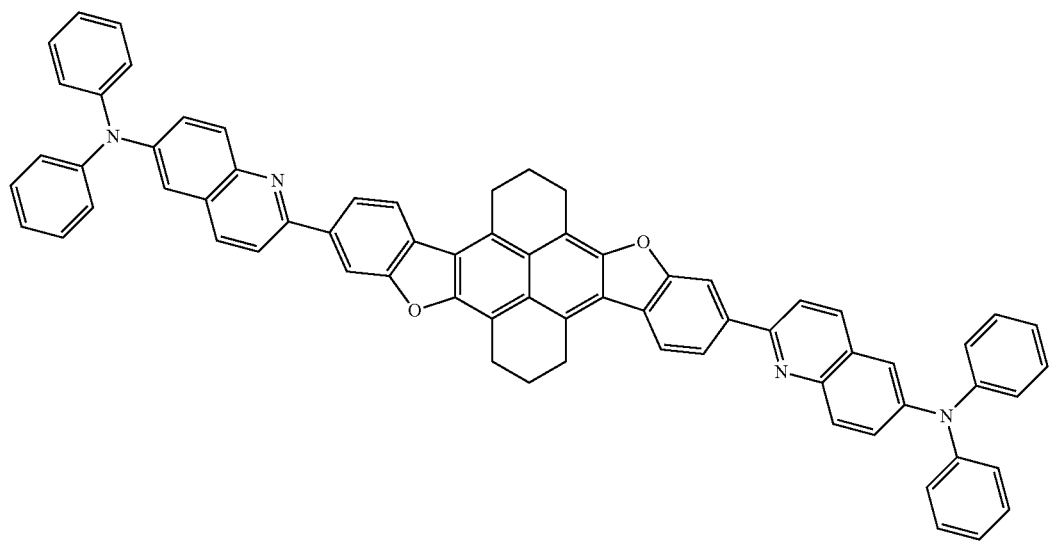

-continued
Compound 27
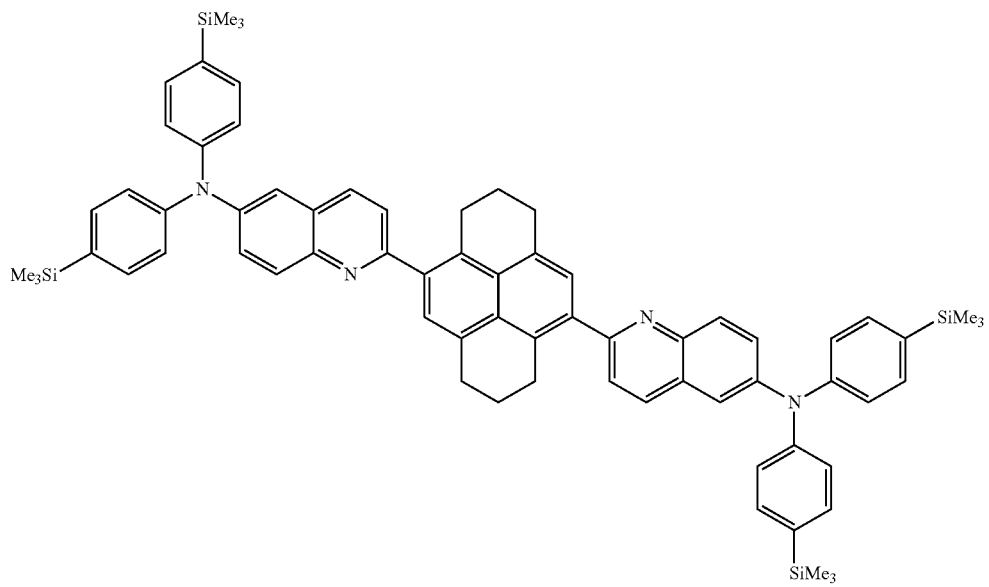
Compound 28
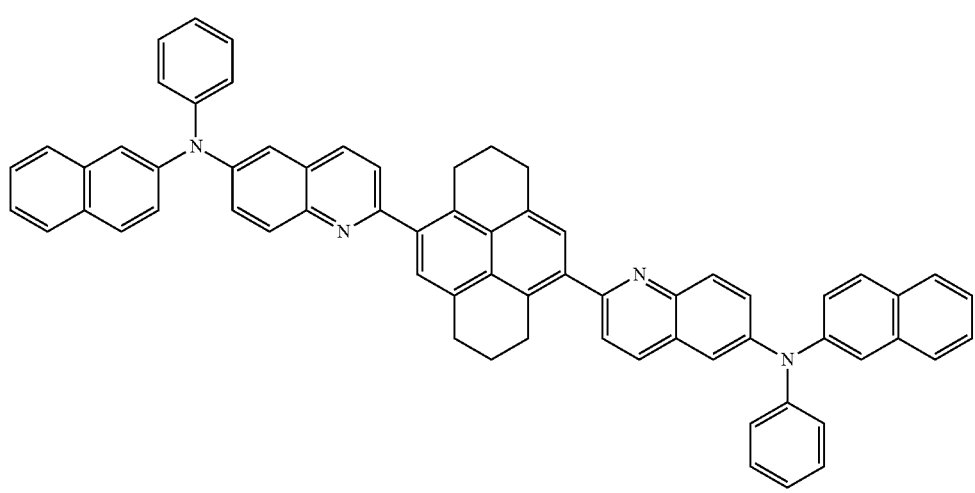
Compound 29
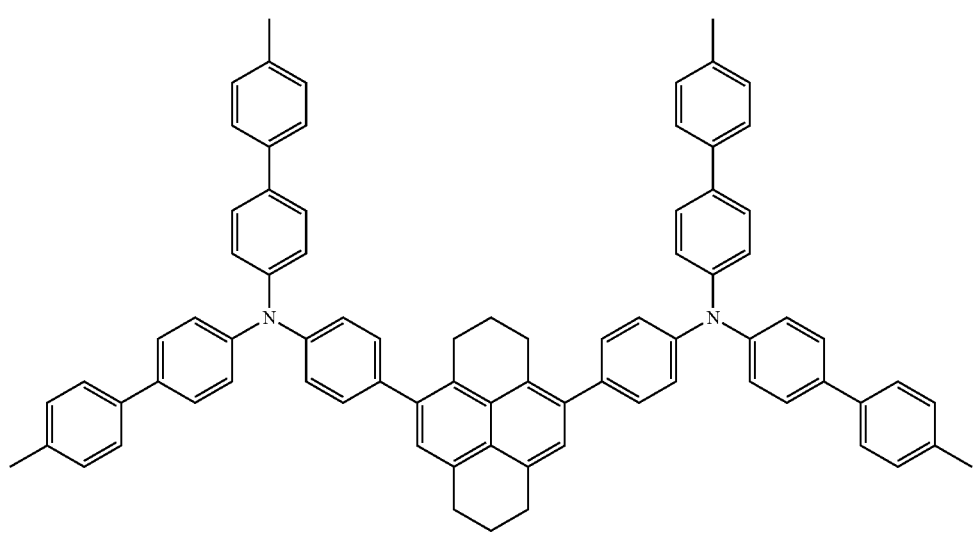

Compound 30
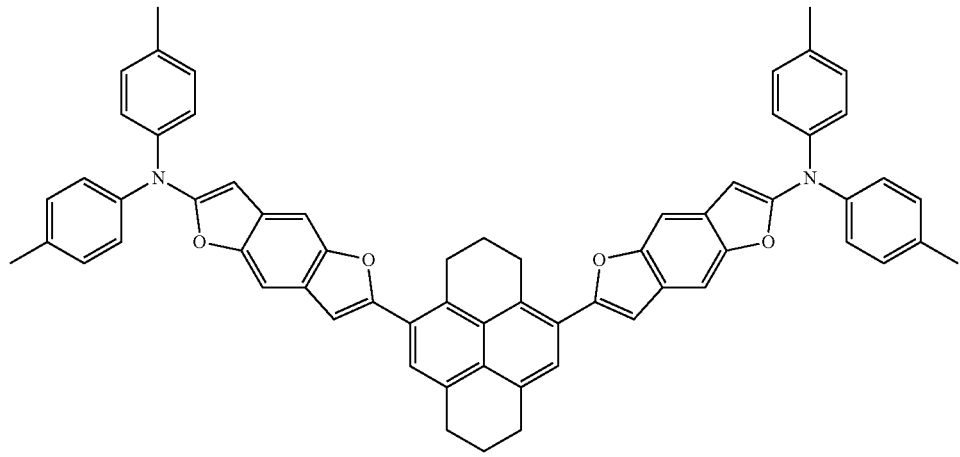
Compound 31
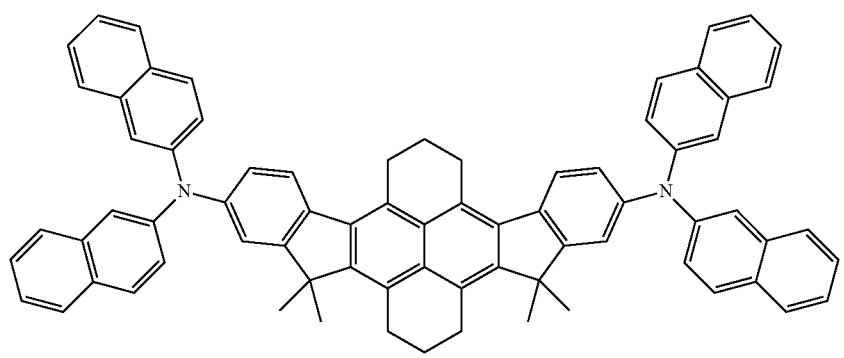
Compound 32
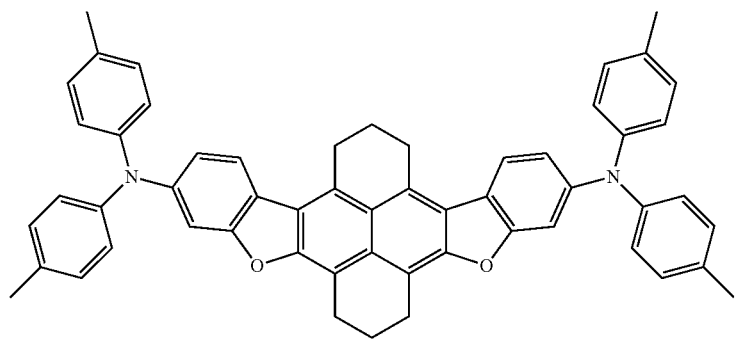
Compound 33
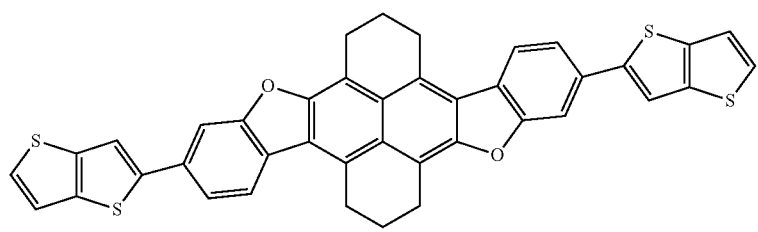

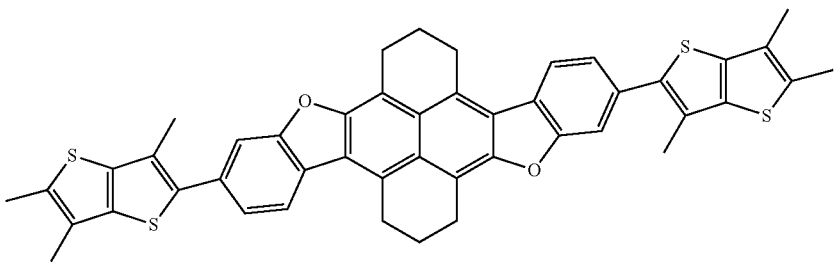

Compound 34

The compound represented by the general formula (1) can be synthesized by a combination of known reactions, and specifically, it can be synthesized by the methods described in JP-A-2009-283899 and JP-A-2006-298793. A representative example of the specific synthesis procedures of the compound represented by the general formula (1) is described below.

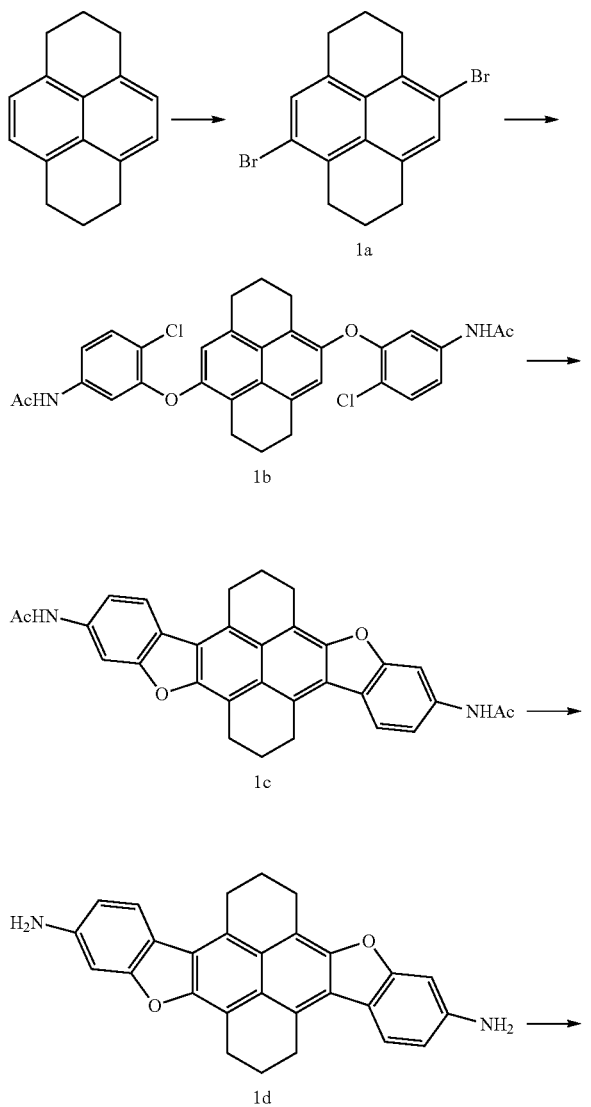

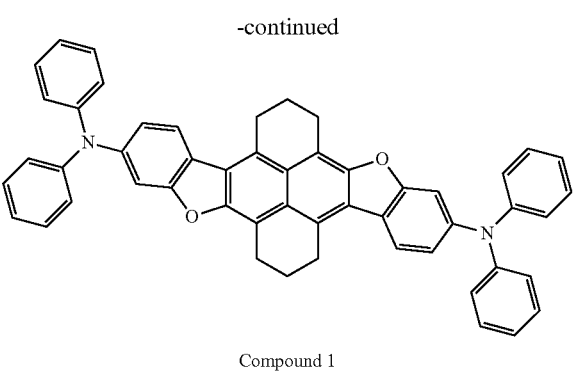

Compound 1

The respective steps can be performed according to the synthesis methods and reaction conditions described in JP-A-2009-283899, JP-A-2006-298793, and *Organic Letters*, 2005, Vol. 7, pages 1857 to 1860.

After the synthesis, it is preferable that after performing purification by means of column chromatography, recrystallization, or the like, purification is performed by means of sublimation purification. According to the sublimation purification, not only organic impurities can be separated, but inorganic salts, residual solvent, and the like can be effectively removed.

In the case of using the compound represented by the general formula (1) as a light emitting material, from the viewpoint of the fact that blue light emission with a high color purity is obtained, the maximum light emitting wavelength in the thin film state is preferably less than 460 nm, more preferably 400 nm or more and not more than 460 nm, especially preferably 420 nm or more and less than 455 nm, still more preferably 430 nm or more and less than 455 nm, and most preferably 440 nm or more and less than 455 nm.

[Organic Electroluminescent Element]

The organic electroluminescent element according to the present invention comprises a substrate; a pair of electrodes including an anode and a cathode, disposed on the substrate; and at least one organic layer disposed between the electrodes, wherein the organic layer includes at least one compound represented by the general formula (1) as a light emitting layer.

The configuration of the organic electroluminescent element according to the present invention is not particularly limited. FIG. 1 shows one example of the configuration of the organic electroluminescent element according to the present invention. An organic electroluminescent element 10 of FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed description thereon in this patent document can be applied to the present invention.

Preferred embodiments of the organic electroluminescent element according to the present invention are hereunder described in detail in the order of the substrate, the electrodes, the organic layer, the protective layer, the sealing enclosure, a driving method, a light emitting wavelength, and applications.

<Substrate>

The organic electroluminescent element according to the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferable.

<Electrodes>

The organic electroluminescent element according to the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be usually one having a function as an electrode of supplying holes into an organic layer, and is not particularly limited in terms of its shape, structure, size, or the like. Further, depending on the use and purpose of the light emitting element, the anode can be suitably selected from the known electrode materials. As described above, the anode is usually provided as a transparent anode.

(Cathode)

The cathode may be usually one having a function as an electrode of injecting electrons to an organic layer, and is not particularly limited in terms of its shape, structure, size, or the like. Further, depending on the use and purpose of the light emitting element, the cathode can be suitably selected from the known electrode materials.

<Organic Layer>

The organic electroluminescent element according to the present invention has one or plural organic layers disposed between the electrodes, wherein the organic layer includes a light emitting layer, and the light emitting layer includes a host material and at least one compound represented by the general formula (1).

The organic layer is not particularly limited and can be suitably selected depending on the use and purpose of the organic electroluminescent element. However, the organic layer is preferably formed on the transparent electrode or the semi-transparent electrode. In that case, the organic layer is formed on the whole surface or one surface of the transparent electrode or the semi-transparent electrode.

The shape, the size, the thickness, and the like of the organic layer are not particularly limited and can be suitably selected depending on the purpose.

The configuration of the organic layer, the method for forming an organic layer, preferred embodiments of the respective layers constituting the organic layer, and the materials used in the respective layers in the organic electroluminescent element according to the present invention are hereunder described in detail in order.

(Configuration of Organic Layer)

In the organic electroluminescent element according to the present invention, the organic layer includes a light emitting layer. Furthermore, the organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, an organic electroluminescent element with low costs and high efficiency can be manufactured.

The compound represented by the general formula (1) is contained in at least one layer of the light emitting layers of one or plural organic layers disposed between the electrodes of the organic electroluminescent element.

However, while not departing from the spirit of the present invention, the compound represented by the general formula (1) may also be contained in other organic layers of the organic electroluminescent element according to the present invention. Examples of the organic layer which may contain the compound represented by the general formula (1), other than the light emitting layer, include a hole injecting layer, a hole transporting layer, an electron transporting layer, an electron injecting layer, an exciton blocking layer, and a charge blocking layer (a hole blocking layer, an electron blocking layer, and the like). Such an organic layer is preferably any one of an exciton blocking layer, a charge blocking layer, an electron transporting layer, and an electron injecting layer, and more preferably any one of an exciton blocking layer, a charge blocking layer, and an electron transporting layer.

In the case where the compound represented by the general formula (1) is contained in the light emitting layer, the amount of the compound represented by the general formula (1) which is contained is preferably from 0.1 to 100% by mass, more preferably from 1 to 50% by mass, and still more preferably from 2 to 20% by mass, and particularly preferably from 3 to 10% by mass relative to the total mass of the light emitting layer.

In the case where the compound represented by the general formula (1) is contained in the organic layer other than the light emitting layer, the amount of the compound represented by the general formula (1) which is contained is preferably from 70 to 100% by mass, more preferably from 80 to 100% by mass, and still more preferably from 90 to 100% by mass relative to the total mass of the light emitting layer.

(Method for Forming Organic Layer)

The respective organic layers in the organic electroluminescent element according to the present invention can be suitably formed by any of dry film forming methods such as a deposition method and a sputtering method, wet type film forming methods (solution coating methods) such as a transfer method, a printing method, a spin coating method, and a bar coating method.

For the organic electroluminescent element according to the present invention, the organic layer disposed between a pair of electrodes preferably includes at least one layer formed by the deposition of a composition including the compound represented by the general formula (1).

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element according to the present invention may be constituted of only the compound (light emitting material) represented by the general formula (1), or may be constituted as a mixed layer of a host material and the light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Furthermore, the light emitting layer may include a material which does not have charge transporting properties and which does not emit light.

In addition, the light emitting layer may be made of a single layer or multiple layers of two or more layers. The respective layers may include the same light emitting material or host material, and may also include a different material in every layer. In the case where plural light emitting layers are present, the respective light emitting layers may emit light in a different luminous color from each other.

The thickness of the light emitting layer is not particularly limited, but it is usually from 2 nm to 300 nm, and above all, from the viewpoint of external quantum efficiency, it is more preferably from 5 nm to 100 nm, and still more preferably from 10 nm to 50 nm.

For the organic electroluminescent element according to the present invention, the light emitting layer contains the compound represented by the general formula (1), and the compound represented by the general formula (1) is used as a light emitting material of the light emitting layer. Here, the host material as referred to in the present specification is a compound which chiefly plays a role in injecting or transporting charges in the light emitting layer and is also a compound which does not substantially emit light in itself. As used herein, it is meant by the terms "which does not substantially emit light" that the amount of light emission from the compound which does not substantially emit light is preferably not more than 5%, more preferably not more than 3%, and still more preferably not more than 1% relative to the total amount of light emission in the whole of the element. The compound represented by the general formula (1) may also be used as a host material of the light emitting layer.

(Light Emitting Material)

In the organic electroluminescent element according to the present invention, though the compound represented by the general formula (1) is used as a light emitting material, even in that case, it can also be used in combination with a light emitting material other than the compound represented by the general formula (1). In addition, in the organic electroluminescent element according to the present invention, even in the case where the compound represented by the general formula (1) is used as a host material of the light emitting layer, or in the case where it is used in the organic layer other than the light emitting layer, a light emitting material other than the compound represented by the general formula (1) is used in the light emitting layer.

The light emitting material which can be used in the present invention is a fluorescent light emitting material. In addition, the light emitting layer in the present invention can contain two or more kinds of light emitting materials in order to enhance the color purity or widen the light emitting wavelength region.

The fluorescent light emitting material which can be used in the organic electroluminescent element according to the present invention is described in detail in, for example, paragraphs [0100] to [0164] of JP-A-2008-270736 and paragraphs [0088] to [0090] of JP-A-2007-266458, the detailed description of which can be applied to the present invention.

Though the kind of the fluorescent light emitting material which can be used in the present invention is not particularly limited, examples thereof include those other than the compound represented by the general formula (1), for example, benzoxazole, benzimidazole, benzothiazole, styrylbenzene, polyphenyl, diphenylbutadiene, tetraphenylbutadiene, naphthalimide, coumarin, pyran, perinone, oxadiazole, aldazine, pyraridine, cyclopentadiene, bis-styrylanthracene, quinacridone, pyrrolopyridine, thiadiazolopyridine, cyclopentadiene, styrylamine, aromatic fused polycyclic compounds (e.g., anthracene, phenanthroline, pyrene, perylene, rubrene, pentacene, and the like), a variety of metal complexes typified by metal complexes of 8-quinolinol, pyrromethene complexes, and rare earth complexes, polymer compounds such as polythiophene, polyphenylene, and polyphenylenevinylene, organic silanes, and derivatives thereof.

In addition to the above, the compound described in paragraph [0082] of JP-A-2010-111620 can also be used as the light emitting material.

The light emitting layer in the organic electroluminescent element according to the present invention may be constituted of only a light emitting material, or may be constituted as a mixed layer of a host material and a light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Furthermore, the light emitting layer may include a material which does not have charge transporting properties and which does not emit light.

In addition, the light emitting layer may be made of a single layer or multiple layers of two or more layers. The respective layers may include the same light emitting material or host material, and may also include a different material in every layer. In the case where plural light emitting layers are present, the respective light emitting layers may emit light in a different luminous color from each other.

(Host Material)

The host material is a compound which chiefly plays a role in injecting or transporting charges in the light emitting layer and is also a compound which does not substantially emit light in itself. As used herein, it is meant by the terms "which does not substantially emit light" that the amount of light emission from the compound which does not substantially emit light is preferably not more than 5%, more preferably not more than 3%, and still more preferably not more than 1% relative to the total amount of light emission in the whole of the element.

Examples of the host material which can be used in the organic electroluminescent element according to the present invention include the following compounds, for example:

Conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, porphyrin-based compounds, aromatic hydrocarbon compounds with fused rings (e.g., fluorene, naphthalene, phenanthrene, triphenylene, and the like), polysilane-based compounds, poly(N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring). In addition to the above, the compounds described in paragraph [0081] or [0083] of JP-A-2010-111620 can also be used.

Of these, carbazole, dibenzothiophene, dibenzofuran, arylamines, aromatic hydrocarbon compounds with fused rings, and metal complexes are preferable, and aromatic hydrocarbon compounds with fused rings are particularly preferable because they are stable. As the aromatic hydrocarbon compounds with fused rings, naphthalene-based compounds, anthracene-based compounds, phenanthrene-based compounds, triphenylene-based compounds, and pyrene-based compounds are preferable; anthracene-based compounds and pyrene-based compounds are more preferable; and anthracene-based compounds are particularly preferable. As for the anthracene-based compounds, those described in paragraphs [0033] to [0064] of WO 2010/134350 are particularly preferable, and examples thereof include Compounds H-1 and H-2 as described later.

In the organic electroluminescent element according to the present invention, it is preferable that the host material which is included in the light emitting layer has a hydrocarbon fused ring structure having from 10 to 50 carbon atoms.

As for the hydrocarbon fused ring structure having from 10 to 50 carbon atoms, naphthalene, phenanthrene, benzo[c]phenanthrene, anthracene, pyrene, triphenylene, and chrysene are preferable; naphthalene, phenanthrene, benzo[c]phenanthrene, and anthracene are more preferable; and anthracene is the most preferable. That is, it is more preferable that the hydrocarbon fused ring structure having from 10 to 50 carbon atoms of the host material is an anthracene skeleton. Furthermore, it is the most preferable that the hydrocarbon fused ring structure having from 10 to 50 carbon atoms is a compound constituted of only carbon and hydrogen or deuterium.

The host material which can be used in the light emitting layer in the organic electroluminescent element according to the present invention may be a hole transporting host material or a electron transporting host material.

In the light emitting layer, the singlet lowest excited energy ($S_1$ energy) in the film state of the host material is preferably higher than the $S_1$ energy of the light emitting material in view of color purity, luminous efficiency, and driving durability. The $S_1$ of the host material is preferably higher than the $S_1$ of the light emitting material by 0.1 eV or more, more preferably by 0.2 eV or more, and still more preferably by 0.3 eV or more.

When $S_1$ in the film state of the host material is lower than $S_1$ of the light emitting material, the light emission is lost, and thus, the host material is required to have higher $S_1$ than that of the light emitting material. In addition, even in the case where $S_1$ of the host material is higher than that of the light emitting material, a small difference in the $S_1$ of the both leads to partial reverse energy movement from the light emitting material to the host material, which causes reduction in efficiency, color purity, or durability. Therefore, there is a demand for a host material having a sufficiently high $S_1$, and high chemical stability and carrier injecting/transporting properties.

In addition, though the content of the host compound in the light emitting layer in the organic electroluminescent element according to the present invention is not particularly limited, from the viewpoints of luminous efficiency and driving voltage, it is preferably from 15 to 98% by mass, and more preferably from 80 to 97% by mass relative to the total mass of the compounds forming the light emitting layer. In the case where the light emitting layer includes plural kinds of host compounds including the compound represented by the general formula (1), the content of the compound represented by the general formula (1) is preferably from 50 to 99% by mass in the whole of the host compounds.

(Other Layers)

The organic electroluminescent element according to the present invention may include layers other than the light emitting layer.

Examples of the organic layer other than the light emitting layer which may be included in the organic layer include a hole injecting layer, a hole transporting layer, a blocking layer (e.g., a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injecting layer/cathode Anode/hole injecting layer/hole transporting layer/light emitting layer/blocking layer/electron transporting layer/cathode Anode/hole injecting layer/hole transporting layer/light emitting layer/electron transporting layer/electron injecting layer/cathode Anode/hole injecting layer/hole transporting layer/light emitting layer/blocking layer/electron transporting layer/electron injecting layer/cathode Anode/hole injecting layer/hole transporting layer/blocking layer/light emitting layer/blocking layer/electron transporting layer/electron injecting layer/cathode The organic electroluminescent element according to the present invention preferably includes at least one organic layer which is preferably disposed between the (A) anode and the light emitting layer. Examples of the organic layer which is preferably disposed between the (A) anode and the light emitting layer include an hole injecting layer, a hole transporting layer, and an electron blocking layer from the anode side.

The organic electroluminescent element according to the present invention preferably includes at least one organic layer which is preferably disposed between the (B) cathode and the light emitting layer. Examples of the organic layer which is preferably disposed between the (B) cathode and the light emitting layer include an electron injecting layer, an electron transporting layer, and a hole blocking layer from the cathode side.

Specifically, an example of the preferred embodiments of the organic electroluminescent element according to the present invention is the embodiment shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

These layers other than the light emitting layer which the organic electroluminescent element according to the present invention may have are hereunder described.

(A) Organic Layer Preferably Disposed Between Anode and Light Emitting Layer:

First, (A) the organic layer preferably disposed between the anode and the light emitting layer is described.

(A-1) Hole Injecting Layer and Hole Transporting Layer:

The hole injecting layer and the hole transporting layer are a layer having a function of receiving holes from the anode or the anode side and transporting them to the cathode side.

The light emitting element according to the present invention preferably includes at least one organic layer between the light emitting layer and the anode, and the organic layer preferably includes at least one of compounds among compounds represented by the following general formulae (Sa-1), (Sb-1), and (Sc-1).

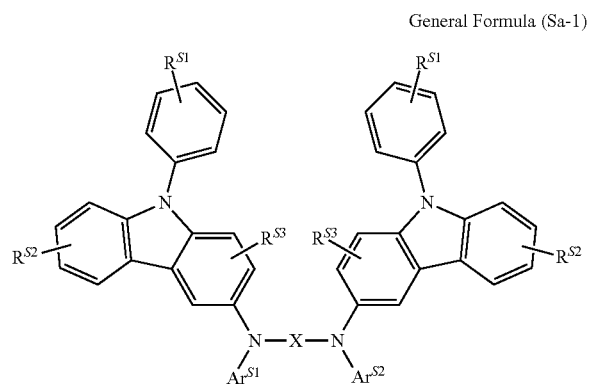

General Formula (Sa-1)

(In the formula, X represents a substituted or unsubstituted alkylene group having from 1 to 30 carbon atoms, a substituted or unsubstituted alkenylene group having from 2 to 30 carbon atoms, a substituted or unsubstituted arylene group having from 6 to 30 carbon atoms, a substituted or unsubstituted heteroarylene group having from 2 to 30 carbon atoms, or a substituted or unsubstituted heterocyclic group having from 2 to 30 carbon atoms, or a group formed by a combination of these groups. $R^{S1}$, $R^{S2}$, and $R^{S3}$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, a substituted or unsubstituted fused polycyclic group having from 5 to 30 carbon atoms, a hydroxyl group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Ar^{S1}$ and $Ar^{S2}$ each independently represent a substituted or unsubstituted aryl group having from 6 to 30 carbon atoms or a substituted or unsubstituted heteroaryl group having from 2 to 30 carbon atoms.)

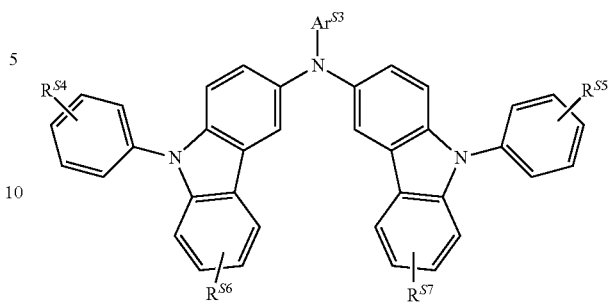

General Formula (Sb-1)

(In the formula, $R^{S4}$, $R^{S5}$, $R^{S6}$, and $R^{S7}$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, a substituted or unsubstituted fused polycyclic group having from 5 to 30 carbon atoms, a hydroxyl group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Ar^{S3}$ represents a substituted or unsubstituted aryl group having from 6 to 30 carbon atoms or a substituted or unsubstituted heteroaryl group having from 2 to 30 carbon atoms.)

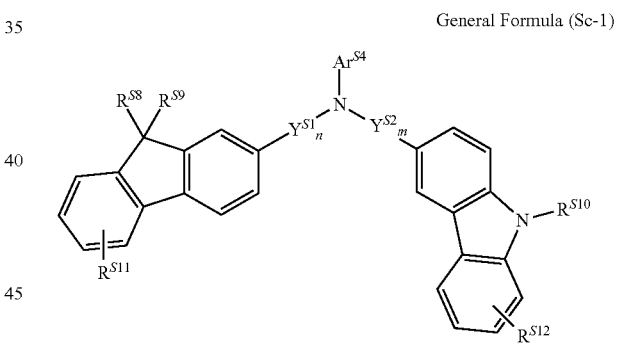

General Formula (Sc-1)

(In the formula, $R^{S8}$ and $R^{S9}$ each independently represent a hydrogen atom, a substituted or unsubstituted alkyl group having from 1 to 30 carbon atoms, a substituted or unsubstituted aryl group having from 6 to 30 carbon atoms, a substituted or unsubstituted heterocyclic group having from 2 to 30 carbon atoms, or a substituted or unsubstituted fused polycyclic group having from 5 to 30 carbon atoms. $R^{S10}$ represents a substituted or unsubstituted alkyl group having from 1 to 30 carbon atoms, a substituted or unsubstituted aryl group having from 6 to 30 carbon atoms, a substituted or unsubstituted heterocyclic group having from 2 to 30 carbon atoms, or a substituted or unsubstituted fused polycyclic group having from 5 to 30 carbon atoms. $R^{S11}$ and $R^{S12}$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, a substituted or unsubstituted fused polycyclic group having from 5 to 30 carbon atoms, a hydroxyl group, a cyano group, or a substituted or unsubstituted amino group. Adjacent $R^{S11}$ and $R^{S12}$ may be bonded to each other to form a saturated carbocycle or an unsaturated carbocycle. $Ar^{S4}$ represents a substituted or unsubstituted aryl group having from 6 to 30 carbon atoms or a substituted or unsubstituted heteroaryl group having from 2 to 30 carbon atoms. $Y^{S1}$ and $Y^{S2}$ each independently represent a substituted or unsubstituted alkylene group having from 1 to 30 carbon atoms or a substituted or unsubstituted arylene group having from 6 to 30 carbon atoms. n and m each independently represent an integer of from 0 to 5.)

The general formula (Sa-1) is described.

In the general formula (Sa-1), X represents a substituted or unsubstituted alkylene group having from 1 to 30 carbon atoms, a substituted or unsubstituted alkenylene group having from 2 to 30 carbon atoms, a substituted or unsubstituted arylene group having from 6 to 30 carbon atoms, a substituted or unsubstituted heteroarylene group having from 2 to 30 carbon atoms, or a substituted or unsubstituted heterocyclic group having from 2 to 30 carbon atoms, or a group formed by a combination of these groups. X is preferably a substituted or unsubstituted arylene group having from 6 to 30 carbon atoms, more preferably a substituted or unsubstituted phenylene, a substituted or unsubstituted biphenylene, and a substituted or unsubstituted naphthylene, and still more preferably a substituted or unsubstituted biphenylene.

$R^{S1}$, $R^{S2}$, and $R^{S3}$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, a substituted or unsubstituted fused polycyclic group having from 5 to 30 carbon atoms, a hydroxyl group, a cyano group, or a substituted or unsubstituted amino group. Adjacent $R^{S1}$, $R^{S2}$, and $R^{S3}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S1}$, $R^{S2}$, and $R^{S3}$ are preferably a hydrogen atom, a substituted or unsubstituted alkyl group having from 1 to 30 carbon atoms, a substituted or unsubstituted aryl group having from 6 to 30 carbon atoms, a substituted or unsubstituted fused polycyclic group having from 5 to 30 carbon atoms, or a cyano group, and more preferably a hydrogen atom.

$Ar^{S1}$ and $Ar^{S2}$ each independently represent a substituted or unsubstituted aryl group having from 6 to 30 carbon atoms, or a substituted or unsubstituted heteroaryl group having from 2 to 30 carbon atoms. $Ar^{S1}$ and $Ar^{S2}$ are preferably a substituted or unsubstituted phenyl group.

Next, the general formula (Sb-1) is described.

In the general formula (Sb-1), $R^{S4}$, $R^{S5}$, $R^{S6}$ and $R^{S7}$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, or a substituted or unsubstituted fused polycyclic group having from 5 to 30 carbon atoms, a hydroxyl group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S4}$, $R^{S5}$, $R^{S6}$ and $R^{S7}$ are preferably a hydrogen atom, a substituted or unsubstituted alkyl group having from 1 to 30 carbon atoms, a substituted or unsubstituted aryl group having from 6 to 30 carbon atoms, a substituted or unsubstituted fused polycyclic group having from 5 to 30 carbon atoms, or a cyano group, and more preferably a hydrogen atom.

$Ar^{S3}$ represents a substituted or unsubstituted aryl group having from 6 to 30 carbon atoms or a substituted or unsubstituted heteroaryl group having from 2 to 30 carbon atoms. $Ar^{S3}$ is preferably a substituted or unsubstituted phenyl group.

Next, the general formula (Sc-1) is described.

In the general formula (Sc-1), $R^{S8}$ and $R^{S9}$ each independently represent a hydrogen atom, a substituted or unsubstituted alkyl group having from 1 to 30 carbon atoms, a substituted or unsubstituted aryl group having from 6 to 30 carbon atoms, a substituted or unsubstituted heterocyclic group having from 2 to carbon atoms, or a substituted or unsubstituted fused polycyclic group having from 5 to 30 carbon atoms. $R^{S8}$ and $R^{S9}$ are preferably a substituted or unsubstituted alkyl group having from 1 to 30 carbon atoms or a substituted or unsubstituted aryl group having from 6 to 30 carbon atoms, and more preferably a methyl group or a phenyl group. $R^{S10}$ is a substituted or unsubstituted alkyl group having from 1 to 30 carbon atoms, a substituted or unsubstituted aryl group having from 6 to 30 carbon atoms, a substituted or unsubstituted heterocyclic group having from 2 to carbon atoms, or a substituted or unsubstituted fused polycyclic group having from 5 to 30 carbon atoms. $R^{S10}$ is preferably a substituted or unsubstituted aryl group having from 6 to 30 carbon atoms, and more preferably a phenyl group. $R^{S11}$ and $R^{S12}$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, a substituted or unsubstituted fused polycyclic group having from 5 to 30 carbon atoms, a hydroxyl group, a cyano group, or a substituted or unsubstituted amino group. Adjacent $R^{S11}$ and $R^{S12}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S11}$ and $R^{S12}$ are preferably a hydrogen atom, a substituted or unsubstituted alkyl group having from 1 to 30 carbon atoms, a substituted or unsubstituted aryl group having from 6 to 30 carbon atoms, a substituted or unsubstituted fused polycyclic group having from 5 to 30 carbon atoms, or a cyano group, and more preferably a hydrogen atom. $Ar^{S4}$ represents a substituted or unsubstituted aryl group having from 6 to 30 carbon atoms or a substituted or unsubstituted heteroaryl group having from 2 to 30 carbon atoms. $Y^{S1}$ and $Y^{S2}$ represent a substituted or unsubstituted alkylene group having from 1 to 30 carbon atoms or a substituted or unsubstituted arylene group having from 6 to 30 carbon atoms. $Y^{S1}$ and $Y^{S2}$ are preferably a substituted or unsubstituted arylene group having from 6 to 30 carbon atoms, and more preferably a substituted or unsubstituted phenylene group. n is an integer of from 0 to 5, preferably from 0 to 3, more preferably from 0 to 2, and still more preferably 0. m is an integer of from 0 to 5, preferably from 0 to 3, more preferably from 0 to 2, and still more preferably 1.

The compound represented by the general formula (Sa-1) is preferably a compound represented by the following general formula (Sa-2).

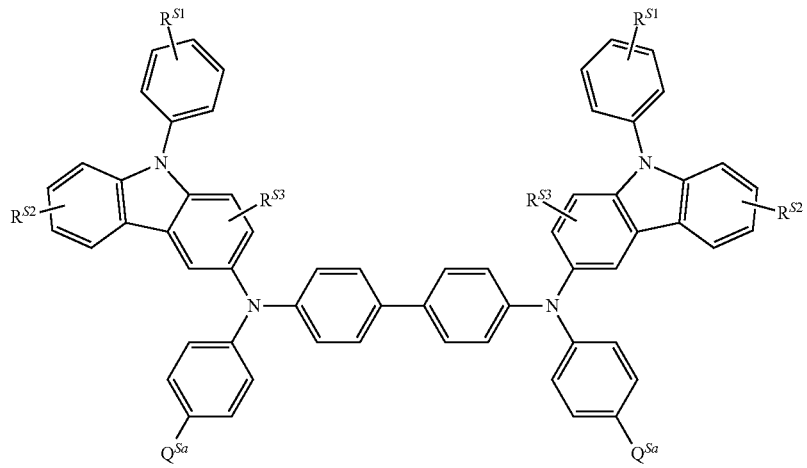

General Formula (Sa-2)

(In the formula, $R^{S1}$, $R^{S2}$, $R^{S3}$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, a substituted or unsubstituted fused polycyclic group having from 5 to 30 carbon atoms, a hydroxyl group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Q^{Sa}$s each independently represent a hydrogen atom, a cyano group, a fluorine atom, an alkoxy group having from 1 to 30 carbon atoms, a substituted or unsubstituted alkyl group having from 1 to 30 carbon atoms, an aryloxy group having from 6 to 30 carbon atoms, a substituted or unsubstituted aryl group having from 6 to 30 carbon atoms, a substituted or unsubstituted heterocyclic ring having from 2 to 30 carbon atoms, or a substituted or unsubstituted amino group.)

The general formula (Sa-2) is described. $R^{S1}$, $R^{S2}$ and $R^{S3}$ are synonymous with those in the general formula (Sa-1), and preferred ranges thereof are also the same. Each $Q^{Sa}$ represents a hydrogen atom, a cyano group, a fluorine atom, an alkoxy group having from 1 to 30 carbon atoms, a substituted or unsubstituted alkyl group having from 1 to 30 carbon atoms, an aryloxy group having from 6 to 30 carbon atoms, a substituted or unsubstituted aryl group having from 6 to 30 carbon atoms, a substituted or unsubstituted heterocyclic ring having from 2 to 30 carbon atoms, or a substituted or unsubstituted amino group. $Q^{Sa}$ is preferably a hydrogen atom, a cyano group, a fluorine atom, a substituted or unsubstituted alkyl group having from 1 to 30 carbon atoms, or a substituted or unsubstituted aryl group having from 6 to 30 carbon atoms, more preferably a hydrogen atom or a substituted or unsubstituted alkyl group having from 1 to 30 carbon atoms, and still more preferably a hydrogen atom.

The compound represented by the general formula (Sb-1) is preferably a compound represented by the following general formula (Sb-2).

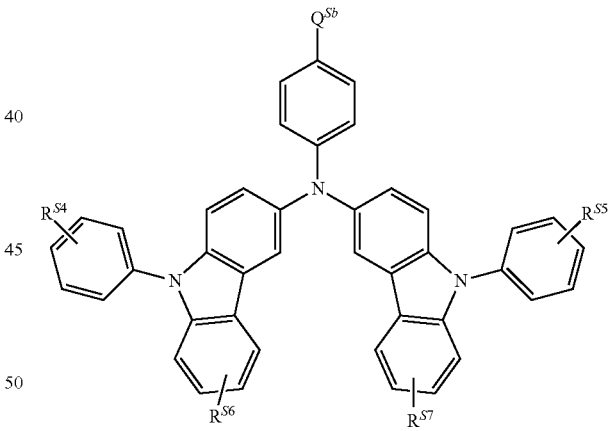

General Formula (Sb-2)

(In the formula, $R^{S4}$, $R^{S5}$, $R^{S6}$, and $R^{S7}$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, a substituted or unsubstituted fused polycyclic group having from 5 to 30 carbon atoms, a hydroxyl group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Q^{Sb}$ represents a hydrogen atom, a cyano group, a fluorine atom, an alkoxy group having from 1 to 30 carbon atoms, a substituted or unsubstituted alkyl group having from 1 to 30 carbon atoms, an aryloxy group having from 6 to 30 carbon atoms, a substituted or unsubstituted aryl group having from 6 to 30 carbon atoms, a substituted or unsubstituted heterocyclic ring having from 2 to 30 carbon atoms, or a substituted or unsubstituted amino group.)

The general formula (Sb-2) is described. $R^{S4}$, $R^{S5}$, $R^{S6}$, and $R^{S7}$ are synonymous with those in the general formula (Sb-1), and preferred ranges thereof are also the same. $Q^{Sb}$ represents a hydrogen atom, a cyano group, a fluorine atom, an alkoxy group having from 1 to 30 carbon atoms, a substituted or unsubstituted alkyl group having from 1 to 30 carbon atoms, an aryloxy group having from 6 to 30 carbon atoms, a substituted or unsubstituted aryl group having from 6 to 30 carbon atoms, a substituted or unsubstituted heterocyclic ring having from 2 to 30 carbon atoms, or a substituted or unsubstituted amino group. $Q^{Sb}$ is preferably a hydrogen atom, a cyano group, a fluorine atom, a substituted or unsubstituted alkyl group having from 1 to 30 carbon atoms, or a substituted or unsubstituted aryl group having from 6 to 30 carbon atoms, more preferably a hydrogen atom or a substituted or unsubstituted alkyl group having from 1 to 30 carbon atoms, and still more preferably a hydrogen atom.

The compound represented by the general formula (Sc-1) is preferably a compound represented by the following general formula (Sc-2).

General Formula (Sc-2)

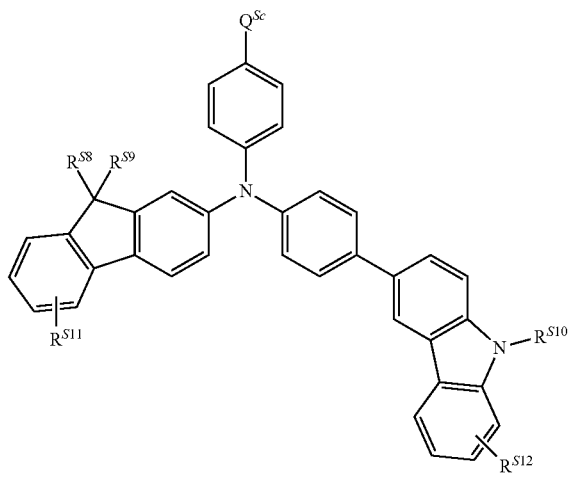

(In the formula, $R^{S8}$ and $R^{S9}$ each independently represent a hydrogen atom, a substituted or unsubstituted alkyl group having from 1 to 30 carbon atoms, a substituted or unsubstituted aryl group having from 6 to 30 carbon atoms, a substituted or unsubstituted heterocyclic group having from 2 to 30 carbon atoms, or a substituted or unsubstituted fused polycyclic group having from 5 to 30 carbon atoms. $R^{S10}$ represents a substituted or unsubstituted alkyl group having from 1 to 30 carbon atoms, a substituted or unsubstituted aryl group having from 6 to 30 carbon atoms, a substituted or unsubstituted heterocyclic group having from 2 to 30 carbon atoms, or a substituted or unsubstituted fused polycyclic group having from 5 to 30 carbon atoms. $R^{S11}$ and $R^{S12}$ each independently represent a hydrogen atom, a substituted or unsubstituted alkyl group having from 1 to 30 carbon atoms, a substituted or unsubstituted alkoxy group having from 1 to 30 carbon atoms, a substituted or unsubstituted aryl group having from 6 to 30 carbon atoms, a substituted or unsubstituted aryloxy group having from 6 to 30 carbon atoms, a substituted or unsubstituted heterocyclic ring having from 2 to 30 carbon atoms, a substituted or unsubstituted fused polycyclic group having from 5 to 30 carbon atoms, a hydroxyl group, a cyano group, or a substituted or unsubstituted amino group. Adjacent $R^{S11}$ and $R^{S12}$ may be bonded to each other to form a saturated carbocycle or an unsaturated carbocycle. $Q^{Sc}$ represents a hydrogen atom, a cyano group, a fluorine atom, an alkoxy group having from 1 to 30 carbon atoms, a substituted or unsubstituted alkyl group having from 1 to 30 carbon atoms, an aryloxy group having from 6 to 30 carbon atoms, a substituted or unsubstituted aryl group having from 6 to 30 carbon atoms, a substituted or unsubstituted heterocyclic ring having from 2 to 30 carbon atoms, or a substituted or unsubstituted amino group.)

The general formula (Sc-2) is described. $R^{S8}$, $R^{S9}$, $R^{S10}$, $R^{S11}$, and $R^{S12}$ are synonymous with those in the general formula (Sc-1), and preferred ranges thereof are also the same. $Q^{Sc}$ represents a hydrogen atom, a cyano group, a fluorine atom, an alkoxy group having from 1 to 30 carbon atoms, a substituted or unsubstituted alkyl group having from 1 to 30 carbon atoms, an aryloxy group having from 6 to 30 carbon atoms, a substituted or unsubstituted aryl group having from 6 to 30 carbon atoms, a substituted or unsubstituted heterocyclic ring having from 2 to 30 carbon atoms, or a substituted or unsubstituted amino group. $Q^{Sc}$ is preferably a hydrogen atom, a cyano group, a fluorine atom, a substituted or unsubstituted alkyl group having from 1 to 30 carbon atoms, or a substituted or unsubstituted aryl group having from 6 to 30 carbon atoms, more preferably a hydrogen atom or a substituted or unsubstituted aryl group having from 6 to 30 carbon atoms, and still more preferably a phenyl group.

Specific examples of the compounds represented by the general formulae (Sa-1), (Sb-1), and (Sc-1) include those described below. However, it should not be construed that the present invention is limited to the following specific examples.

1

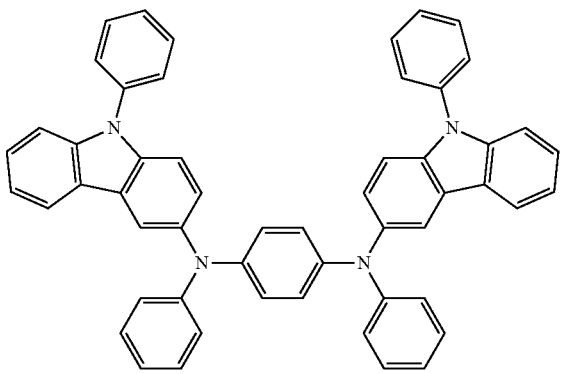

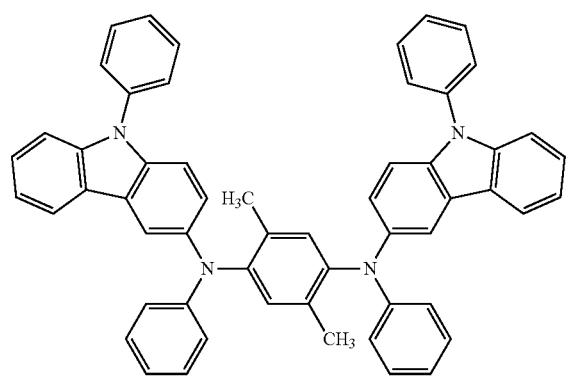
2
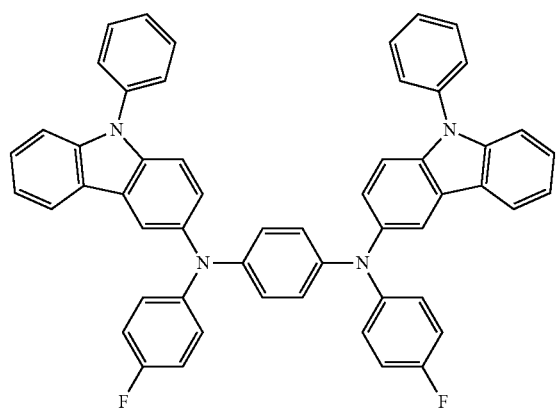
5
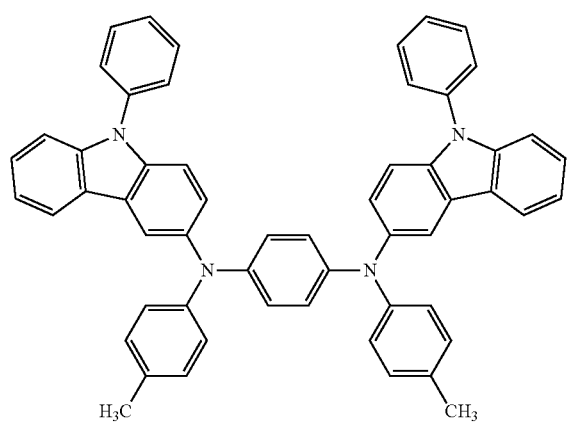
3
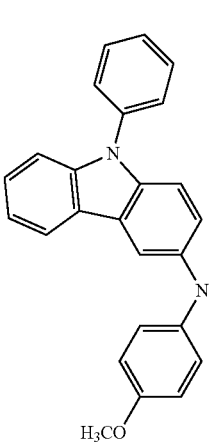
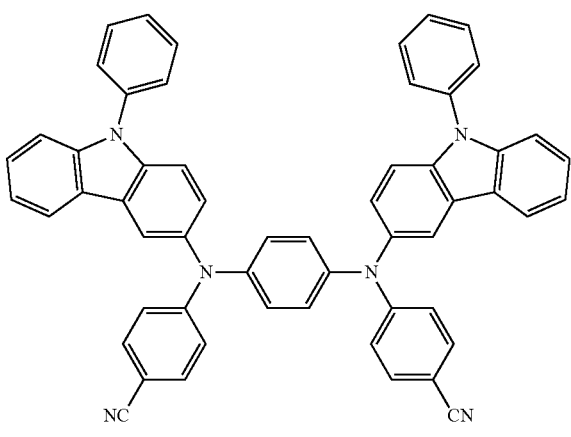
4
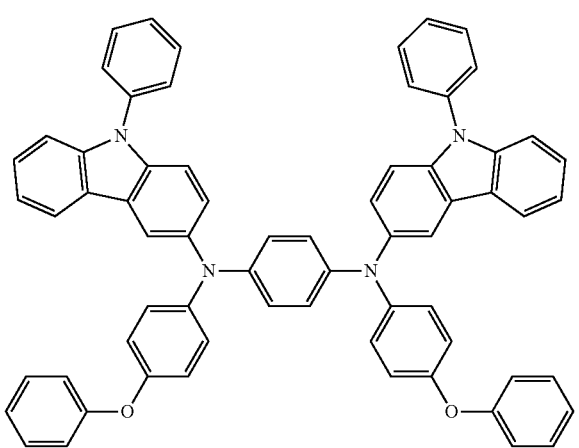
6
7

69
-continued
8
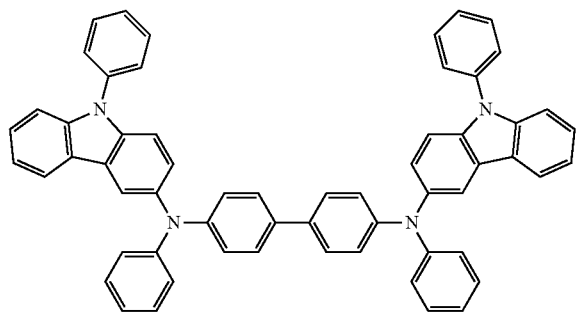
9
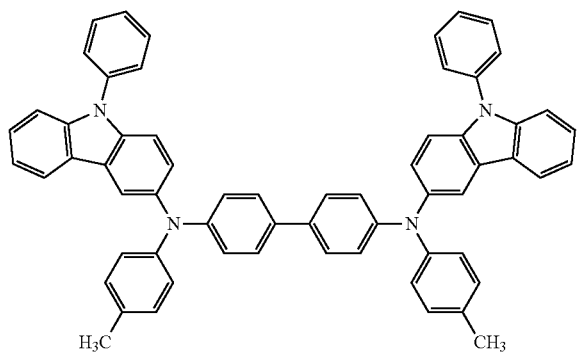
10
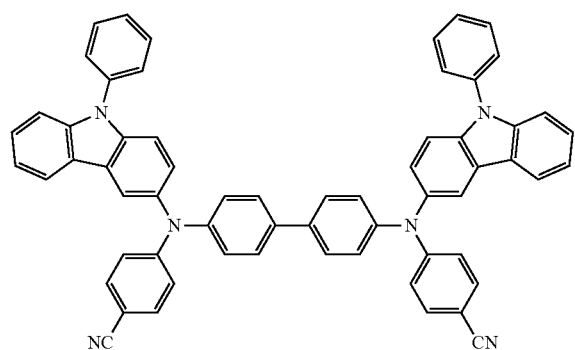
11
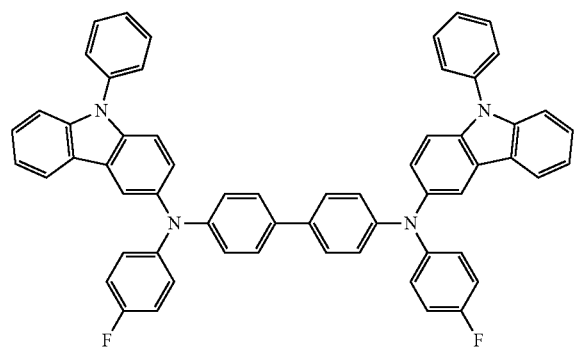
70
-continued
12
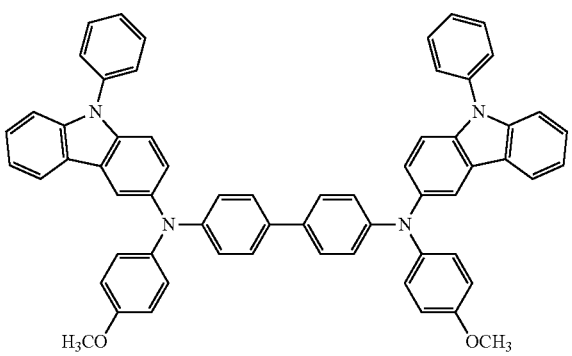
13
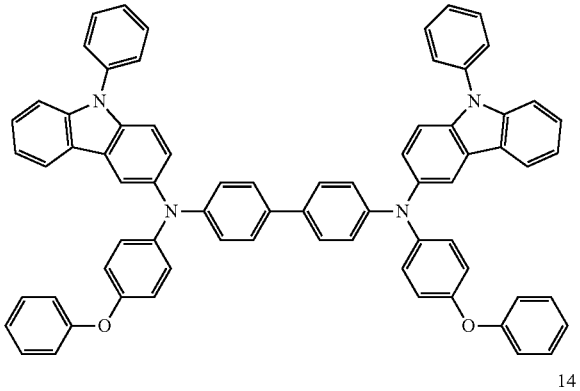
14
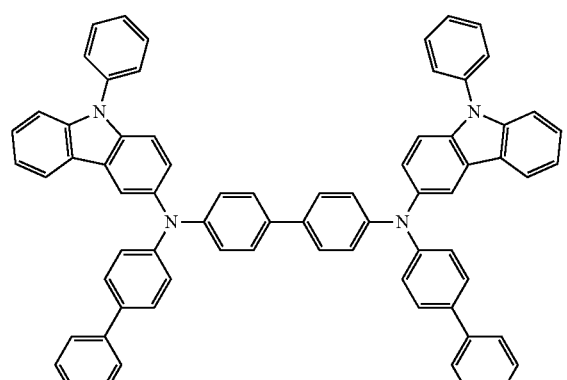
15
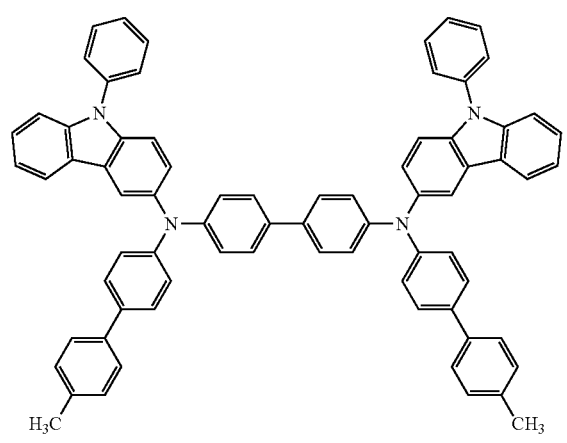

16
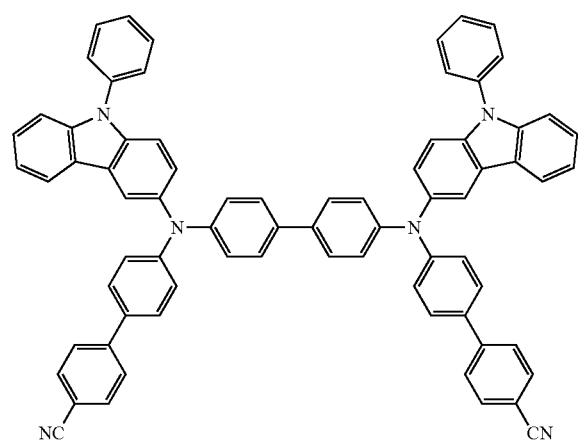
19
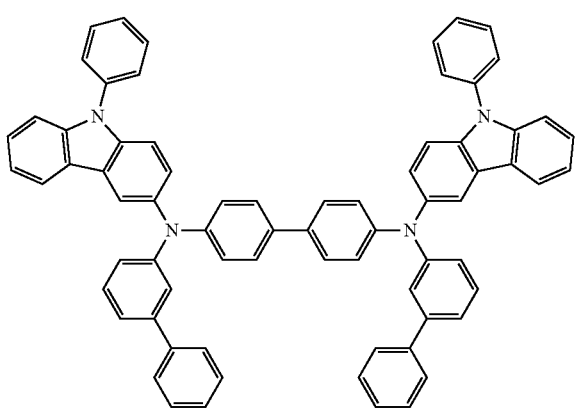
17
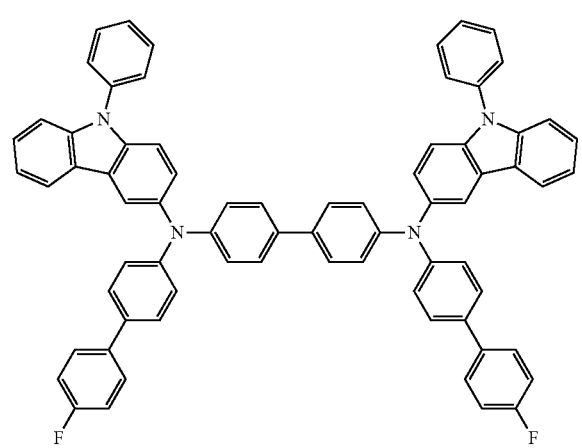
20
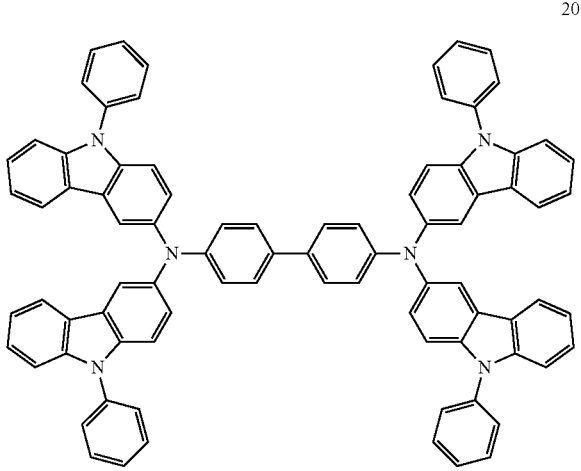
18
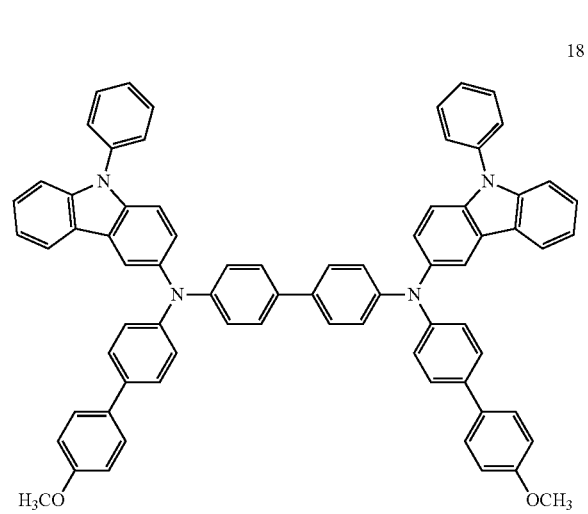
21
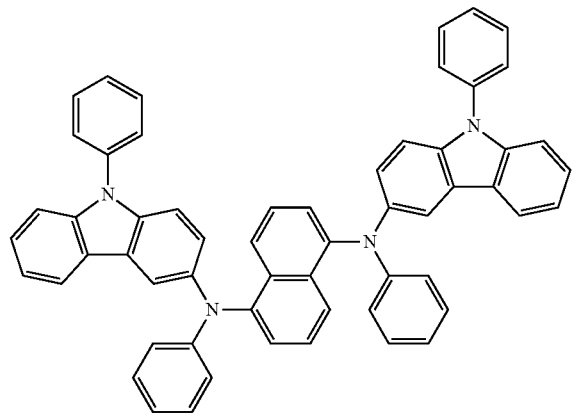

-continued
22
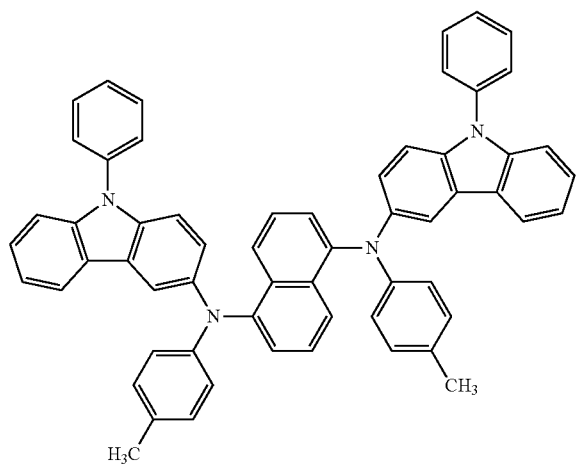
23
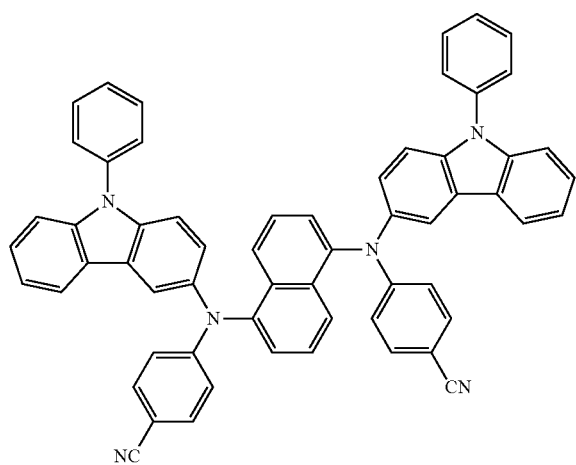
24
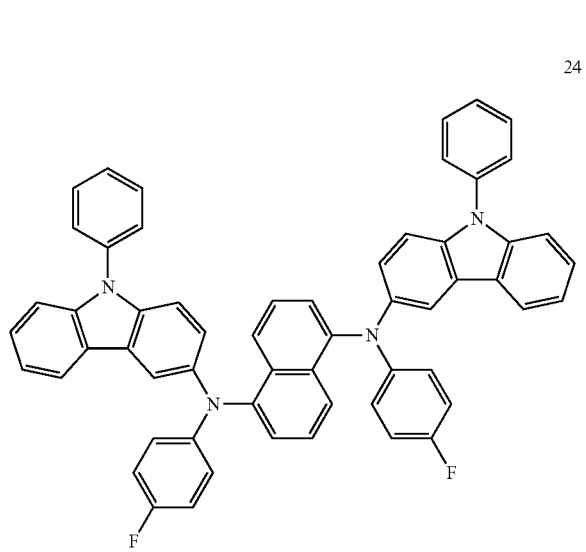
-continued
25
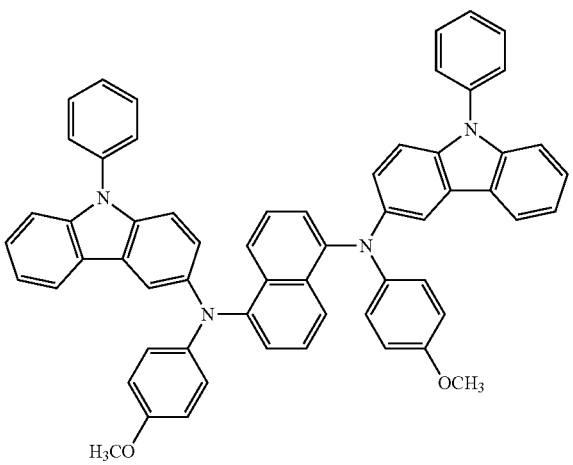
26
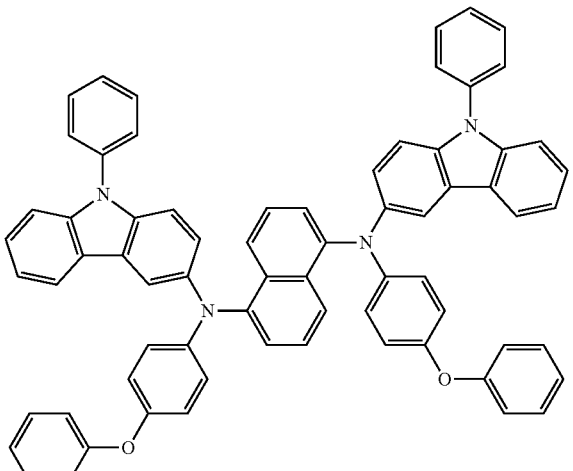
27

28
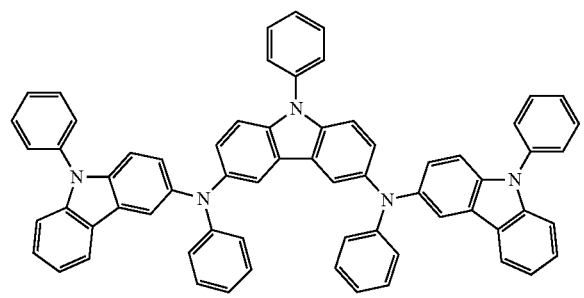
29
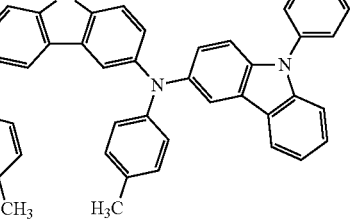
31
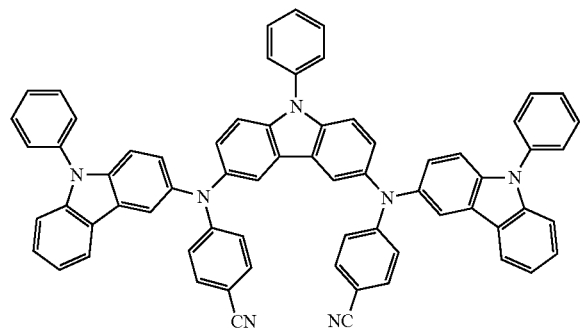
32
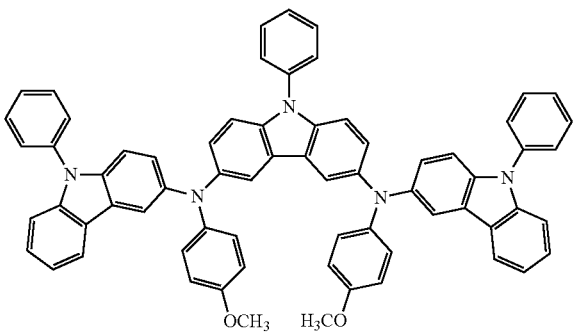
33
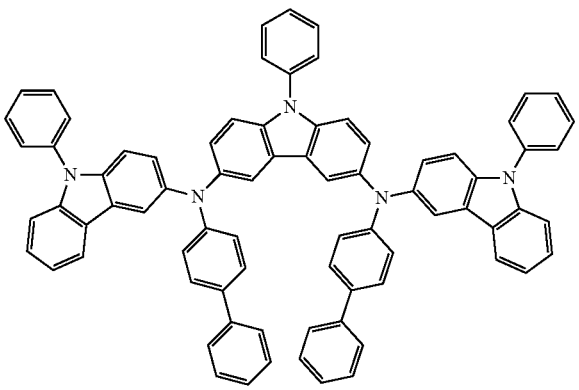
34
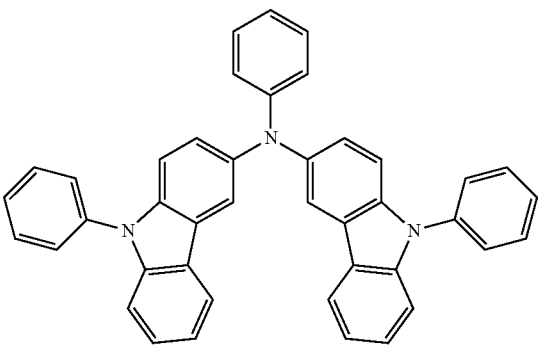
35
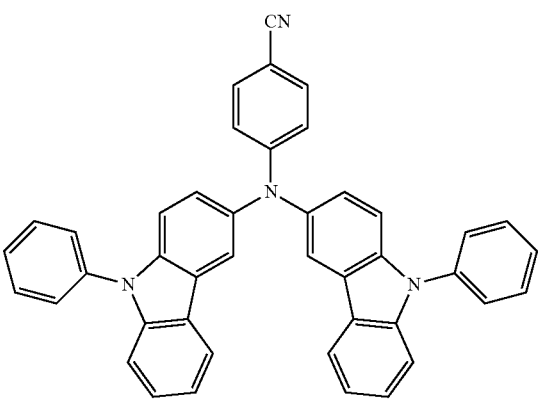

36
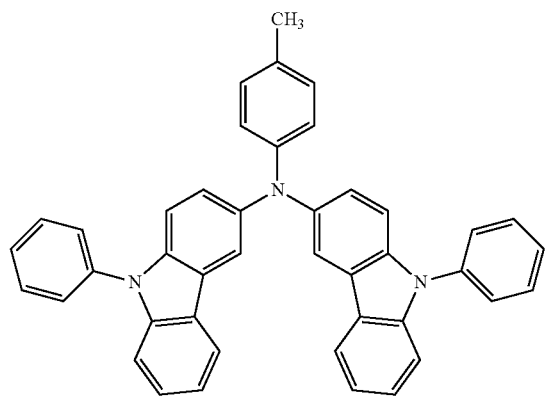
37
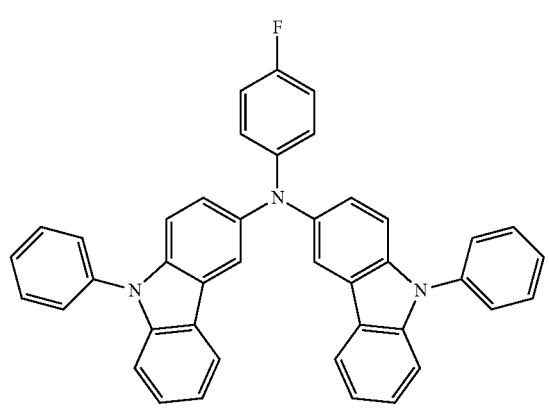
38
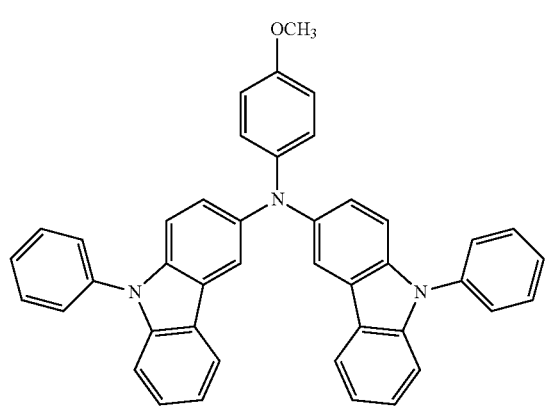
39
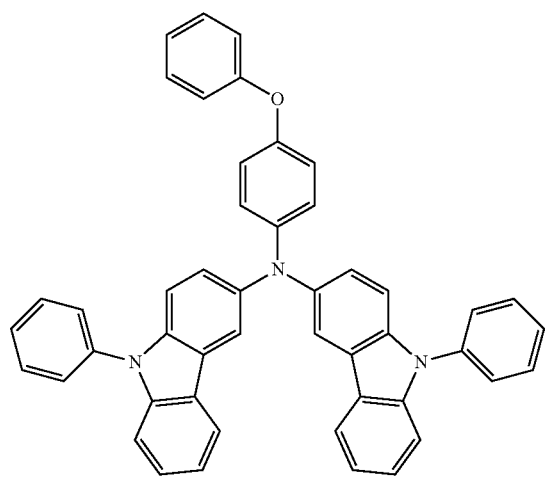
40
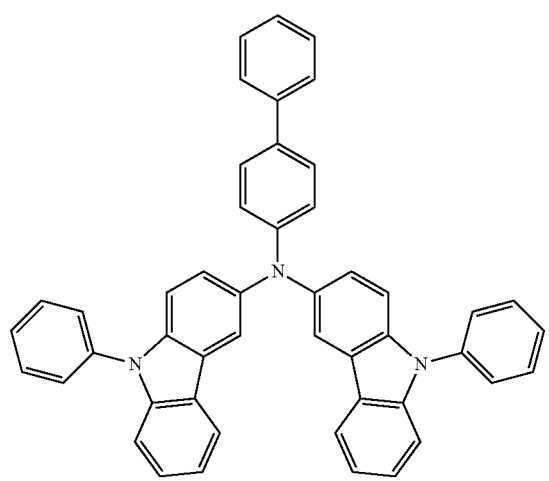
41
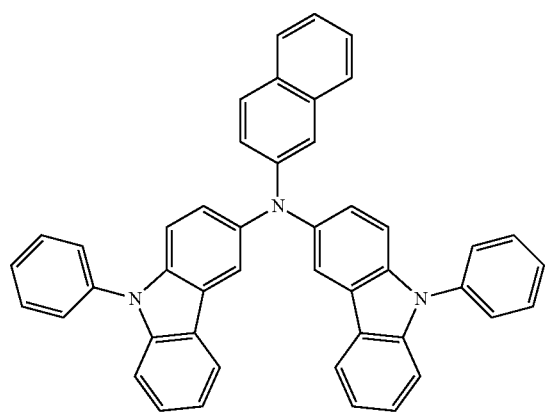

42
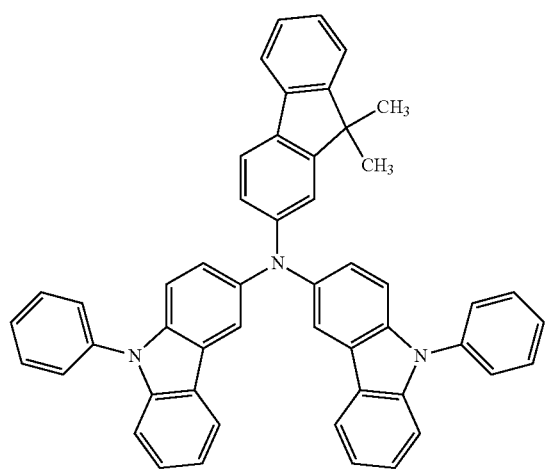
43
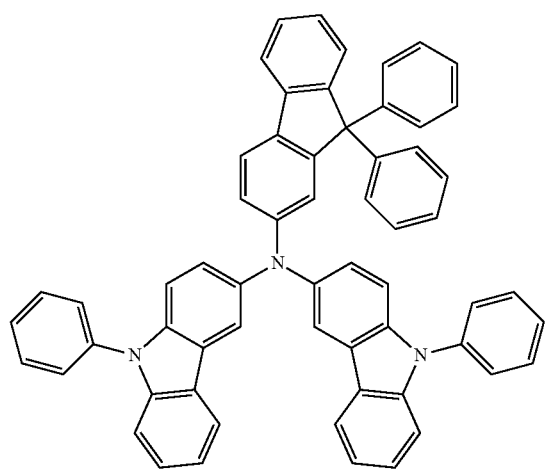
44
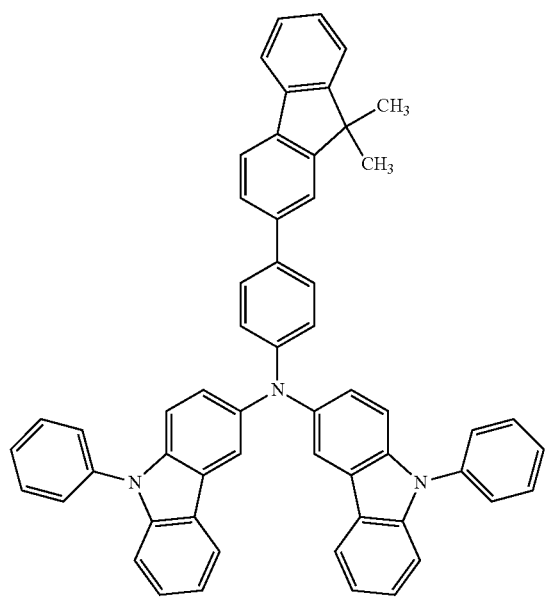
45
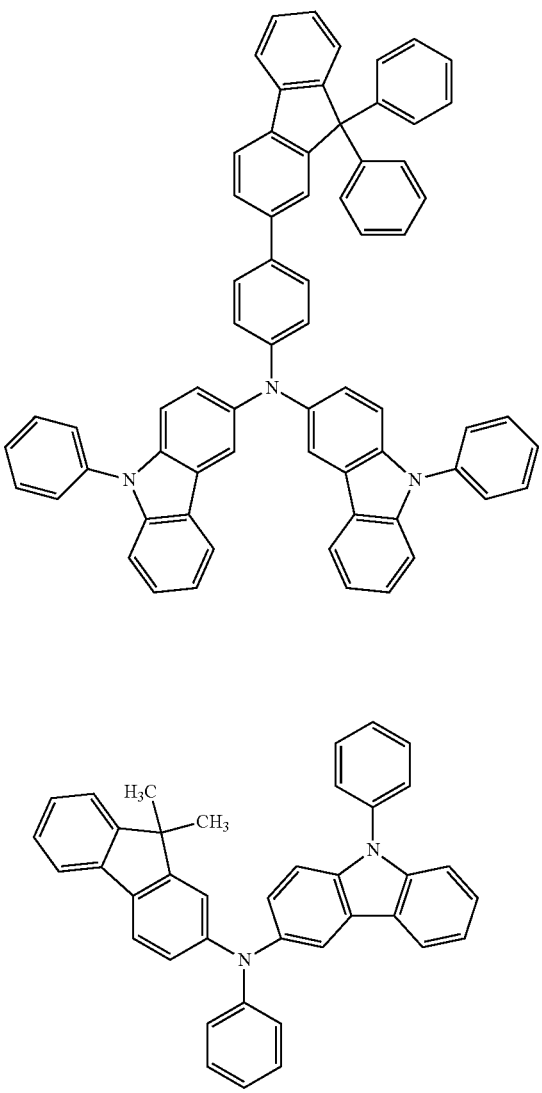
46
47
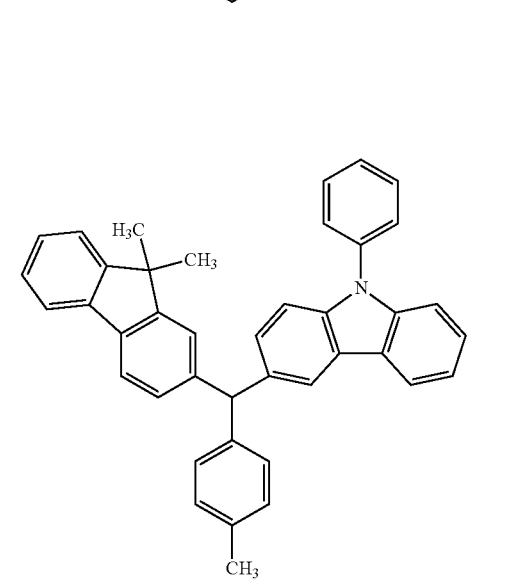

48
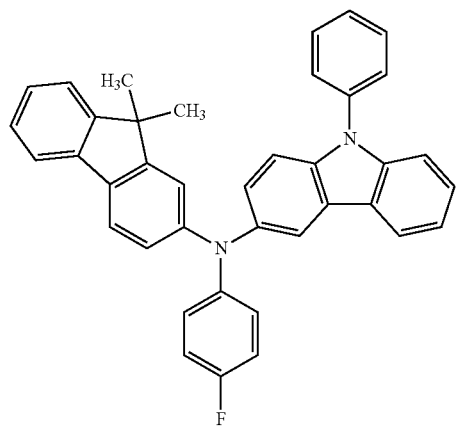
49
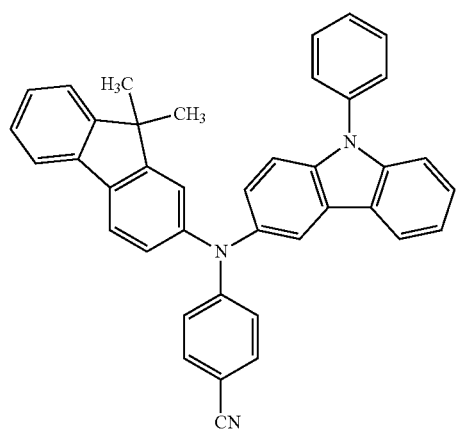
50
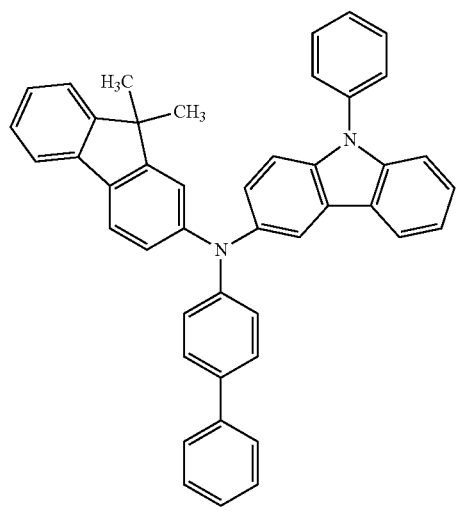
51
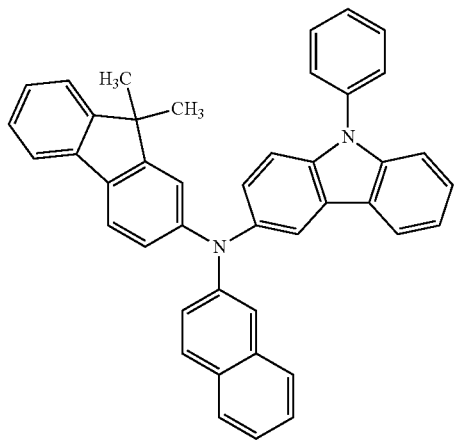
52
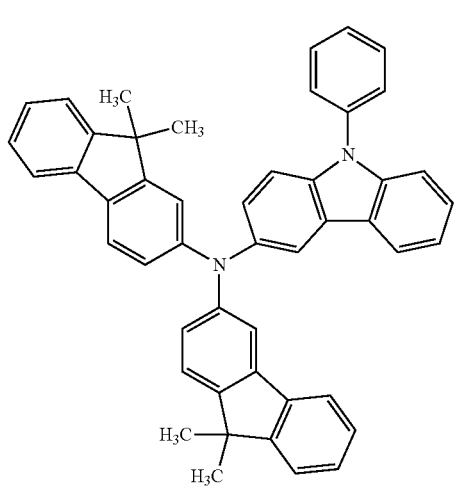
53
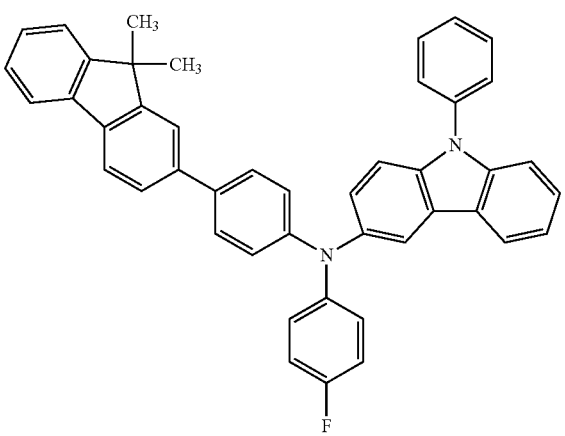

54
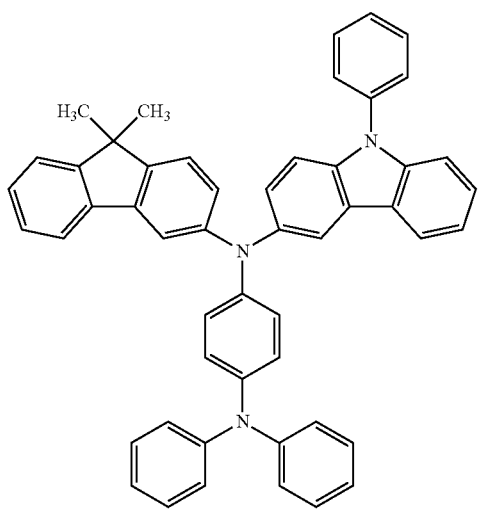
55
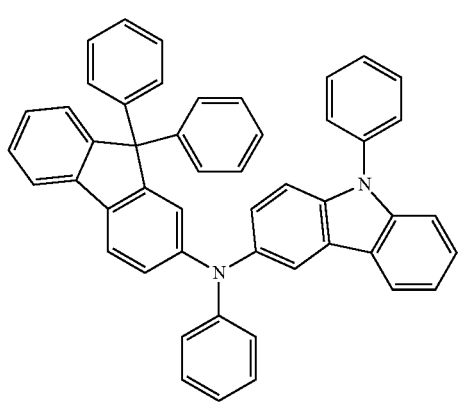
56
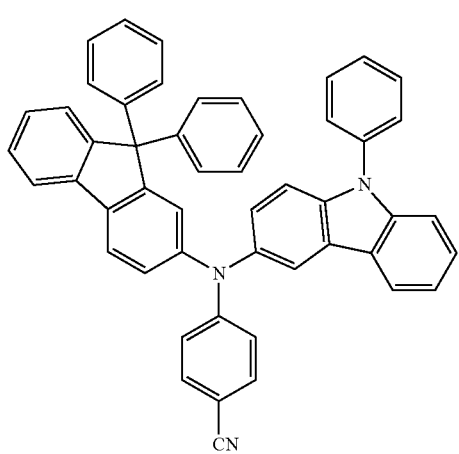
57
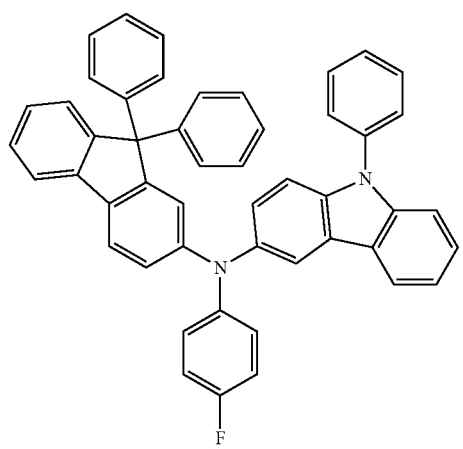
58
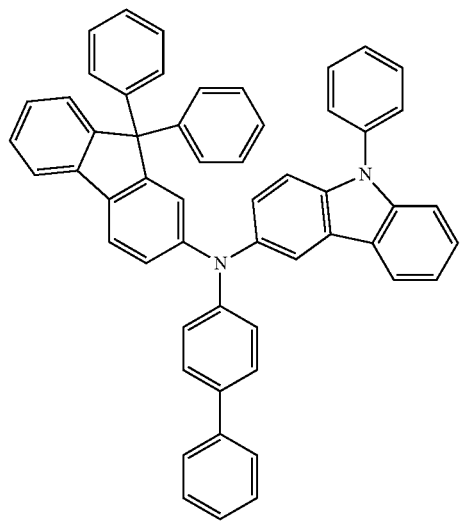
59
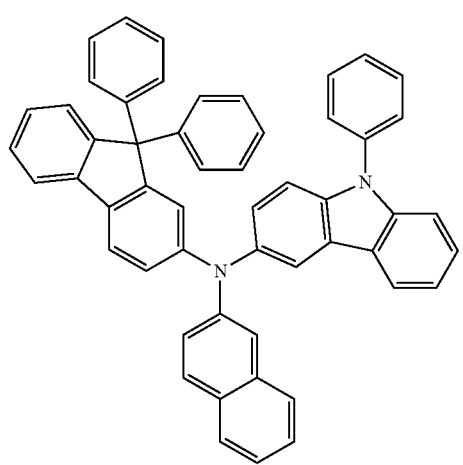

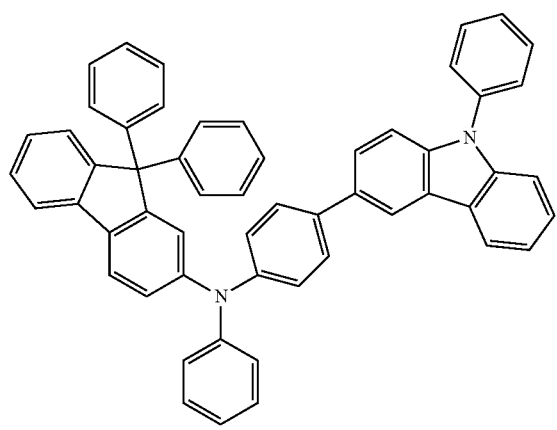
60

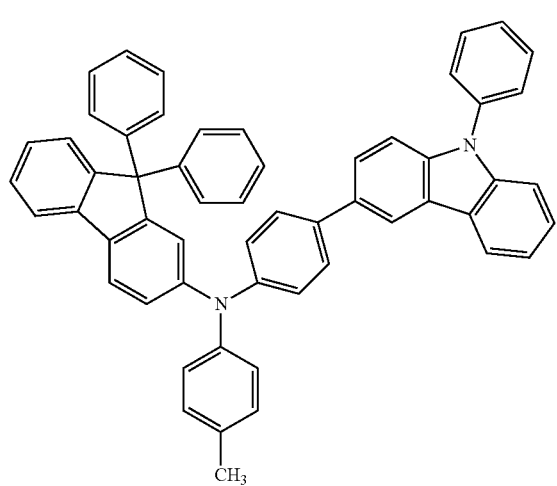
61

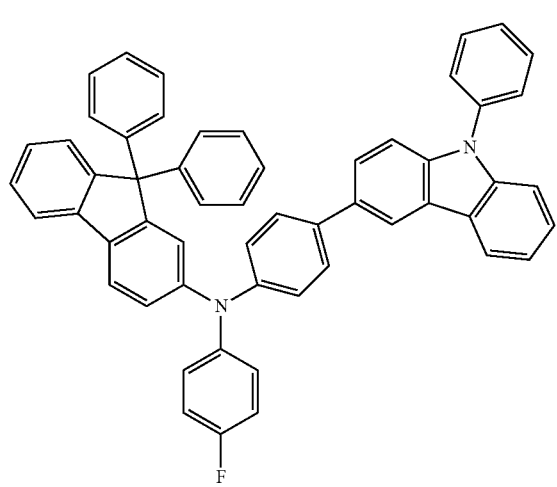
62

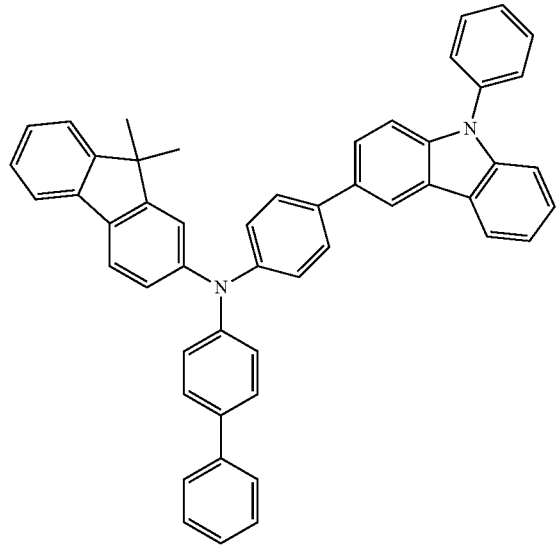
63

The compound represented by the general formula (Sa-1), (Sb-1), or (Sc-1) can be synthesized by the method described in JP-A-2007-318101. After the synthesis, it is preferable that after performing purification by means of column chromatography, recrystallization, reprecipitation, or the like, purification is performed by means of sublimation purification. According to the sublimation purification, not only organic impurities can be separated, but inorganic salts, residual solvent, moisture, and the like can be effectively removed.

In the light emitting element according to the present invention, the compound represented by the general formula (Sa-1), (Sb-1), or (Sc-1) is preferably included in the organic layer between the light emitting layer and the anode. Above all, it is more preferably included in the layer on the anode side adjacent to the light emitting layer, and it is especially preferably a hole transporting material included in the hole transporting layer.

The compound represented by the general formula (Sc-1), (Sb-1), or (Sc-1) is preferably included in the amount of from 70 to 100% by mass, and more preferably from 85 to 100% by mass relative to the total mass of the organic layer to be added.

[Compound Represented by the General Formula (M-3)]

The organic electroluminescent element according to the present invention is a material which is especially preferably used in the organic layer, preferably disposed between the (A) anode and the light emitting layer, and examples thereof include at least one kind of a compound represented by the following general formula (M-3).

The compound represented by the general formula (M-3) is more preferably contained in the organic layer adjacent to the light emitting layer between the light emitting layer and the anode, but it is not limited in its uses and may be further contained in any of other layers in the organic layer. The layer to which the compound represented by the general formula (M-3) is introduced may be any one or plural layers of a light emitting layer, a hole injecting layer, a hole transporting layer, an electron transporting layer, an electron injecting layer, and a charge blocking layer.

The organic layer adjacent to the light emitting layer between the light emitting layer and the anode, which contains the compound represented by the general formula (M-3), is more preferably an electron blocking layer or a hole transporting layer.

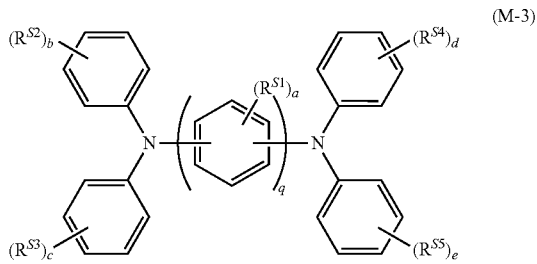

(M-3)

In the general formula (M-3), $R^{S1}$ to $R^{S5}$ each independently represent an alkyl group, a cycloalkyl group, an alkenyl group, an alkynyl group, —CN, a perfluoroalkyl group, a trifluorovinyl group, —$CO_2R$, —C(O)R, —$NR_2$, —$NO_2$, —OR, a halogen atom, an aryl group, or an heteroaryl group, and may also have a substituent Z. Rs each independently represent a hydrogen atom, an alkyl group, a perhaloalkyl group, an alkenyl group, an alkynyl group, a heteroalkyl group, an aryl group, or a heteroaryl group. When plural $R^{S1}$s to $R^{S5}$s are present, they may be bonded to each other to form a ring and may further have a substituent Z.

a represents an integer of from 0 to 4, and when plural $R^{S1}$s are present, they may be the same as or different from each other and may be bonded to each other to form a ring. b to e each independently represent an integer of from 0 to 5, and when each of plural $R^{S2}$s to $R^{S5}$s are present, they may be the same as or different from each other, and any two of them may be bonded to each other to form a ring.

q is an integer of from 1 to 5, and when q is 2 or more, the plural $R^{S1}$s may be the same as or different from each other and may be bonded to each other to form a ring.

The alkyl group may have a substituent and may be saturated or unsaturated. Examples of the group which may be used for substitution include the above-described substituents Z. Examples of the alkyl group represented by $R^{S1}$ to $R^{S5}$ include preferably an alkyl group having from 1 to 8 carbon atoms in total, and more preferably an alkyl group having from 1 to 6 carbon atoms in total, for example, a methyl group, an ethyl group, an isopropyl group, a cyclohexyl group, and a t-butyl group.

The cycloalkyl group may have a substituent and may be saturated or unsaturated. Examples of the group which may be used for substitution include the above-described substituents Z. Examples of the cycloalkyl group represented by $R^{S1}$ to $R^{S5}$ include preferably a cycloalkyl group having the number of ring members of from 4 to 7, and more preferably a cycloalkyl group having from 5 to 6 carbon atoms in total, for example, a cyclopentyl group and a cyclohexyl group.

Examples of the alkenyl group represented by $R^{S1}$ to $R^{S5}$ include those having preferably from 2 to 30 carbon atoms, more preferably from 2 to 20 carbon atoms, and especially preferably from 2 to 10 carbon atoms, for example, vinyl, allyl, 1-propenyl, 1-isopropenyl, 1-butenyl, 2-butenyl, and 3-pentenyl.

Examples of the alkynyl group represented by $R^{S1}$ to $R^{S5}$ include those having preferably from 2 to 30 carbon atoms, more preferably from 2 to 20 carbon atoms, and especially preferably from 2 to 10 carbon atoms, for example, ethynyl, propargyl, 1-propynyl, and 3-pentynyl.

Examples of the perfluoroalkyl group represented by $R^{S1}$ to $R^{S5}$ include those in which all the hydrogen atoms of the above-described alkyl group are substituted with a fluorine atom.

Preferred examples of the aryl group represented by $R^{S1}$ to $R^{S5}$ include a substituted or unsubstituted aryl group having from 6 to 30 carbon atoms, for example, a phenyl group, a tolyl group, a biphenyl group, and a terphenyl group.

The heteroaryl group represented by $R^{S1}$ to $R^{S5}$ is preferably a heteroaryl group having from 5 to 8 carbon atoms, and more preferably a 5- or 6-membered substituted or unsubstituted heteroaryl group. Examples thereof include a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a triazolyl group, a benzothiazolyl group, an isothiazolyl group, a benzisothiazolyl group, a thiadiazolyl group, an isoxazolyl group, a benzisoxazolyl group, a pyrrolidinyl, piperidinyl group, a piperadinyl group, an imidazolidinyl group, a thiazolinyl group, a sulfolanyl group, a carbazolyl group, a dibenzofuryl group, a dibenzothienyl group, and a pyridindolyl group. Preferred examples thereof include a pyridyl group, a pyrimidinyl group, an imidazolyl group, and a thienyl group, with a pyridyl group and a pyrimidinyl group being more preferable.

$R^{S1}$ to $R^{S5}$ are preferably a hydrogen atom, an alkyl group, a cyano group, a trifluoromethyl group, a perfluoroalkyl group, a dialkylamino group, a fluoro group, an aryl group, or a heteroaryl group; more preferably a hydrogen atom, an alkyl group, a cyano group, a trifluoromethyl group, a fluoro group, or an aryl group; and still more preferably a hydrogen atom, an alkyl group, or an aryl group. As the substituent Z, an alkyl group, an alkoxy group, a fluoro group, a cyano group, and a dialkylamino group are preferable, and a hydrogen atom and an alkyl group are more preferable.

Any two of $R^{S1}$ to $R^{S5}$ may be bonded to form a fused 4- to 7-membered ring, and the fused 4- to 7-membered ring is cycloalkyl, aryl, or heteroaryl. The fused 4- to 7-membered ring may further have a substituent Z. The definitions and preferred ranges of the cycloalkyl, aryl, and heteroaryl thus formed are the same as the cycloalkyl group, the aryl group, and the heteroaryl group defined by $R^{S1}$ to $R^{S5}$, respectively.

In the case where the compound represented by the general formula (M-3) is used in the hole transporting layer, the compound represented by the general formula (M-3) is included in the amount of preferably from 50 to 100% by mass, more preferably from 80 to 100% by mass, and especially preferably from 95 to 100% by mass.

In addition, in the case where the compound represented by the general formula (M-3) is used in plural organic layers, the compound is contained in an amount of the above-described range in each layer.

The thickness of the hole transporting layer including the compound represented by the general formula (M-3) is preferably from 1 nm to 500 nm, more preferably from 3 nm to 200 nm, and still more preferably from 5 nm to 100 nm. In addition, the hole transporting layer is preferably provided adjacent to the light emitting layer.

Specific examples of the compound represented by the general formula (M-3) are shown below, but it should not be construed that the present invention is limited thereto.

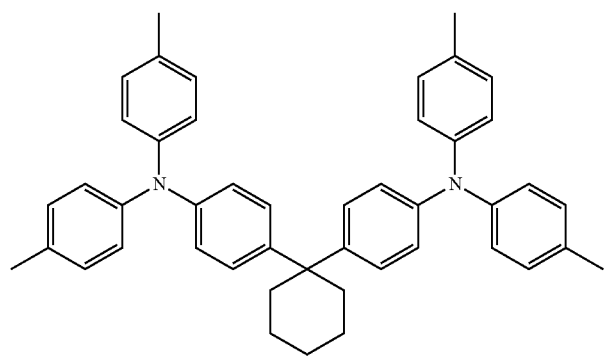
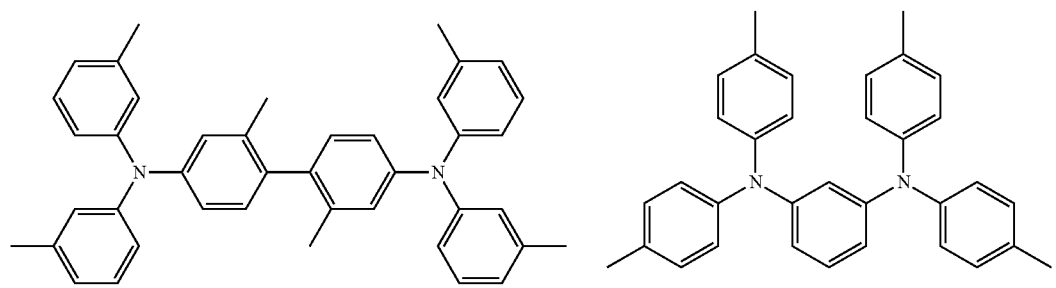
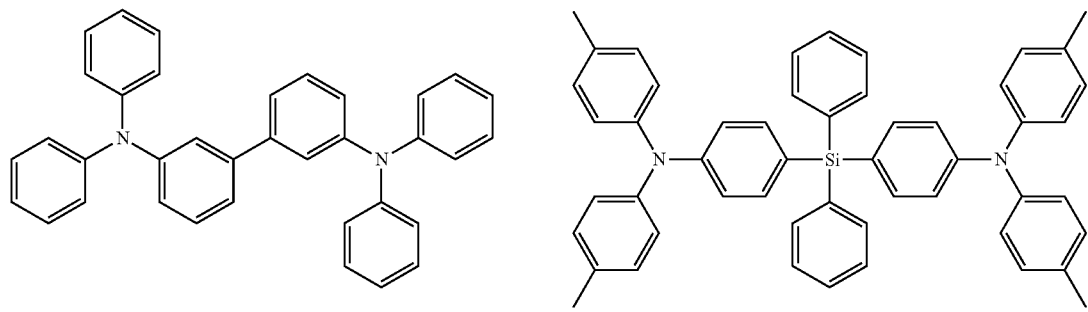
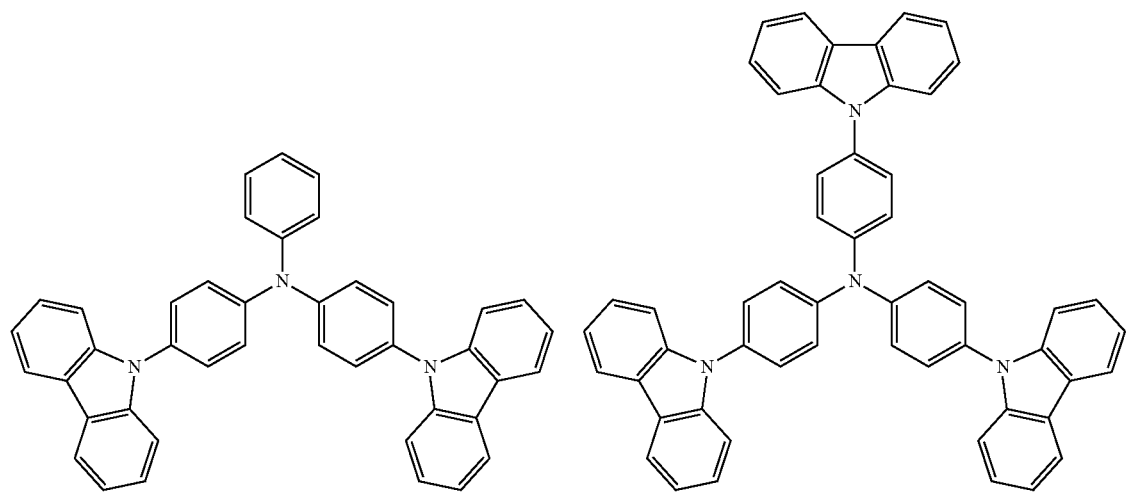

-continued
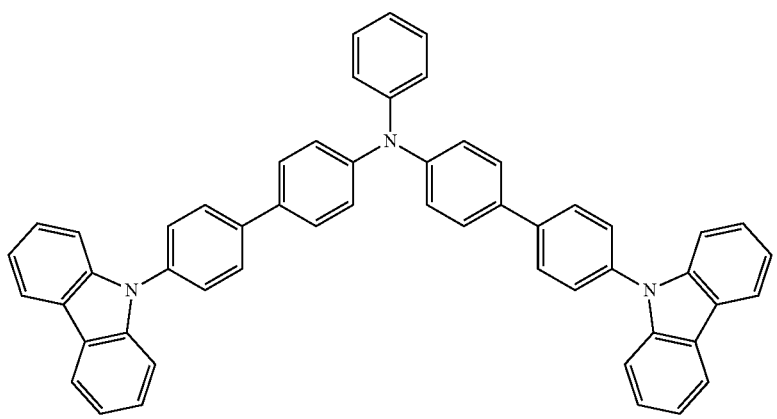
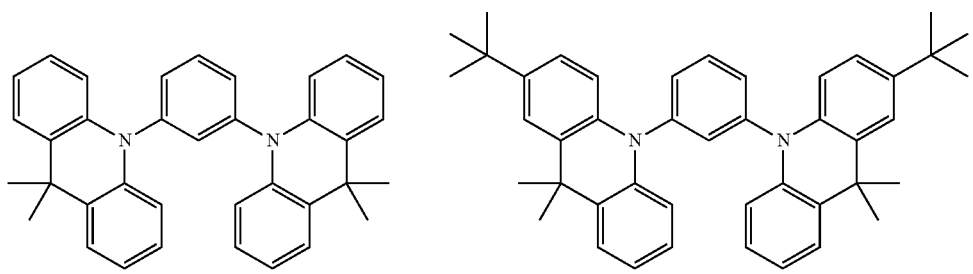
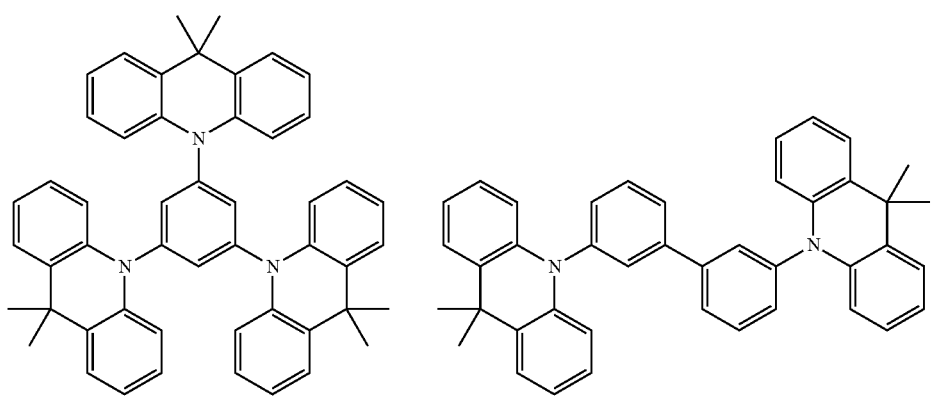
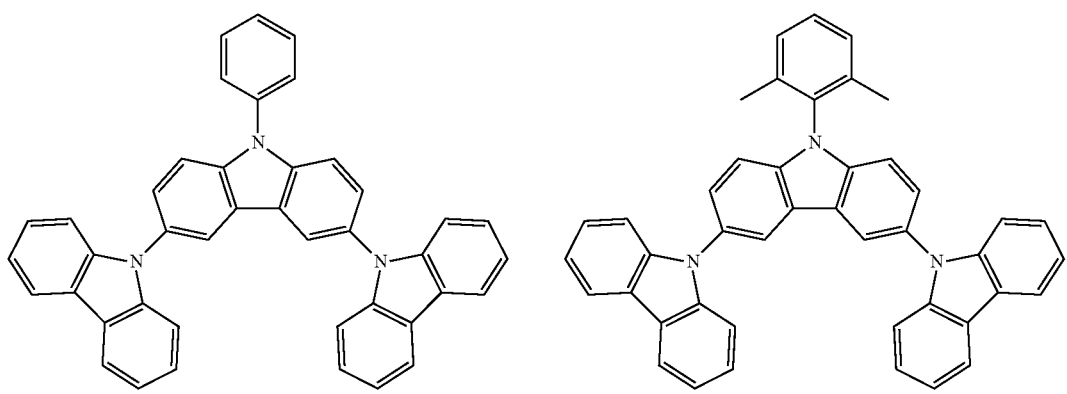

-continued
| 93 | 94 |
|---|---|
| 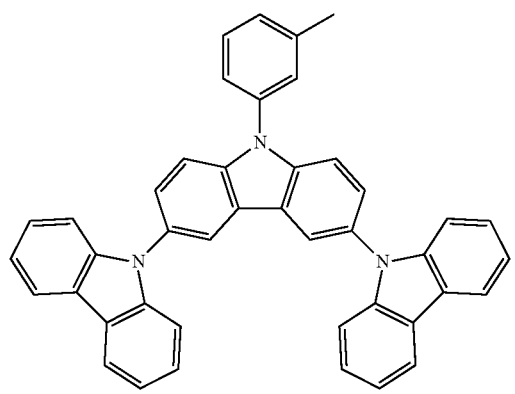 | 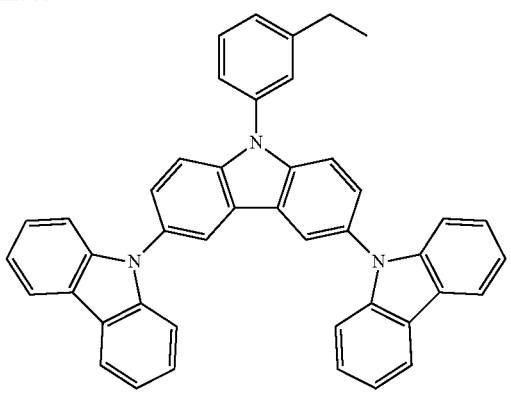 |
| 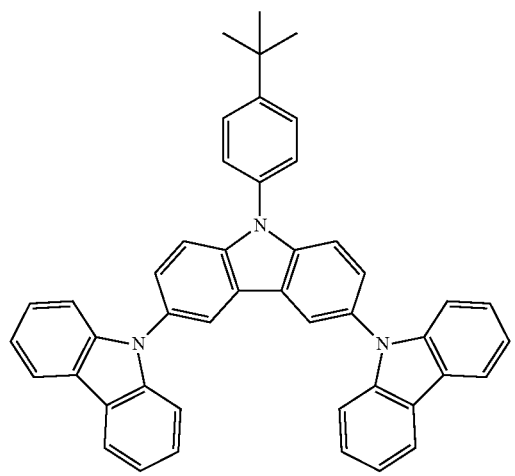 | 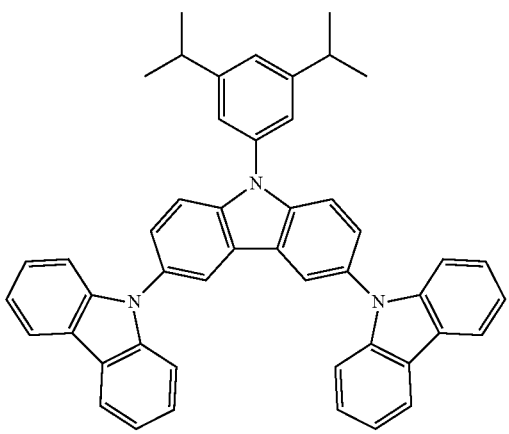 |
| 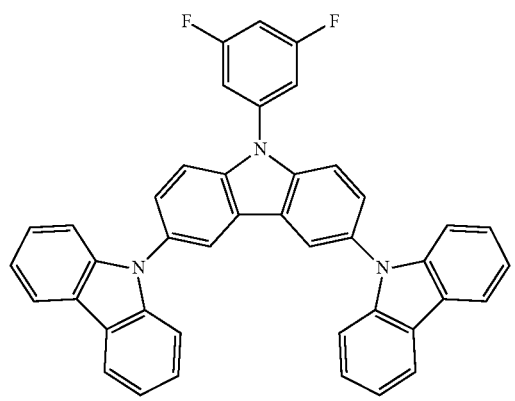 | 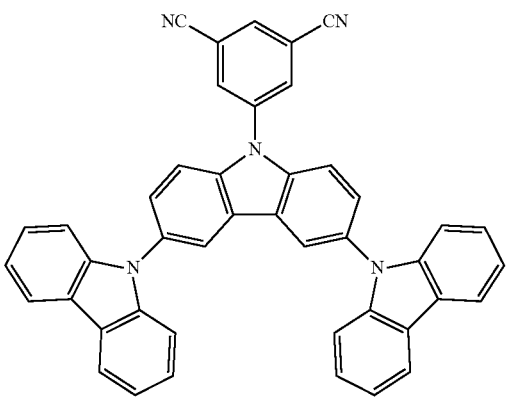 |
| 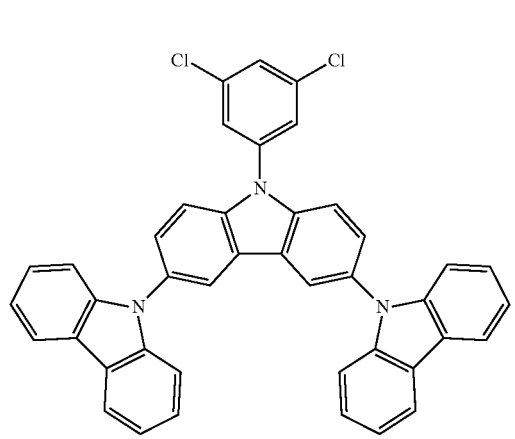 | 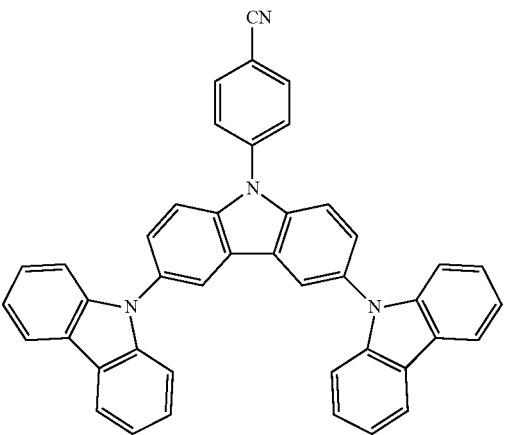 |

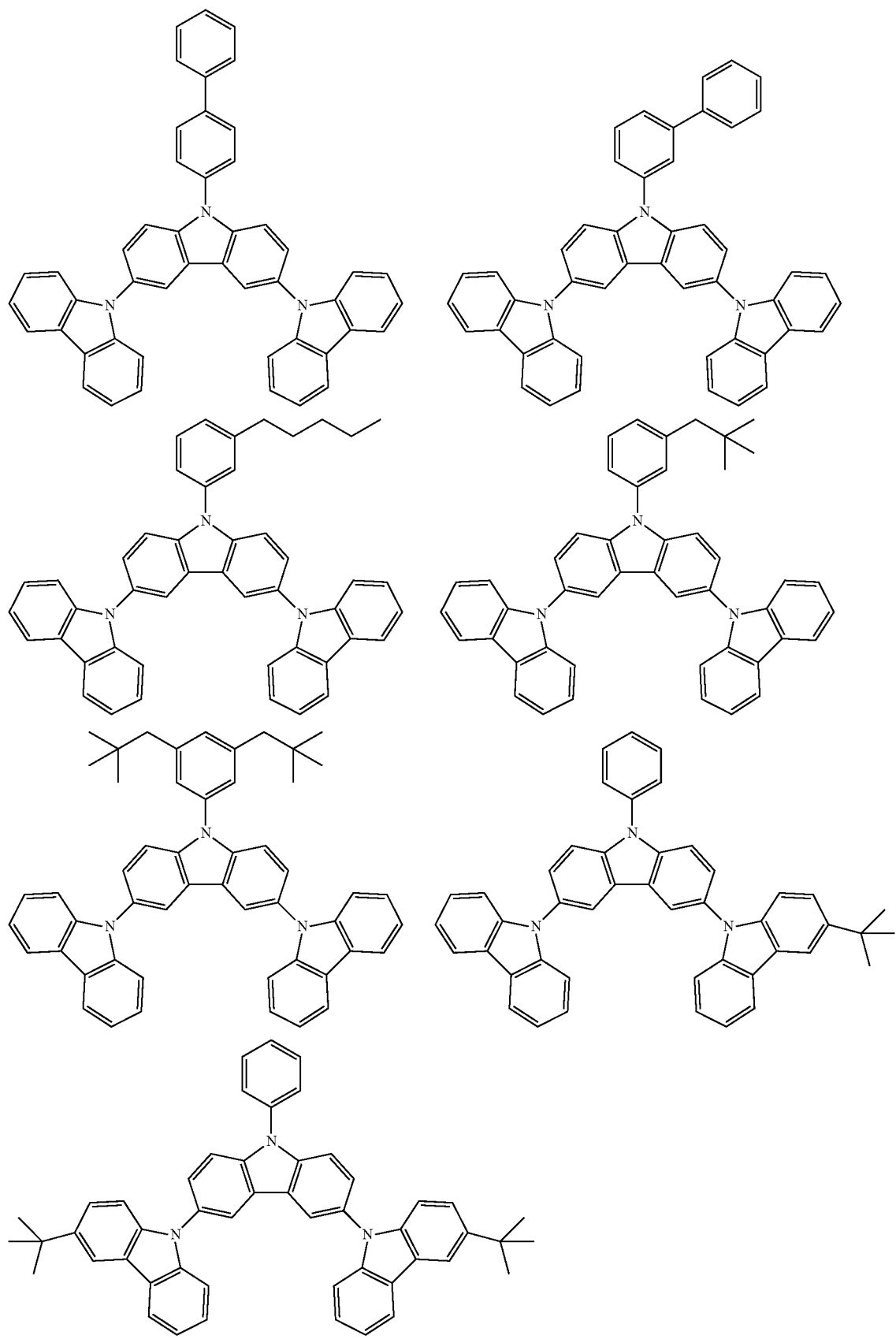

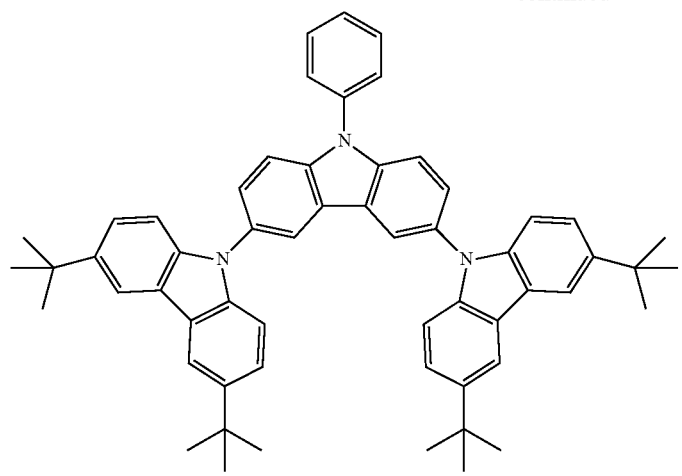
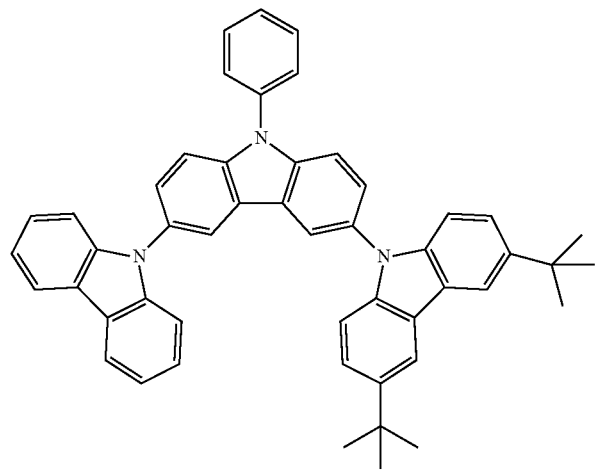
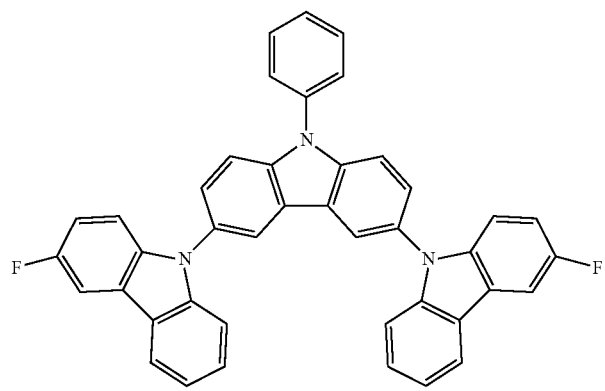
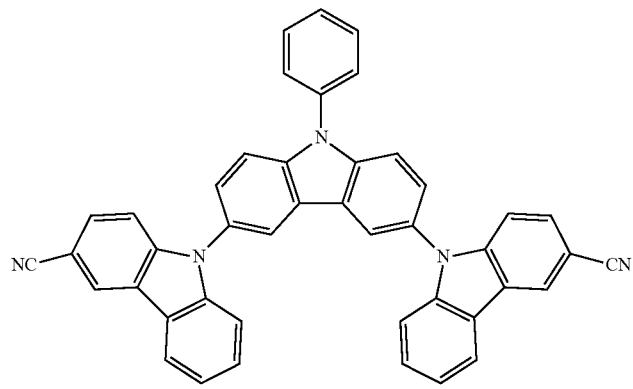

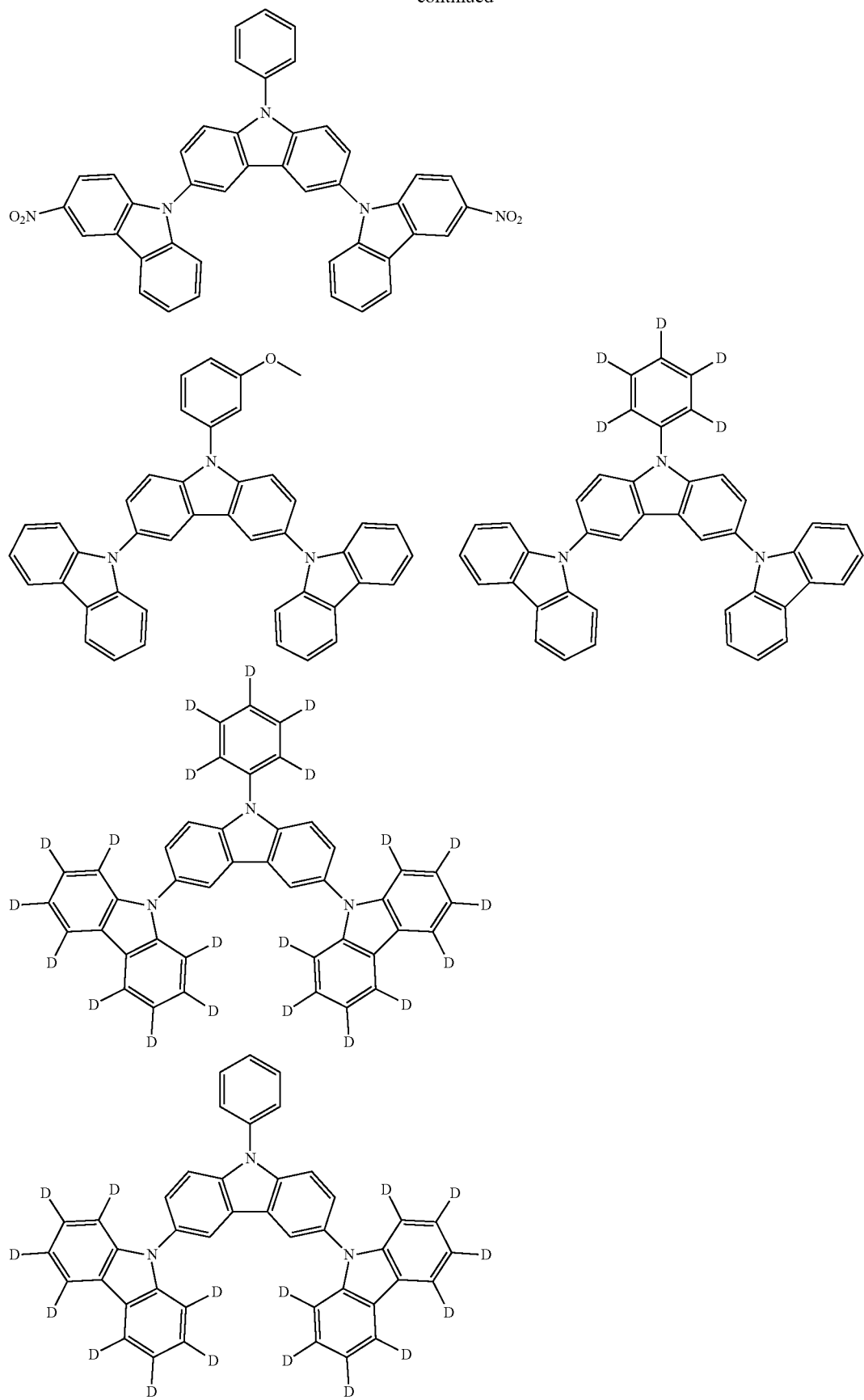

101
102
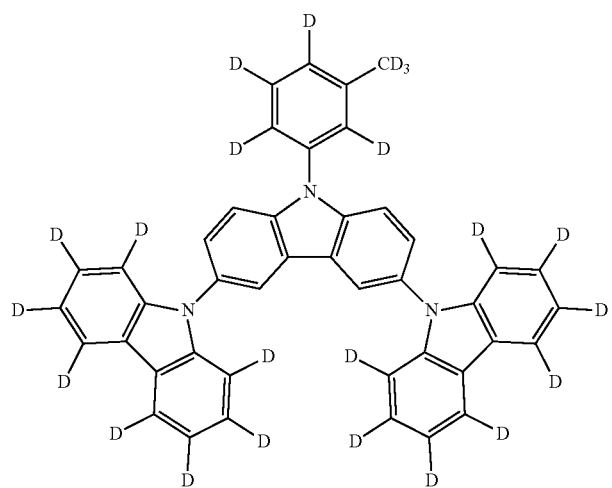
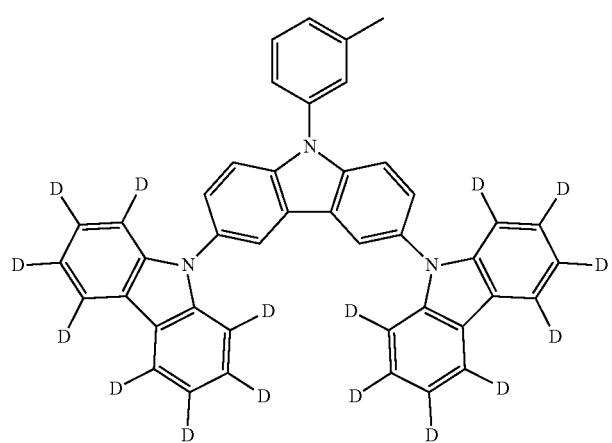
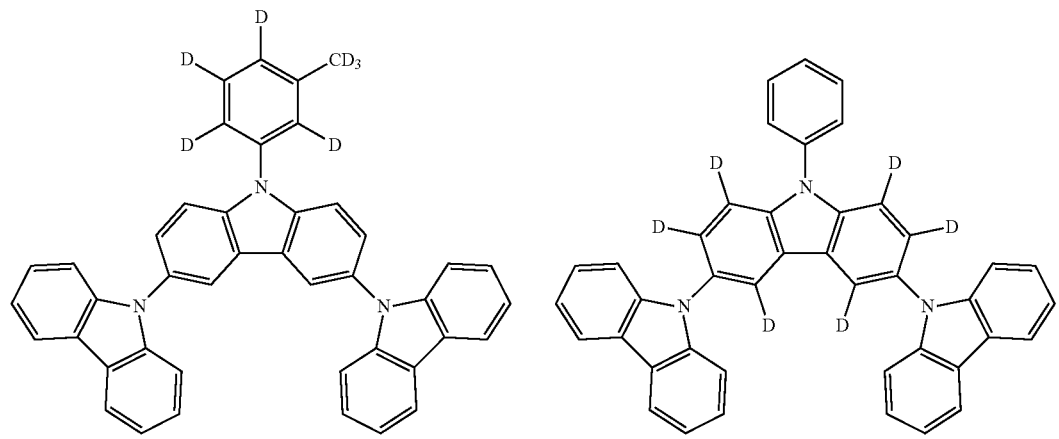

-continued
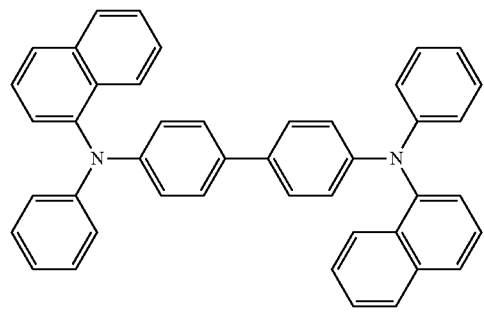
103
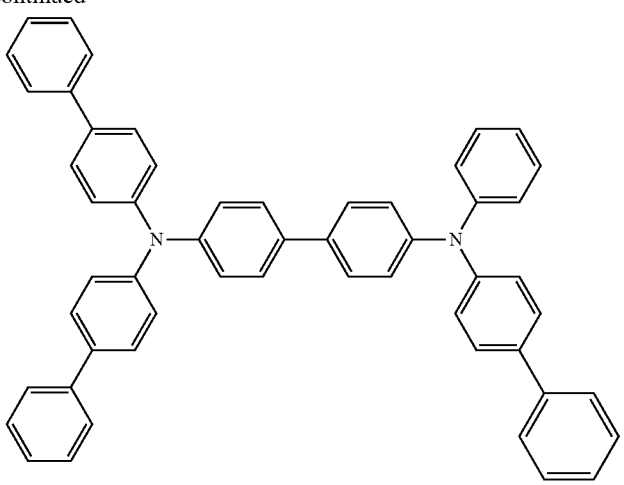
104
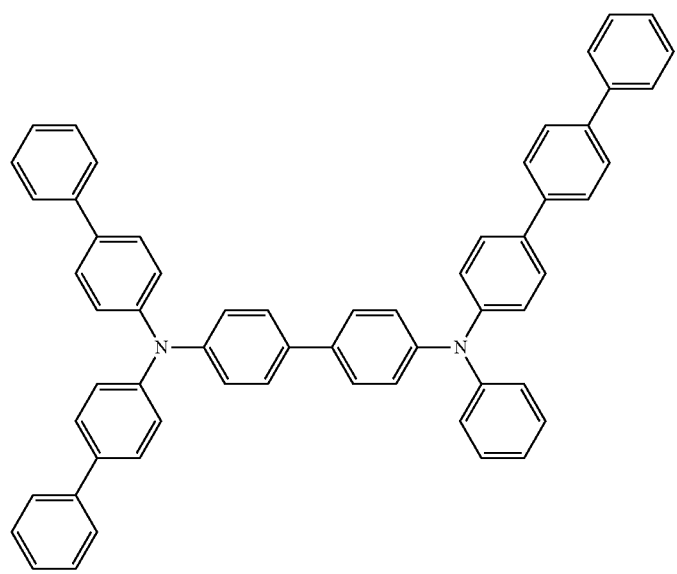
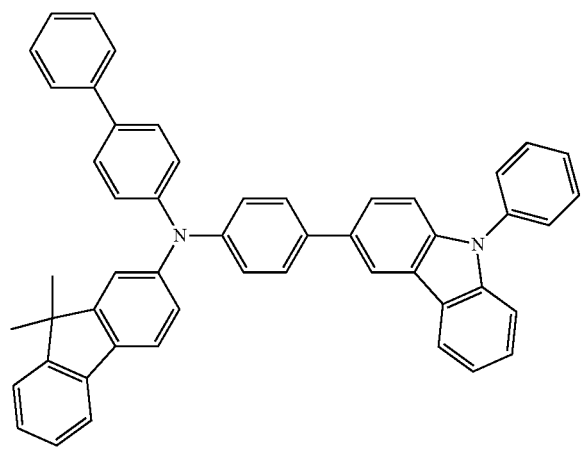

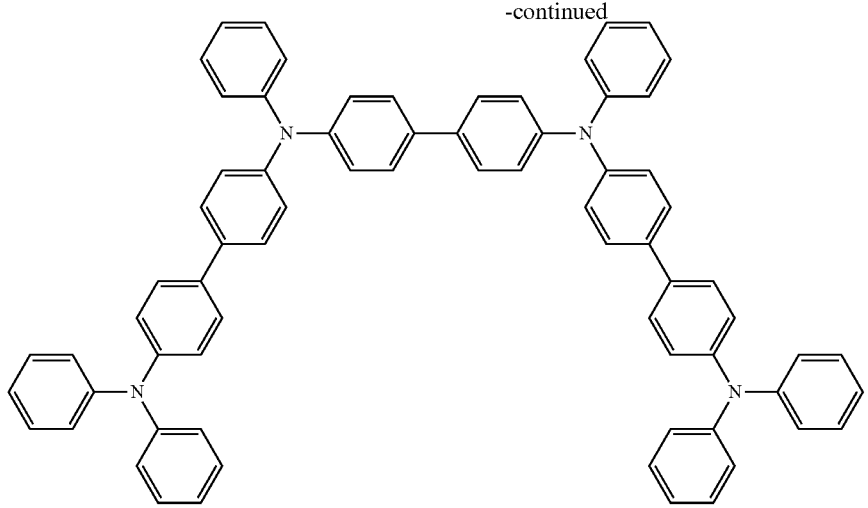

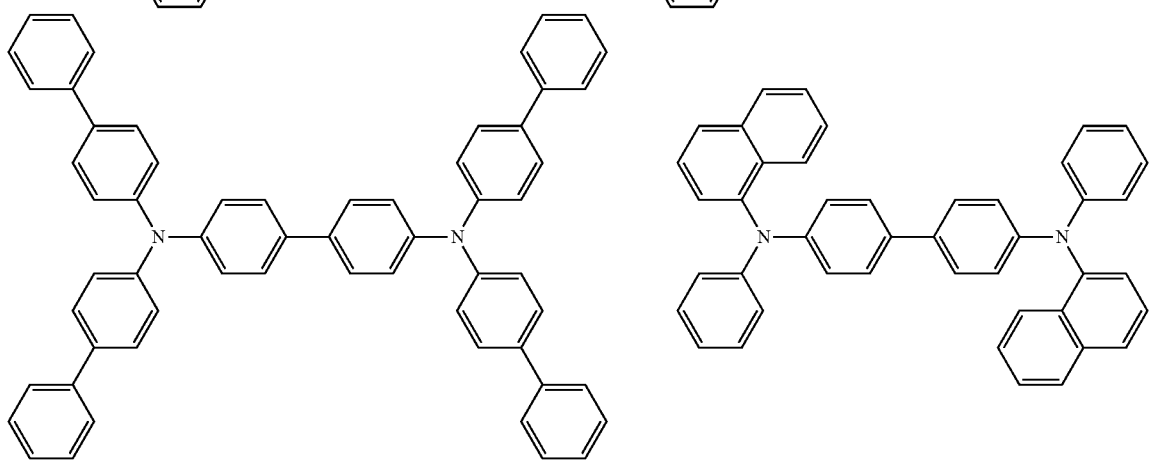

In addition to the above, the detailed description on the hole injecting layer and the hole transporting layer in paragraphs [0165] to [0167] of JP-A-2008-270736 can also be applied to the present invention. In addition, the detailed description in paragraphs [0250] to [0339] of JP-A-2011-71452 can also be applied to the hole injecting layer and the hole transporting layer according to the present invention.

The hole injecting layer preferably contains an electron receptive dopant. By incorporating the electron receptive dopant into the hole injecting layer, for example, there are brought such effects that the hole injecting properties are enhanced; that the driving voltage is lowered; and that the efficiency is enhanced. The electron receptive dopant may be any one of organic materials and inorganic materials as long as it is capable of withdrawing electrons from the material to be doped and generating radical cations. Examples thereof include TCNQ compounds such as tetracyanoquinodimethane (TCNQ) and tetrafluorotetracyanoquinodimethane ($F_4$-TCNQ), hexaazatriphenylene compounds such as hexacyanohexaazatriphenylene (HAT-CN), and molybdenum oxide.

The electron receptive dopant in the hole injecting layer is contained in the amount of preferably from 0.01 to 50% by mass, more preferably from 0.1 to 40% by mass, and still more preferably from 0.2 to 30% by mass relative to the total mass of the compounds forming the hole injecting layer.

(A-2) Electron Blocking Layer:

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be used.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one or two or more kinds of materials selected from the above-exemplified materials or a multilayer structure composed of a plurality of layers having the same composition or different compositions.

The material which is used in the electron blocking layer preferably has higher $S_1$ energy than that of the light emitting material in view of color purity, luminous efficiency, and driving durability. The $S_1$ in the film state of the material used in the electron blocking layer is preferably higher than the $S_1$ of the light emitting material by 0.1 eV or more, more preferably by 0.2 eV or more, and still more preferably by 0.3 eV or more.

(B) Organic Layer Preferably Disposed Between Cathode and Light Emitting Layer:

Next, the (B) organic layer preferably disposed between the cathode and the light emitting layer is described.

(B-1) Electron Injecting Layer and Electron Transporting Layer:

The electron injecting layer and the electron transporting layer are a layer having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (1) can be used. As other electron transporting materials, any one of compounds selected from aromatic ring tetracarboxylic acid anhydrides such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silole; hydrocarbon compounds with fused rings, such as naphthalene, anthracene, phenanthrene, triphenylene, and pyrene is preferable. Any one of compounds selected from pyridine derivatives, benzimidazole derivatives, imidazopyridine derivatives, metal complexes, and hydrocarbon compounds with fused rings are more preferable.

From the viewpoint that decreasing the driving voltage, the thickness of each of the electron injecting layer and the electron transporting layer is preferably not more than 500 nm.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or two or more kinds of materials selected from the above-exemplified materials or a multilayer structure composed of a plurality of layers having the same composition or different compositions.

The electron injecting layer preferably contains an electron donating dopant. By incorporating the electron donating dopant into the electron injecting layer, for example, there are brought such effects that the electron injecting properties are enhanced; that the driving voltage is lowered; and that the efficiency is enhanced. The electron donating dopant may be any one of organic materials and inorganic materials as long as it is capable of giving electrons to the material to be doped and generating radical anions. Examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01 to 50% by mass, more preferably from 0.1 to 40% by mass, and still more preferably 0.5 to 30% by mass relative to the total mass of the compounds forming the electron injecting layer.

(B-2) Hole Blocking Layer:

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

Since the $S_1$ energy of the organic compound in the film state constituting the hole blocking layer prevents the energy movement of excitons produced in the light emitting layer, and thus, does not lower the luminous efficiency, higher $S_1$ energy of the light emitting material is preferable.

As an example of the organic compound constituting the hole blocking layer, for example, the compound represented by the general formula (1) can be used.

Examples of the organic compounds constituting the hole blocking layer, other than the compound represented by the general formula (1), include aluminum complexes such as aluminum(III) bis(2-methyl-8-quinolinato) 4-phenylphenolate (abbreviated as "BAlq"), triazole derivatives, and phenanthroline derivatives such as 2,9-dimethyl-4,7-diphenyl-1,10-phenanthroline (abbreviated as "BCP").

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or more materials selected from the above-exemplified materials or a multilayer structure composed of a plurality of layers having the same composition or different compositions.

The material which is used in the hole blocking layer preferably has higher $S_1$ energy than that of the light emitting material in view of color purity, luminous efficiency, and driving durability. The $S_1$ in the film state of the material used in the hole blocking layer is preferably higher than the $S_1$ of the light emitting material by 0.1 eV or more, more preferably by 0.2 eV or more, and still more preferably by 0.3 eV or more.

(B-3) Material Especially Preferably Used in Organic Layer, which is Preferably Disposed Between Cathode and Light Emitting Layer:

For the organic electroluminescent element according to the present invention, examples of the material which is especially preferably used in the materials for an organic layer, preferably disposed between the (B) cathode and the light emitting layer include the compound represented by the general formula (1), a compound represented by the following general formula (P-1), and a compound represented by the following general formula (O-1).

A compound represented by the general formula (O-1) and a compound represented by the general formula (P-1) are hereunder described.

The organic electroluminescent element according to the present invention preferably includes at least one organic layer between the light emitting layer and the cathode, and the organic layer preferably contains at least one of compounds represented by the following general formula (O-1), from the viewpoint of efficiency or driving voltage of the element. The general formula (O-1) is hereunder described.

General Formula (O-1)

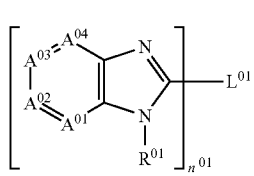

In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and plural $R^A$s may be the same as or different from each other. $L^{O1}$ represents any of divalent to hexavalent linking groups composed of an aryl ring or a heteroaryl ring. $n^{O1}$ represents an integer of 2 to 6.

$R^{O1}$ represents an alkyl group (preferably having from 1 to 8 carbon atoms), an aryl group (preferably having from 6 to 30 carbon atoms), or a heteroaryl group (preferably having from 4 to 12 carbon atoms), which may have a substituent selected from the above-described Substituent Group A. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group. Of these, an alkyl group and an aryl group are more preferable, with an aryl group being still more preferable. In the case where the aryl group of $R^{O1}$ has plural substituents, the plural substituents may be bonded to each other to form a 5- or 6-membered ring. The aryl group of $R^{O1}$ is preferably a phenyl group which may have a substituent selected from the Substituent Group A, more preferably a phenyl group which may be substituted with an alkyl group or an aryl group, and still more preferably an unsubstituted phenyl group or a 2-phenylphenyl group.

$A^{O1}$ to $A^{O4}$ each independently represent C—$R^A$ or a nitrogen atom. It is preferable that from 0 to 2 of $A^{O1}$ to $A^{O4}$ are a nitrogen atom; and it is more preferable that 0 or 1 of $A^{O1}$ to $A^{O4}$ is a nitrogen atom. It is preferable that all of $A^{O1}$ to $A^{O4}$ are C—$R^A$, or $A^{O1}$ is a nitrogen atom, and $A^{O2}$ to $A^{O4}$ are C—$R^A$; it is more preferable that $A^{O1}$ is a nitrogen atom, and $A^{O2}$ to $A^{O4}$ are C—$R^A$; and it is still more preferable that $A^{O1}$ is a nitrogen atom, $A^{O2}$ to $A^{O4}$ are C—$R^A$, and $R^A$s are all a hydrogen atom.

$R^A$ represents a hydrogen atom, an alkyl group (preferably having from 1 to 8 carbon atoms), an aryl group (preferably having from 6 to 30 carbon atoms), or a heteroaryl group (preferably having from 4 to 12 carbon atoms), and may have a substituent selected from the above-described Substituent Group A. In addition, plural $R^A$s may be the same as or different from each other. $R^A$ is preferably a hydrogen atom or an alkyl group, and more preferably a hydrogen atom.

$L^{O1}$ represents a divalent to hexavalent linking group composed of an aryl ring (preferably having from 6 to 30 carbon atoms) or a heteroaryl ring (preferably having from 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L_{O1}$ may have a substituent selected from the above-described Substituent Group A, and in the case where $L^{O1}$ has a substituent, the substituent is preferably an alkyl group, an aryl group, or a cyano group. Specific examples of $L^{O1}$ include the following.

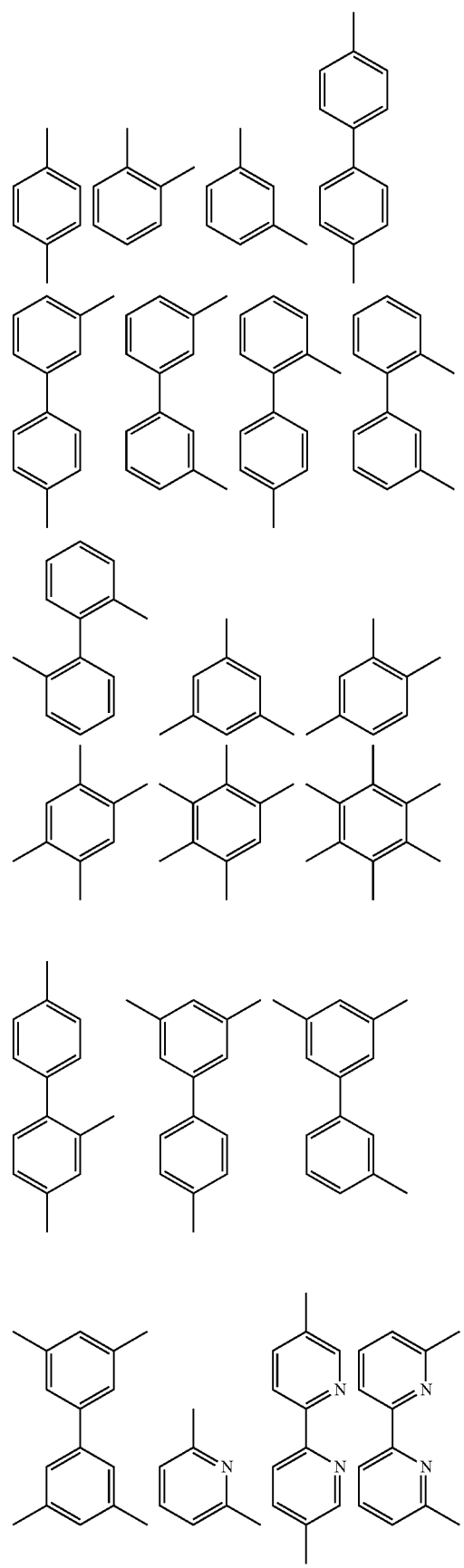

-continued

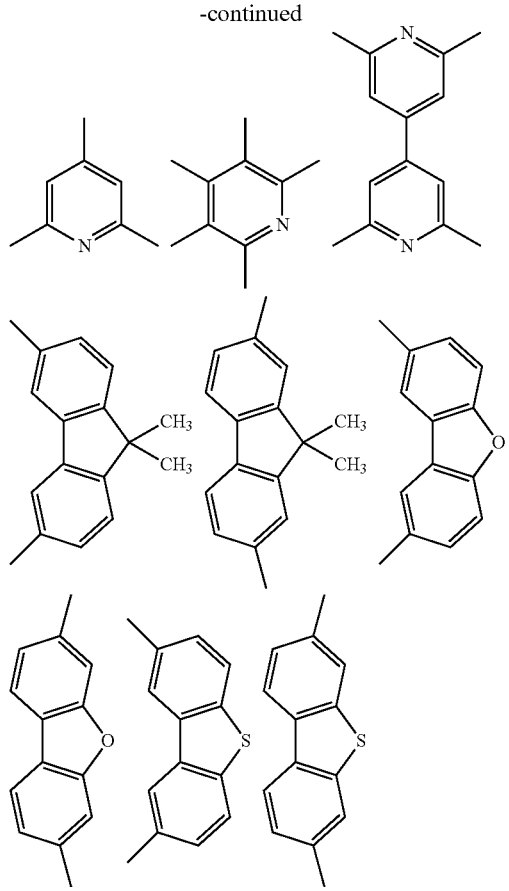

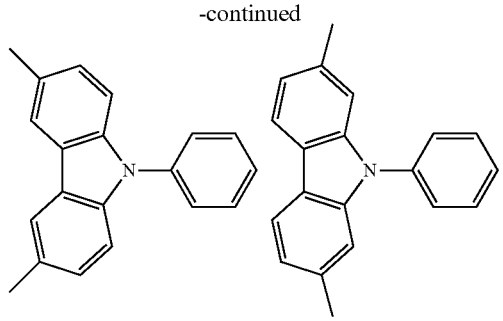

-continued $n^{O1}$ represents an integer of from 2 to 6, preferably an integer of from 2 to 4, and more preferably 2 or 3. $n^{O1}$ is most preferably 3 from the viewpoint of the efficiency of the element, or $n^{O1}$ is most preferably 2 from the viewpoint of the durability of the element.

The glass transition temperature (Tg) of the compound represented by the general formula (O-1) is preferably from 100° C. to 300° C., more preferably from 120° C. to 300° C., still more preferably from 130° C. to 300° C., and even still more preferably from 140° C. to 300° C. from the viewpoint of stability at the time of storage at a high temperature, or stable operation during driving at a high temperature or against heat generation during driving.

Specific examples of the compound represented by the general formula (O-1) are shown below, but it should not be construed that the compound represented by the general formula (O-1) which can be used in the present invention is limited to these specific examples.

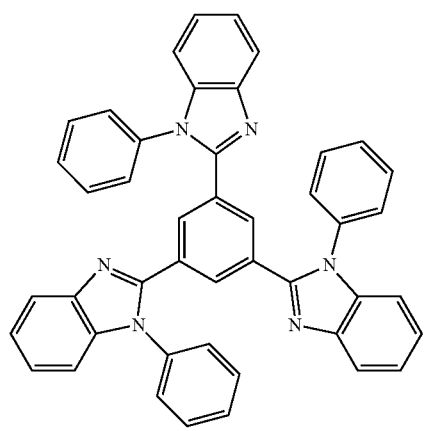

OM-1

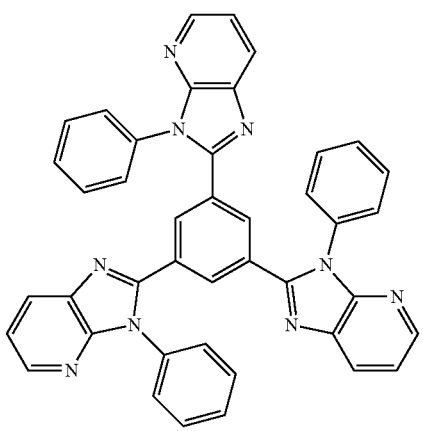

OM-2

-continued
OM-3
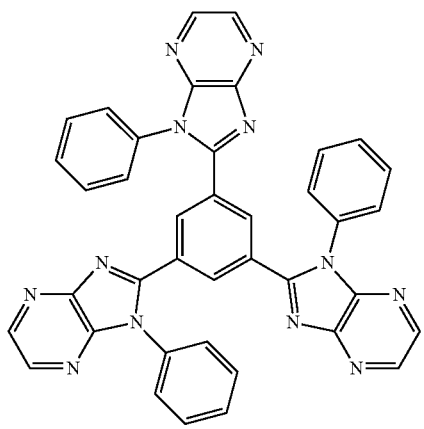
OM-4
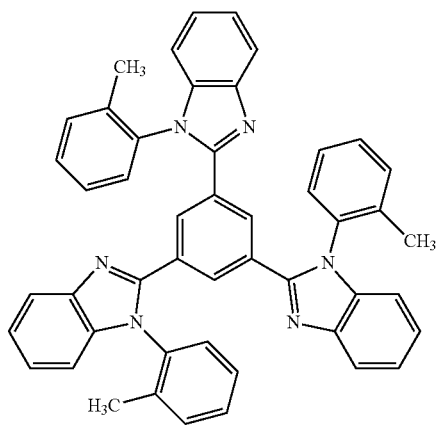
OM-5
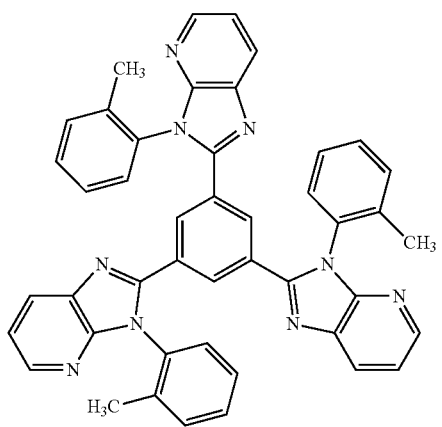
OM-6
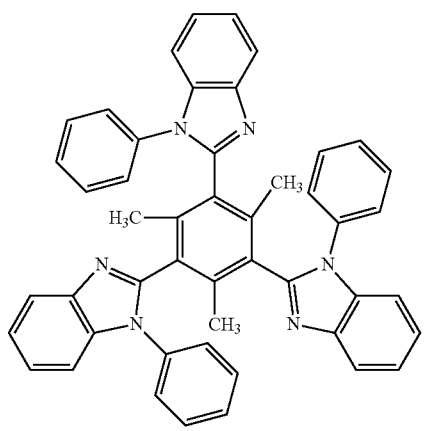
OM-7
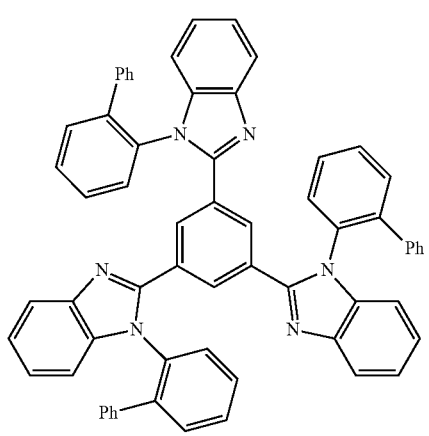
OM-8
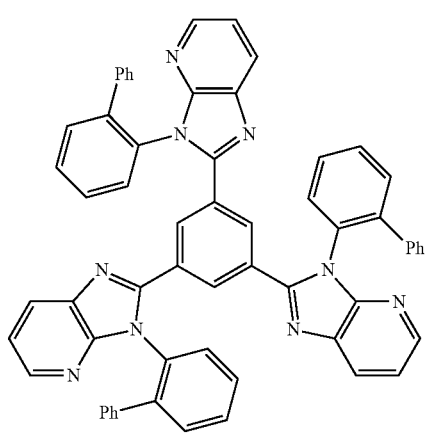

-continued
OM-9
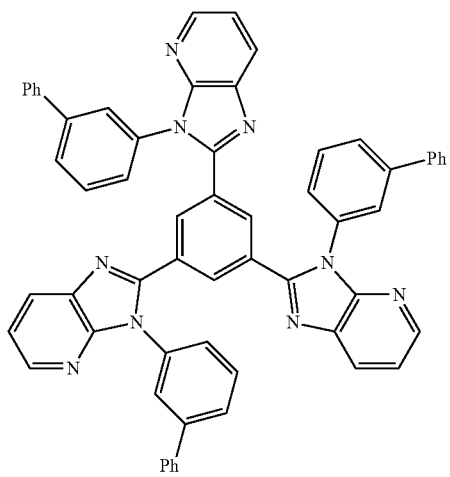
OM-10
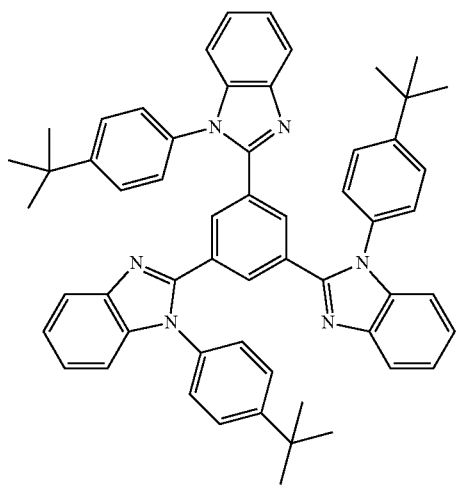
OM-11
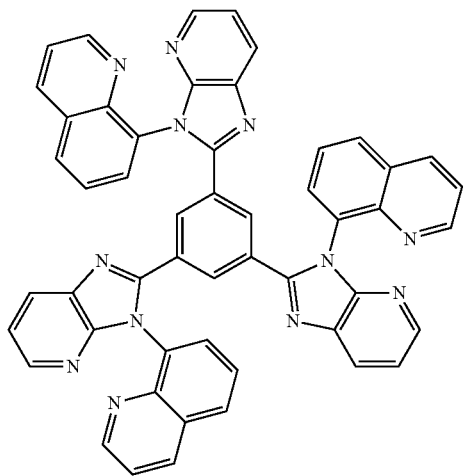
OM-12
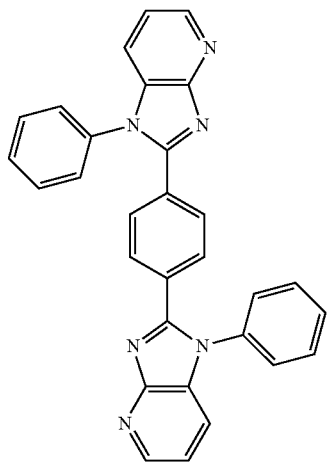
OM-13
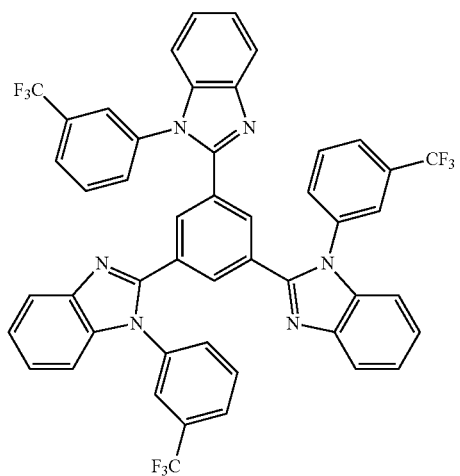
OM-14
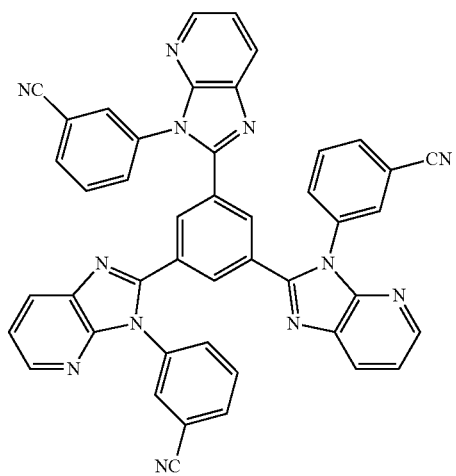

-continued
OM-15
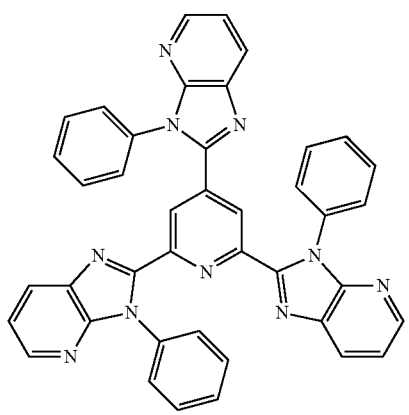
OM-16
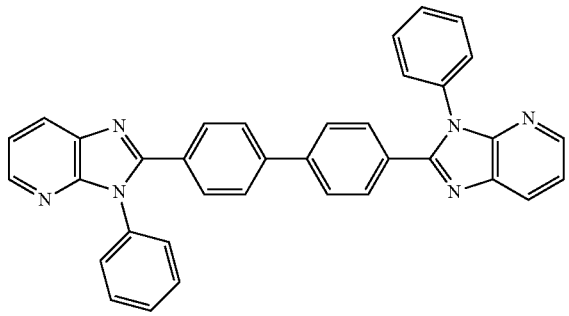
OM-17
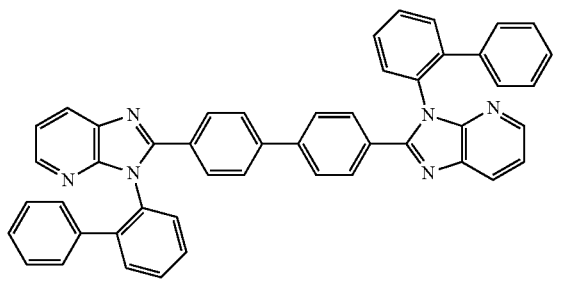
OM-18
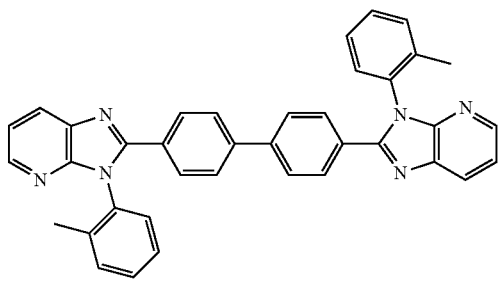
OM-19
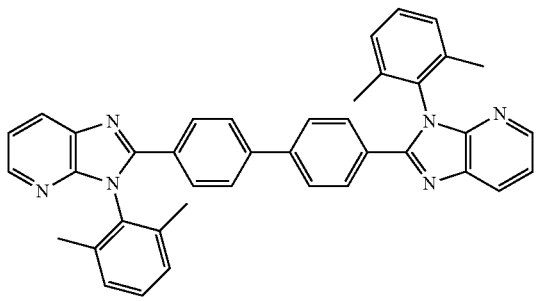
OM-20
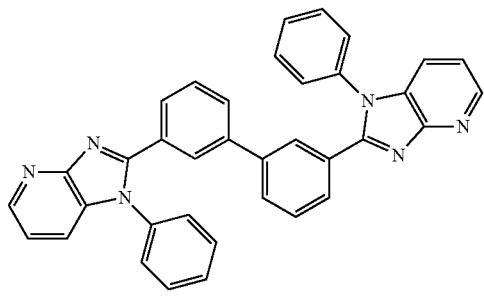
OM-21
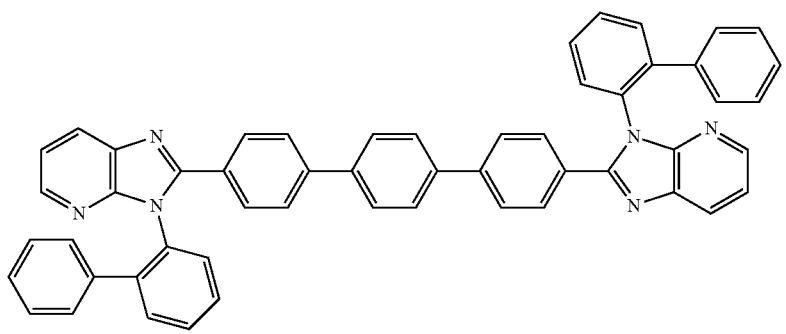

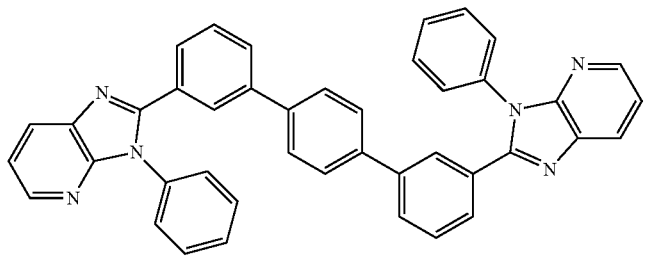

OM-22

The compound represented by the general formula (O-1) can be synthesized by the method described in JP-A-2001-335776. After the synthesis, it is preferable that after performing purification by means of column chromatography, recrystallization, reprecipitation, or the like, purification is performed by means of sublimation purification. According to the sublimation purification, not only organic impurities can be separated, but inorganic salts, residual solvent, moisture, and the like can be effectively removed.

In the organic electroluminescent element according to the present invention, though the compound represented by the general formula (O-1) is preferably contained in the organic layer between the light emitting layer and the cathode, it is more preferably contained in the layer on the cathode side adjacent to the light emitting layer.

The compound represented by the general formula (O-1) is preferably included in the amount of from 70 to 100% by mass, and more preferably from 85 to 100% by mass relative to the total mass of the organic layer to be added.

The organic electroluminescent element according to the present invention preferably includes at least one organic layer between the light emitting layer and the cathode, and from the viewpoint of the efficiency of the element or the driving voltage, it is preferable that the organic layer contains at least one compound represented by the following general formula (P). The general formula (P) is hereunder described.

General Formula (P)

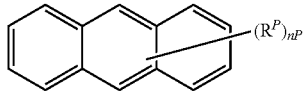

In the general formula (P), $R^P$ represents an alkyl group (preferably having from 1 to 8 carbon atoms), an aryl group (preferably having from 6 to 30 carbon atoms), or a heteroaryl group (preferably having from 4 to 12 carbon atoms), each of which may have a substituent selected from the above-described Substituent Group A. nP represents an integer of from 1 to 10, and in the case where plural $R^P$s are present, they may be the same as or different from each other. At least one of $R^P$s is a substituent represented by the following general formulae (P-1) to (P-3).

General Formula (P-1)

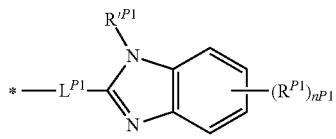

General Formula (P-2)

General Formula (P-3)

In the general formulae (P-1) to (P-3), $R^{P1}$ to $R^{P3}$, and $R^{\prime P1}$ to $R^{\prime P3}$, each represent an alkyl group (preferably having from 1 to 8 carbon atoms), an aryl group (preferably having from 6 to 30 carbon atoms), or a heteroaryl group (preferably having from 4 to 12 carbon atoms), each of which may have a substituent selected from the above-described Substituent Group A. $n^{P1}$ and $n^{P2}$ represent an integer of from 0 to 4, and in the case where plural $R^{P1}$ to $R^{P3}$, and $R^{\prime P1}$ to $R^{\prime P3}$, are present, they may be the same as or different from each other. $L^{P1}$ to $L^{P3}$ represent any one of divalent linking groups composed of a single bond, an aryl ring, or a heteroaryl ring. * represents a position bonding to the anthracene ring of the general formula (P).

A preferred substituent other than the substituents represented by (P-1) to (P-3) as $R^P$ is an aryl group, more preferably any one of a phenyl group, a biphenyl group, a terphenyl group, and a naphthyl group, and still more preferably a naphthyl group.

$R^{P1}$ to $R^{P3}$, $R^{\prime P1}$ to $R^{\prime P3}$, are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P3}$ are preferably any one of divalent linking groups composed of a single bond and an aryl ring, more preferably any one of a single bond, phenylene, biphenylene, terphenylene, and naphthylene, still more preferably any one of a single bond, phenylene, and naphthylene.

Specific examples of the compound represented by the general formula (P) are shown below, but it should not be construed that the compound represented by the general formula (P) which can be used in the present invention is limited to these specific examples.

121 122
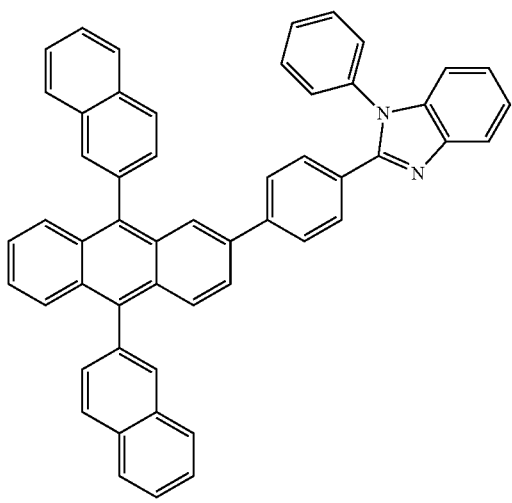
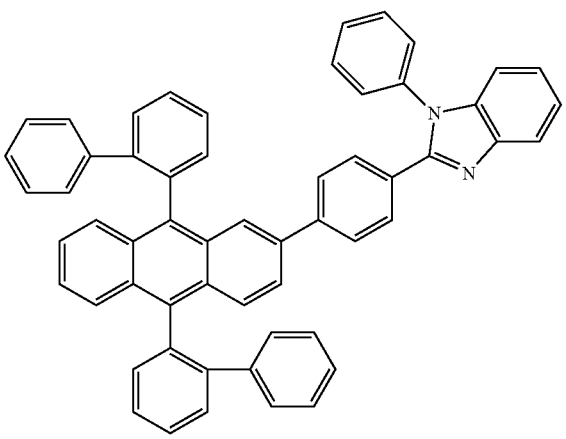
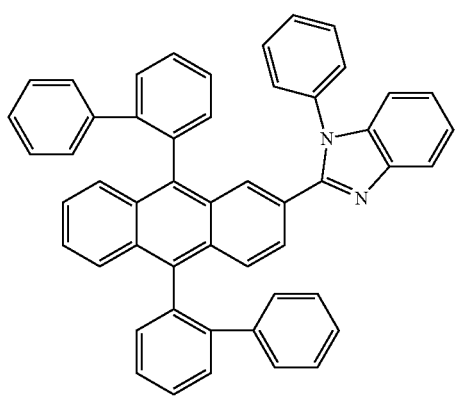
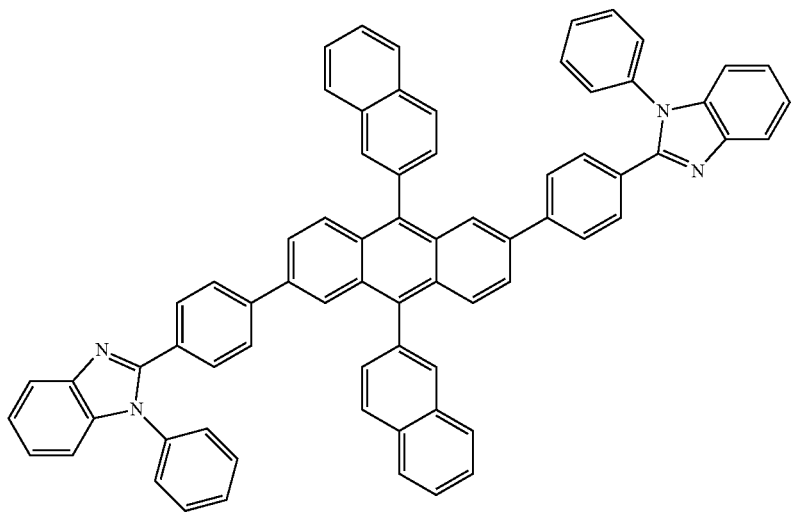

-continued
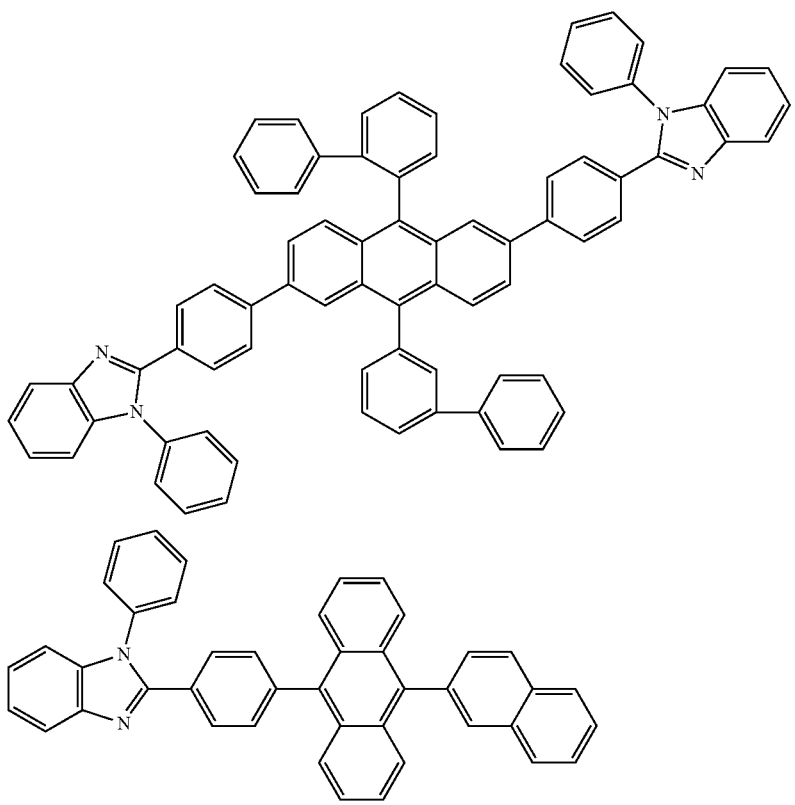
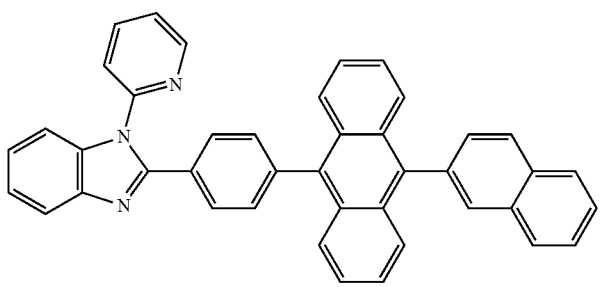
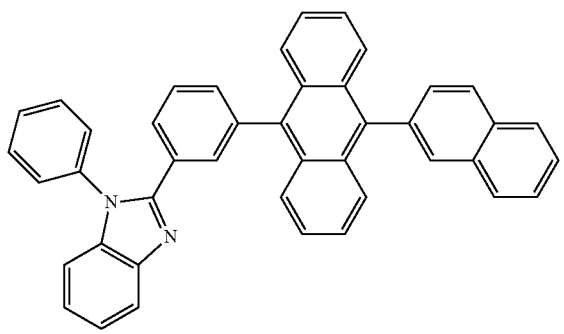
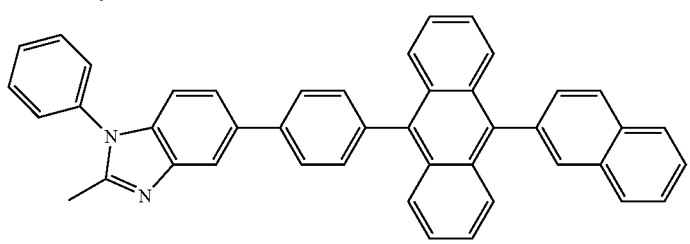

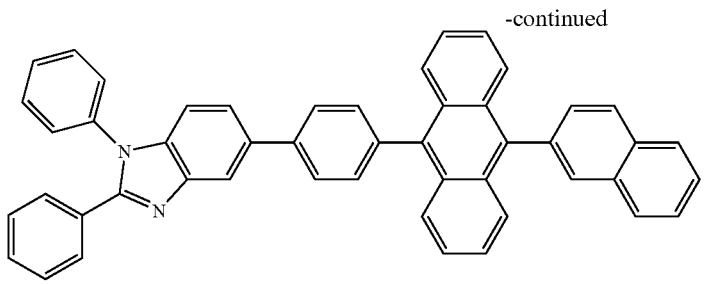

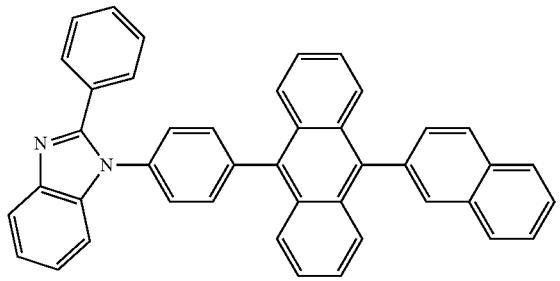 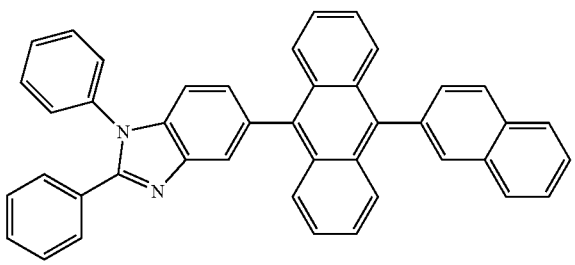

The compound represented by the general formula (P) can be synthesized by the method described in WO 2003/060956 and WO 2004/080975. After the synthesis, it is preferable that after performing purification by means of column chromatography, recrystallization, reprecipitation, or the like, purification is performed by means of sublimation purification. According to the sublimation purification, not only organic impurities can be separated, but inorganic salts, residual solvent, moisture, and the like can be effectively removed.

In the organic electroluminescent element according to the present invention, though the compound represented by the general formula (P) is preferably contained in the organic layer between the light emitting layer and the cathode, it is more preferably contained in the layer adjacent to the cathode.

The compound represented by the general formula (P) is preferably included in the amount of from 70 to 100% by mass, and more preferably from 85 to 100% by mass relative to the total mass of the organic layer to be added.

Preferred examples of the material other than the material, which is used in the electron injecting layer or the electron transporting layer in the organic electroluminescent element according to the present invention, include silole compounds described in JP-A-09-194487 or the like, phosphine oxide compounds described in JP-A-2006-73581 or the like, nitrogen-containing aromatic 6-membered heterocyclic compounds described in JP-A-2005-276801, JP-A-2006-225320, WO 2005/085387, or the like, compounds having a nitrogen-containing aromatic 6-membered heterocyclic structure and a carbazole structure described in WO 2003/080760, WO 2005/085387, or the like, and aromatic hydrocarbon compounds described in US-A-2009/0009065, WO 2010/134350, JP-T-2010-535806, or the like (e.g., naphthalene compounds, anthracene compounds, triphenylene compounds, phenanthrene compounds, pyrene compounds, fluoranthene compounds, and the like).

<Protective Layer>

In the present invention, the entirety of the organic electroluminescent element may be protected by a protective layer.

For the protective layer, the detailed description in paragraphs [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph [0171] of JP-A-2008-270736 can be applied to the present invention.

<Driving Method>

The organic electroluminescent element according to the present invention can emit light by applying a direct current (it may include an alternate current component, if desired) voltage (usually from 2 volts to 15 volts) or a direct current between the anode and the cathode.

As a driving method of the organic electroluminescent element according to the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element according to the present invention is preferably 5% or more, more preferably 6% or more, and still more preferably 7% or more. As for the numerical value of the external quantum efficiency, a maximum value of the external quantum efficiency obtained when the organic electroluminescent element is driven at 20° C., or a value of the external quantum efficiency in the vicinity of from 300 to 400 cd/m$^2$ obtained when the element is driven at 20° C. can be employed.

The internal quantum efficiency of the organic electroluminescent element according to the present invention is preferably 30% or more, more preferably 50% or more, and still more preferably 70% or more. The internal quantum efficiency of the element is calculated by dividing the external quantum efficiency by the light extraction efficiency. Though the light extraction efficiency in usual organic EL elements is about 20%, by taking into consideration the shape of a substrate, the shape of an electrode, the film thickness of an organic layer, the film thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element according to the present invention, its light emitting wavelength is the same as the maximum light emitting wavelength of the material for the organic electroluminescent element according to the present invention, and the element is used for blue light emission among the three primary colors of light. In the organic electroluminescent element according to the present invention, the compound represented by the general formula (1) is subjected to blue light emission as the light emitting material.

<Use of Organic Electroluminescent Element According to the Present Invention>

The organic electroluminescent element according to the present invention can be suitably used for display elements, displays, backlights, electrophotography, illumination light sources, recording light sources, exposure light sources, readout light sources, signs, billboards, interior decorations, optical communications, and the like. In particular, it is preferably used for devices to be driven in a region of high-intensity luminescence, such as a light emitting device, an illumination device, and a display device.

[Light Emitting Device]

The light emitting device according to the present invention comprises the organic electroluminescent element according to the present invention.

Next, the light emitting device according to the present invention is described with reference to FIG. 2.

The light emitting device according to the present invention is formed by using the organic electroluminescent element.

Figure 2:
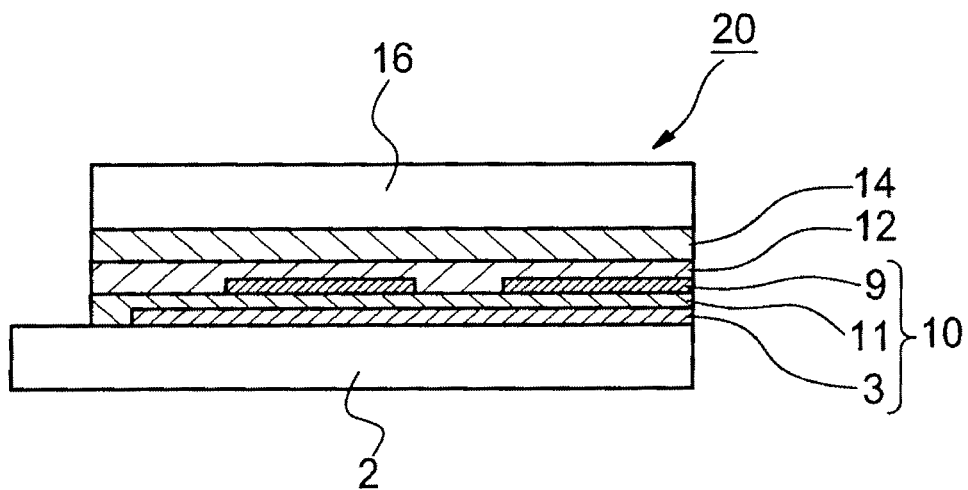
FIG. 2 is a schematic view showing one example of the light emitting device according to the present invention.

FIG. 2 is a cross-sectional view schematically showing one example of the light emitting device according to the present invention. A light emitting device 20 in FIG. 2 is constituted of a transparent substrate 2 (supporting substrate), an organic electroluminescent element 10, a sealing enclosure 16, and the like.

The organic electroluminescent element 10 is constituted by laminating an anode 3 (first electrode), an organic layer 11, and a cathode 9 (second electrode) in this order on the substrate 2. In addition, a protective layer 12 is laminated on the cathode 9, and a sealing enclosure 16 is further provided on the protective layer 12 via an adhesive layer 14. Incidentally, a part of each of the electrodes 3 and 9, a diaphragm, an insulating layer, and the like are omitted in FIG. 2.

Here, a photocurable adhesive such as an epoxy resin, or a thermosetting adhesive can be used for the adhesive layer 14, and for example, a thermosetting adhesive sheet can also be used as the adhesive layer 14.

The light emitting device according to the present invention is not particularly limited in its use, and it can be used as not only an illumination device but a display device of a television set, a personal computer, a mobile phone, electronic paper, or the like.

[Illumination Device]

The illumination device according to the present invention comprises the organic electroluminescent element according to the present invention.

Next, the illumination device according to the present invention is described with reference to FIG. 3.

Figure 3:
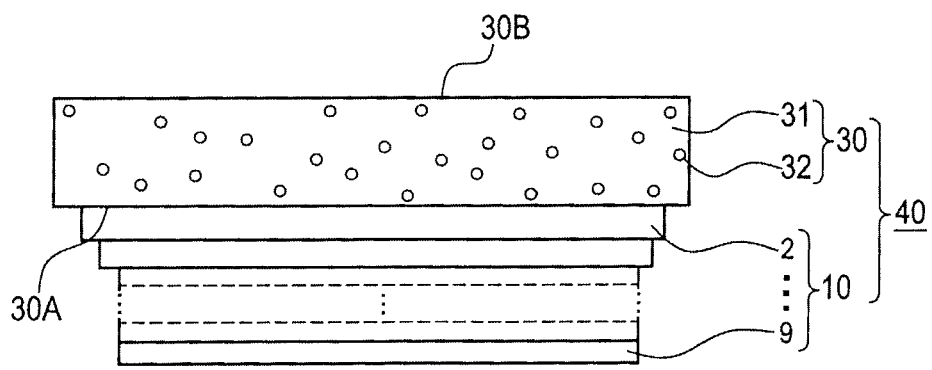
FIG. 3 is a schematic view showing one example of the illumination device according to the present invention.

FIG. 3 is a cross-sectional view schematically showing one example of the illumination device according to the present invention. As shown in FIG. 3, an illumination device 40 according to the present invention is provided with the above-described organic EL element 10 and a light scattering member 30. More specifically, the illumination device 40 is configured in such a manner that the substrate 2 of the organic EL element 10 and the light scattering member 30 are brought in contact with each other.

Though the light scattering member 30 is not particularly limited so far as it is able to scatter light, a member obtained by dispersing fine particles 32 in a transparent substrate 31 is used in FIG. 3. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is made incident onto a light incident surface 30A of the scattering member 30, the incident light is scattered by the light scattering member 30, and the scattered light is outputted as illuminating light from a light outputting surface 30B.

[Display Device]

The display device according to the present invention comprises the organic electroluminescent element according to the present invention.

The display device according to the present invention can be used for, for example, a display device of a television set, a personal computer, a mobile phone, electronic paper, or the like.

EXAMPLES

The characteristic features of the present invention are hereunder described in more detail with reference to the following Examples and Comparative Examples. The materials, use amounts, ratios, treatment details, treatment procedures, and the like shown in the following Examples and Comparative Examples can be appropriately modified so far as the gist of the present invention is not deviated. Accordingly, it should not be construed that the scope of the present invention is limited to the specific examples shown below.

1. Synthesis Example 1

Synthesis of Compound 1

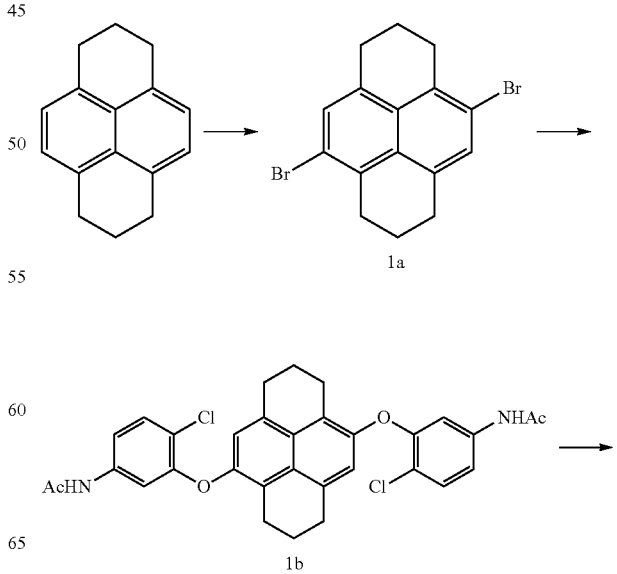

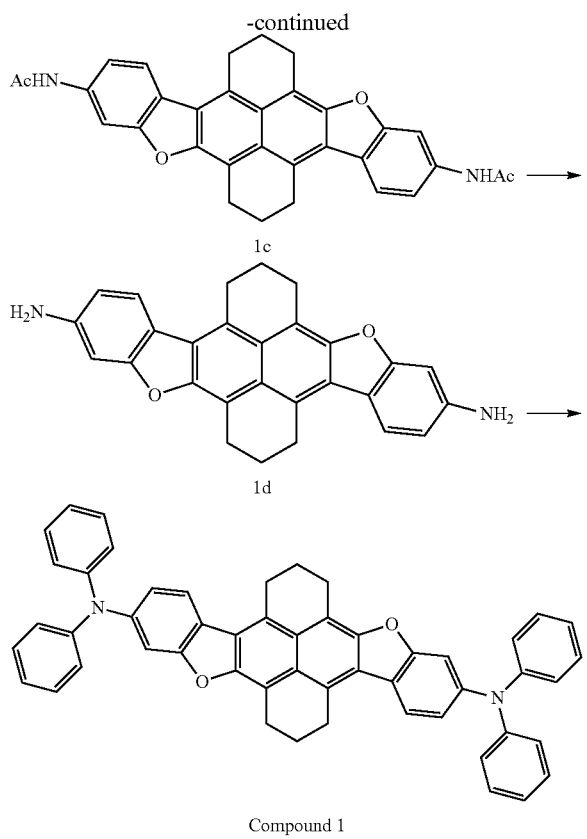

Compound 1

(Synthesis of Compound 1a)

To a dichloromethane solution (500 mL) of 50 g of 1,2,3,6,7,8-hexahydropyrene (manufactured by ALDRICH), bromine (26 mL) was added dropwise at room temperature and stirred for 4 hours. A deposited crystal was filtered and washed with ethanol and hexane, thereby obtaining Compound 1a (39 g).

(Synthesis of Compound 1b)

An NMP solution (850 mL) of Compound 1a (29 g), N-(4-chloro-3-hydroxyphenyl)acetamide (38 g), dipivaloylmethane (manufactured by Tokyo Chemical Industry Co., Ltd.) (2.9 g), copper(I) chloride (16 g), and cesium carbonate (128 g) was stirred in a nitrogen atmosphere at 150° C. for 12 hours. The reaction solution was filtered with Celite, toluene/water was added to the filtrate, and the mixture was subjected to a liquid separation operation. The organic layer was washed with saturated salt water, dried over magnesium sulfate, and then concentrated under reduced pressure. The concentration residue was purified by means of silica gel chromatography, thereby obtaining Compound 1b (18.7 g).

(Synthesis of Compound 1c)

To a DMAc solution (300 mL) of Compound 1b (15 g), tricyclohexyl phosphine.HBF$_4$ (3.9 g), and potassium carbonate (14.4 g), palladium acetate (1.2 g) was added in a nitrogen atmosphere at 150° C. and stirred for 12 hours. The obtained crude crystal was subjected to purification by means of silica gel column chromatography and washed with methanol, thereby obtaining Compound 1c (7.9 g).

(Synthesis of Compound 1d)

300 mL of an ethylene glycol/triglyme (1/1) solution of Compound 1c (6 g) and a saturated potassium hydroxide aqueous solution (8 mL) was stirred at 120° C. for 5 hours. The reaction solution was cooled, and a deposited crude crystal was collected by filtration. The obtained crude crystal was recrystallized from toluene/methanol, thereby obtaining Compound 1d (4.5 g).

(Synthesis of Compound 1)

To a xylene solution (50 mL) of Compound 1d (3.9 g), tBuONa (1.8 g), and iodobenzene (manufactured by Wako Chemical Industries, Ltd.) (5.8 g), Pd$_2$(dba)$_3$ (0.86 g) and a 10% by mass tri-tertiary-butyl phosphine/hexane solution (3.8 mL) were added in a nitrogen atmosphere, and the contents were stirred at 100° C. for 9 hours. Th reaction solution was poured into ethyl acetate/salt water, and the organic layer was washed with salt water and dried over magnesium sulfate, followed by concentration under reduced pressure. The concentration residue was subjected to purification by means of silica gel column chromatography, thereby obtaining Compound 1 (5.1 g). Incidentally, the identification of the obtained compound was carried out by means of elemental analysis and NMR and MASS spectra.

2. Evaluation of Physical Properties of Light Emitting Materials:

(a) Evaluation of Chromaticity:

The following Host Compound H-5 and each of light emitting materials shown in Table 1 were deposited on a quartz glass substrate at 25 mm×25 mm×0.7 mm by a vacuum deposition method in a mass ratio (93/7), thereby forming a thin film having a film thickness of 50 nm. The obtained thin film was irradiated with UV rays of 350 nm to emit light. The luminous spectrum at that time was measured using a fluorescent spectrophotometer (FP-6300, manufactured by JASCO Corporation), thereby determining the chromaticity (x, y). On the basis of the y value at that time, the chromaticity was evaluated according to the following 3 grades.

○: $0.04 \leq y \leq 0.12$
Δ: $0.03 \leq y < 0.04$, $0.09 < y \leq 0.12$
x: $y < 0.03$, $0.12 < y$ (Host Compound H-5)

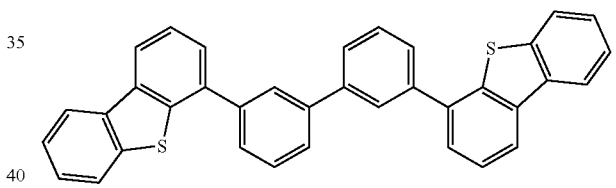

TABLE 1

| Light emitting material | Chromaticity | Note |
|---|---|---|
| Compound 1 | ○ | The present invention |
| Compound 2 | ○ | The present invention |
| Compound 3 | ○ | The present invention |
| Compound 6 | ○ | The present invention |
| Compound 7 | ○ | The present invention |
| Compound 8 | Δ | The present invention |
| Compound 10 | ○ | The present invention |
| Compound 11 | Δ | The present invention |
| Compound 12 | Δ | The present invention |
| Compound 16 | Δ | The present invention |
| Compound 18 | ○ | The present invention |
| Compound 20 | Δ | The present invention |
| Compound 28 | Δ | The present invention |
| Compound 29 | ○ | The present invention |
| Compound 31 | ○ | The present invention |
| Comparative Material 1 | X | Comparative Example |
| Comparative Material 2 | X | Comparative Example |
| Comparative Material 3 | X | Comparative Example |

Comparative Materials 1 to 3 used as the comparative light emitting material shown in Table 1 have the following structures. Incidentally, Comparative Material 1 is Compound 2-60 described in JP-T-2009-514812, Comparative Material 2 is Compound 2-61 described in JP-T-2009-514812, and Comparative Material 3 is Compound 6 described in JP-A-2005-19219.

Comparative Material 1
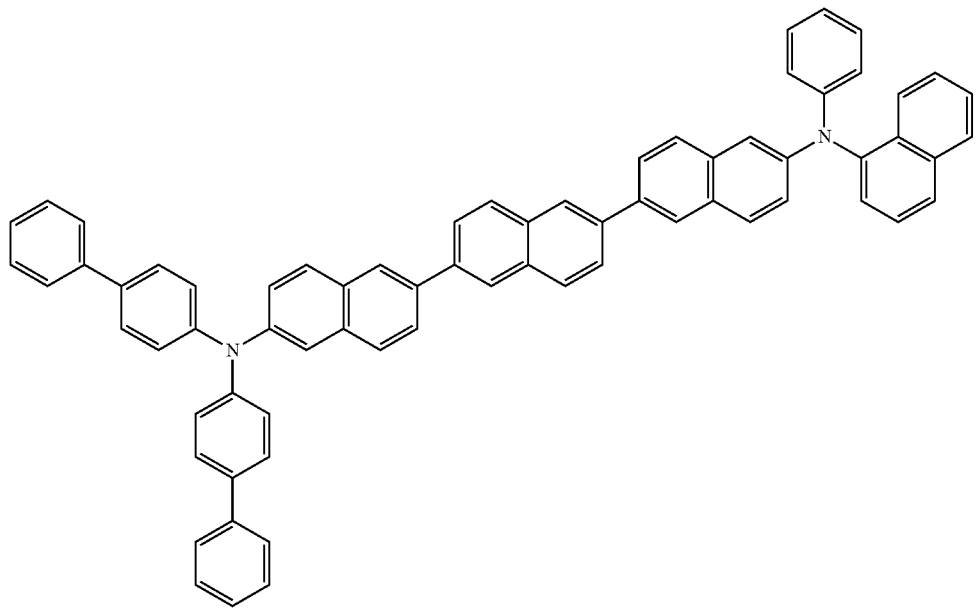
Comparative Material 2
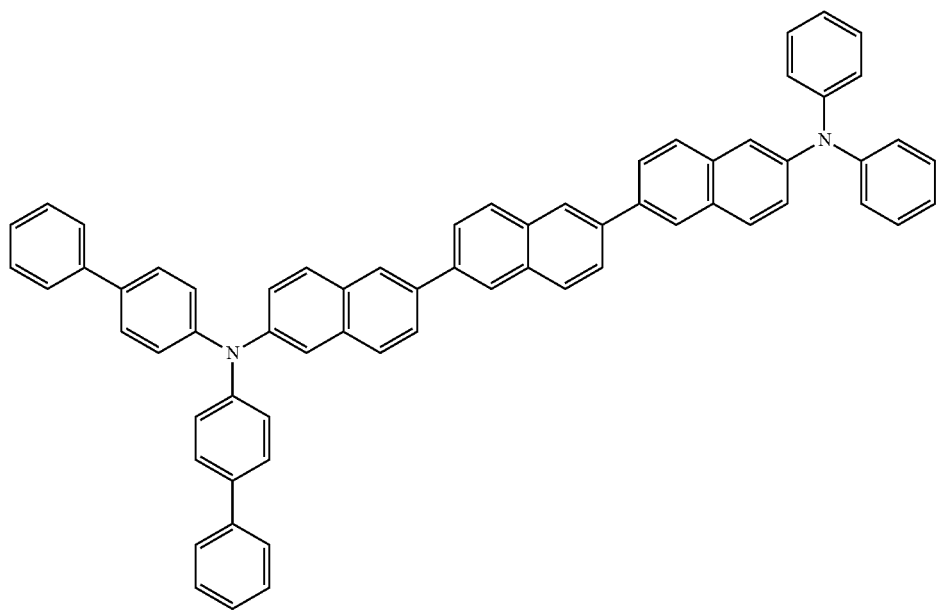

-continued

Comparative Material 3

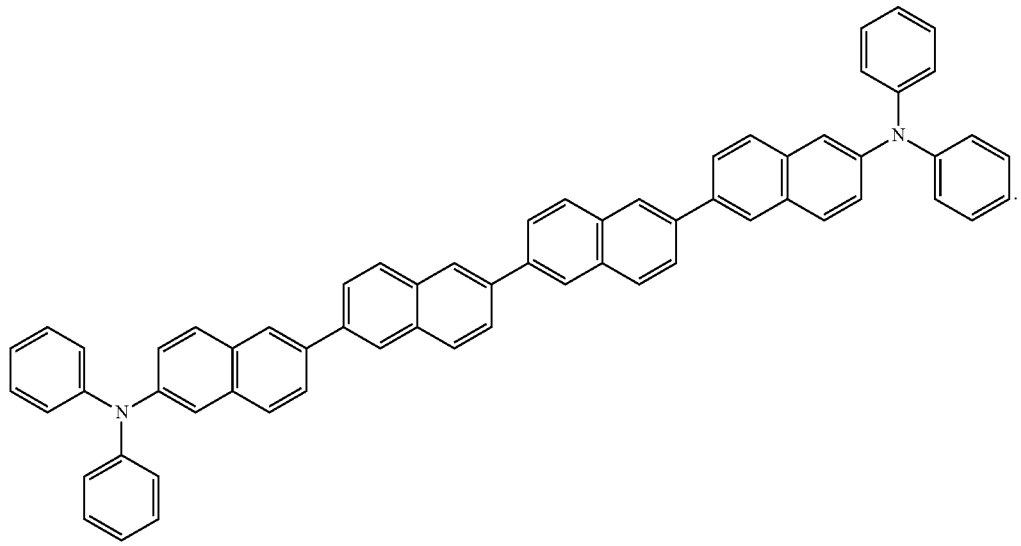

Fabrication and Evaluation of Organic Electroluminescent Element:

<Confirmation of Purity>

It was confirmed that all of the materials used in the fabrication of the organic electroluminescent element were subjected to sublimation purification, and the purity (absorption intensity area ratio at 254 nm) was confirmed to be 99.9% or more by using a high performance liquid chromatograph (TSKgel ODS-100Z, manufactured by Tosoh Corporation).

Example 1

Fabrication of Organic Electroluminescent Element by Means of Deposition

A 0.5 mm-thick and 2.5 cm square glass substrate (manufactured by Geomatec Co., Ltd., surface resistance: 10Ω/□) having an ITO film thereon was put in a cleaning container. After ultrasonic cleaning in 2-propanol, the glass substrate was subjected to a UV-ozone treatment for 30 minutes. The following organic compound layers were deposited sequentially on this transparent anode (ITO film) by a vacuum deposition method. Incidentally, the deposition rate in the following Examples and Comparative Examples is 0.1 nm/sec unless otherwise specifically indicated. The deposition rate was measured using a quartz oscillator. In addition, the thickness of each of the following layers was measured using a quartz oscillator.

First layer: HAT-CN: Film thickness: 10 nm
Second layer: HT-2: Film thickness: 30 nm
Third layer: H-1 and light emitting material (mass ratio: 93/7) shown in Table 1: Film thickness: 30 nm
Fourth layer: ET-1: Film thickness 30: nm HAT—CN represents the following structure.

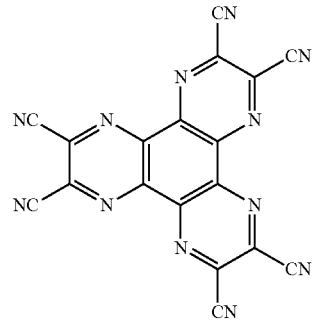

HT-2 represents the following structure.

HT-2

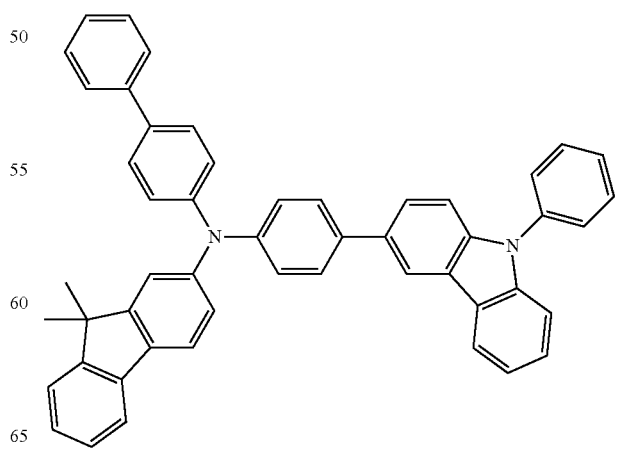

-continued

HT-1 represents the following structure.

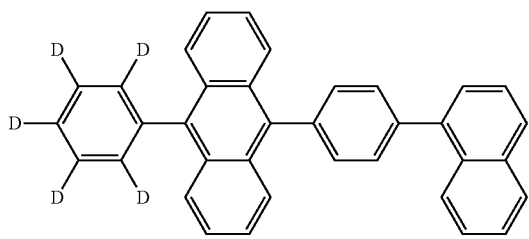
H-1

ET-1 represents the following structure.

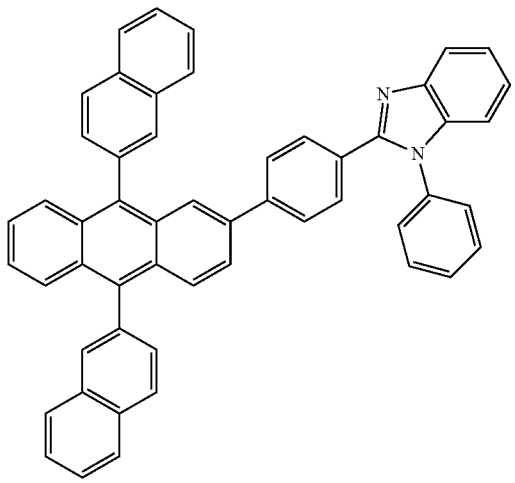
ET-1

1 nm of lithium fluoride and 100 nm of metallic aluminum were deposited in this order thereon, thereby forming a cathode. At that time, a patterned mask (mask having a light emitting area of 2 mm×2 mm) was placed on the layer of lithium fluoride, and the metallic aluminum was deposited.

The obtained laminate was put in a glove box purged with a nitrogen gas without bringing it into contact with the atmosphere and then sealed with a sealing can made of glass and an ultraviolet ray-curable adhesive (XNR5516HV, manufactured by Nagase-CIBA Ltd.), thereby obtaining Organic Electroluminescent Elements 1-1 to 1-15 and Comparative Organic Electroluminescent Elements 1-1 to 1-3 in a square shape having a light emitting area of 2 mm×2 mm. In all of the elements, light emission derived from the light emitting material was observed. As for the thus-obtained respective organic electroluminescent elements, the following tests were carried out.

<Evaluation of Element>

(a) External Quantum Efficiency:

A direct current voltage was applied to each of the elements by using a source measure unit 2400, manufactured by Keithley Instruments Inc. to allow the organic electroluminescent element to emit light. The luminance was measured by a luminance meter (BM-8, manufactured by Topcon Corporation). The luminous spectrum and the light emitting wavelength were measured by a spectrum analyzer PMA-11, manufactured by Hamamatsu Photonics K.K. On the basis of these values, the external quantum efficiency (i) at a luminance in the vicinity of 1,000 cd/m$^2$ was calculated by a luminance conversion method and expressed as a relative value, while taking the value of the organic electroluminescent element using the Comparative Material 1 as 1.0. The case where the relative external quantum efficiency is 1.0 or more is necessary from the standpoint of practical use, and the larger the numerical value than 1.0, the more favorable the efficiency is. Thus, such is preferable.

(b) Chromaticity:

The chromaticity (x, y) was determined from the luminous spectrum when light was emitted by applying a direct current voltage to each of the organic electroluminescent elements at a luminance of 1,000 cd/m$^2$. From the y values at that time, the chromaticity was evaluated according to the following 3 grades.

○: $0.04 \leq y \leq 0.12$
Δ: $0.03 \leq y < 0.04$, $0.09 < y \leq 0.12$
x: $y < 0.03$, $0.12 < y$ (c) Chromaticity after Driving Deterioration:

A direct voltage was applied to each of the organic electroluminescent elements to emit light continuously at a luminance of 1,000 cd/m$^2$. Then, the chromaticity (x', y') when the luminance was decreased to 500 cd/m$^2$ was determined as a luminous spectrum. The chromaticity change after driving deterioration was evaluated from a change in the y values $\Delta y$ $(=|y'-y|)$ before and after the driving deterioration according to the following three grades.

○: $\Delta y \leq 0.01$
Δ: $0.01 \leq \Delta y \leq 0.02$
x: $0.02 < \Delta y$

TABLE 2

| Element No. | Light emitting material | Relative external quantum efficiency | Chromaticity | Chromaticity after driving deterioration | Note |
|---|---|---|---|---|---|
| Element 1-1 | Compound 1 | 1.3 | ○ | ○ | The present invention |
| Element 1-2 | Compound 2 | 1.2 | ○ | ○ | The present invention |
| Element 1-3 | Compound 3 | 1.3 | ○ | ○ | The present invention |
| Element 1-4 | Compound 6 | 1.2 | ○ | ○ | The present invention |
| Element 1-5 | Compound 7 | 1.3 | ○ | ○ | The present invention |
| Element 1-6 | Compound 8 | 1.3 | Δ | ○ | The present invention |
| Element 1-7 | Compound 10 | 1.1 | ○ | ○ | The present invention |
| Element 1-8 | Compound 11 | 1.1 | Δ | ○ | The present invention |

TABLE 2-continued

| Element No. | Light emitting material | Relative external quantum efficiency | Chromaticity | Chromaticity after driving deterioration | Note |
|---|---|---|---|---|---|
| Element 1-9 | Compound 12 | 1.1 | Δ | ○ | The present invention |
| Element 1-10 | Compound 16 | 1.1 | Δ | ○ | The present invention |
| Element 1-11 | Compound 18 | 1.1 | ○ | ○ | The present invention |
| Element 1-12 | Compound 20 | 1.2 | Δ | ○ | The present invention |
| Element 1-13 | Compound 28 | 1.1 | Δ | ○ | The present invention |
| Element 1-14 | Compound 29 | 1.0 | ○ | ○ | The present invention |
| Element 1-15 | Compound 31 | 1.1 | Δ | ○ | The present invention |
| Comparative Element 1-1 | Comparative Material 1 | 1.0 | X | X | Comparative Example |
| Comparative Element 1-2 | Comparative Material 2 | 1.0 | X | X | Comparative Example |
| Comparative Element 1-3 | Comparative Material 3 | 0.9 | X | X | Comparative Example |

Example 2

Organic electroluminescent elements were fabricated in the same manner as that in Example 1, except that the layer configuration was changed to one shown below, and the evaluations were made in the same manners as those in Example 1. The results are shown in Table 3. Incidentally, the external quantum efficiency shown in Table 3 is shown as a relative value while taking the external quantum efficiency of the organic electroluminescent element using the Comparative Material 1 as 1.0.

First layer: HT-4: Film thickness: 50 nm

Second layer: HT-3: Film thickness: 45 nm

Third layer: H-2 and light emitting material (mass ratio: 95/5) shown in Table 1: Film thickness: 25 nm Fourth layer: ET-5: Film thickness: 5 nm Fifth layer: ET-3: Film thickness: 20 nm HT-4 represents the following structure.

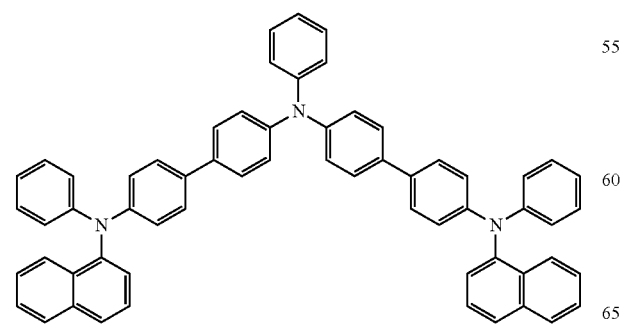

HT-4

HT-3 represents the following structure.

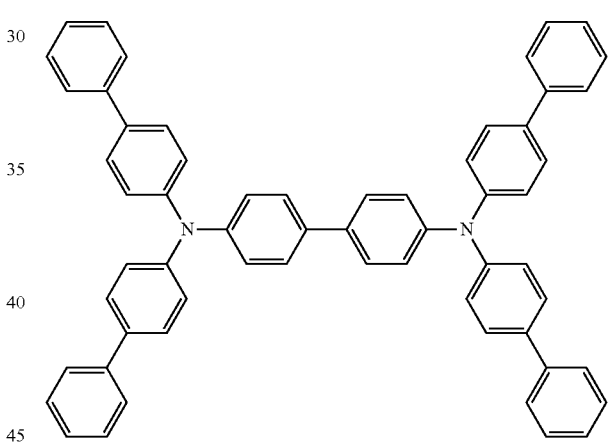

HT-3

HT-2 represents the following structure.

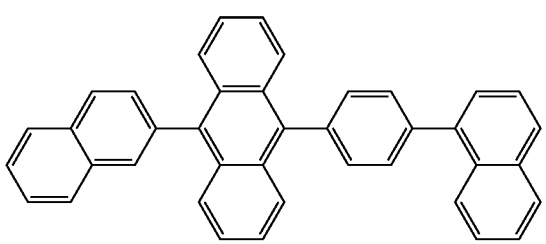

H-2

-continued

ET-5 represents the following structure.

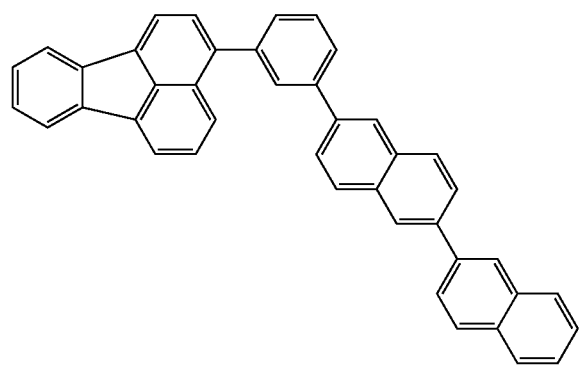

ET-5

-continued

ET-3 represents the following structure.

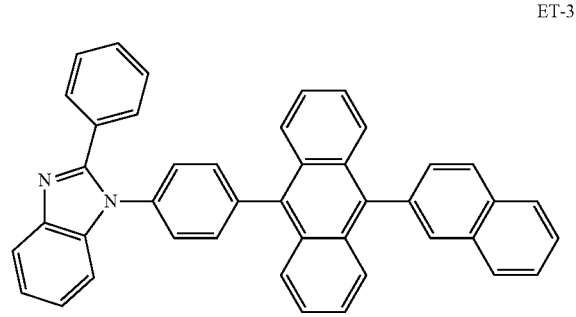

ET-3

TABLE 3

| Element No. | Light emitting material | Relative external quantum efficiency | Chromaticity | Chromaticity after driving deterioration | Note |
|---|---|---|---|---|---|
| Element 2-1 | Compound 1 | 1.4 | ○ | ○ | The present invention |
| Element 2-2 | Compound 2 | 1.3 | ○ | ○ | The present invention |
| Element 2-3 | Compound 3 | 1.3 | ○ | ○ | The present invention |
| Element 2-4 | Compound 6 | 1.2 | ○ | ○ | The present invention |
| Element 2-5 | Compound 7 | 1.4 | ○ | ○ | The present invention |
| Element 2-6 | Compound 8 | 1.2 | ○ | ○ | The present invention |
| Element 2-7 | Compound 10 | 1.1 | ○ | ○ | The present invention |
| Element 2-8 | Compound 11 | 1.4 | Δ | ○ | The present invention |
| Element 2-9 | Compound 12 | 1.3 | Δ | ○ | The present invention |
| Element 2-10 | Compound 16 | 1.3 | Δ | ○ | The present invention |
| Element 2-11 | Compound 18 | 1.1 | ○ | ○ | The present invention |
| Element 2-12 | Compound 20 | 1.2 | Δ | ○ | The present invention |
| Element 2-13 | Compound 28 | 1.2 | Δ | ○ | The present invention |
| Element 2-14 | Compound 29 | 1.1 | ○ | ○ | The present invention |
| Element 2-15 | Compound 31 | 1.2 | ○ | ○ | The present invention |
| Comparative Element 2-1 | Comparative Material 1 | 1.0 | X | Δ | Comparative Example |
| Comparative Element 2-2 | Comparative Material 2 | 0.9 | X | Δ | Comparative Example |
| Comparative Element 2-3 | Comparative Material 3 | 0.8 | X | Δ | Comparative Example |

Example 3

Organic electroluminescent elements were fabricated in the same manner as that in Example 1, except that the layer configuration was changed to one shown below, and the evaluations were made in the same manners as those in Example 1. The results are shown in Table 4. Incidentally, the external quantum efficiency shown in Table 4 is shown as a relative value while taking the external quantum efficiency of the organic electroluminescent element using the Comparative Material 1 as 1.0.

First layer: HAT-CN: Film thickness: 10 nm
Second layer: HT-2: Film thickness: 30 nm
Third layer: H-1 and light emitting material (mass ratio: 95/5) shown in Table 1: Film thickness: 30 nm
Fourth layer: ET-4: Film thickness: 30 nm
ET-4 represents the following structure.

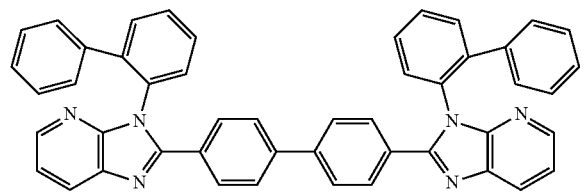

ET-4

Example 4

Organic electroluminescent elements were fabricated in the same manner as that in Example 1, except that the layer configuration was changed to one shown below, and the evaluations were made in the same manners as those in Example 1. The results are shown in Table 5. Incidentally, the external quantum efficiency shown in Table 5 is shown as a relative value while taking the external quantum efficiency of the organic electroluminescent element using the Comparative Material 1 as 1.0.

First layer: HAT-CN: Film thickness: 10 nm
Second layer: HT-1: Film thickness: 30 nm
Third layer: H-3 and light emitting material (mass ratio: 93/7) shown in Table 1: Film thickness: 30 nm
Fourth layer: ET-4: Film thickness: 30 nm

TABLE 4

| Element No. | Light emitting material | Relative external quantum efficiency | Chromaticity | Chromaticity after driving deterioration | Note |
|---|---|---|---|---|---|
| Element 3-1 | Compound 1 | 1.4 | ○ | ○ | The present invention |
| Element 3-2 | Compound 2 | 1.3 | ○ | ○ | The present invention |
| Element 3-3 | Compound 3 | 1.4 | ○ | ○ | The present invention |
| Element 3-4 | Compound 6 | 1.3 | ○ | ○ | The present invention |
| Element 3-5 | Compound 7 | 1.4 | ○ | ○ | The present invention |
| Element 3-6 | Compound 8 | 1.2 | ○ | ○ | The present invention |
| Element 3-7 | Compound 10 | 1.1 | ○ | ○ | The present invention |
| Element 3-8 | Compound 11 | 1.2 | Δ | ○ | The present invention |
| Element 3-9 | Compound 12 | 1.3 | Δ | ○ | The present invention |
| Element 3-10 | Compound 16 | 1.3 | Δ | ○ | The present invention |
| Element 3-11 | Compound 18 | 1.1 | ○ | ○ | The present invention |
| Element 3-12 | Compound 20 | 1.1 | Δ | ○ | The present invention |
| Element 3-13 | Compound 28 | 1.1 | Δ | ○ | The present invention |
| Element 3-14 | Compound 29 | 1.1 | ○ | ○ | The present invention |
| Element 3-15 | Compound 31 | 1.2 | ○ | ○ | The present invention |
| Comparative Element 3-1 | Comparative Material 1 | 1.0 | X | Δ | Comparative Example |
| Comparative Element 3-2 | Comparative Material 2 | 1.0 | X | Δ | Comparative Example |
| Comparative Element 3-3 | Comparative Material 3 | 0.9 | X | Δ | Comparative Example |

HT-1 represents the following structure.

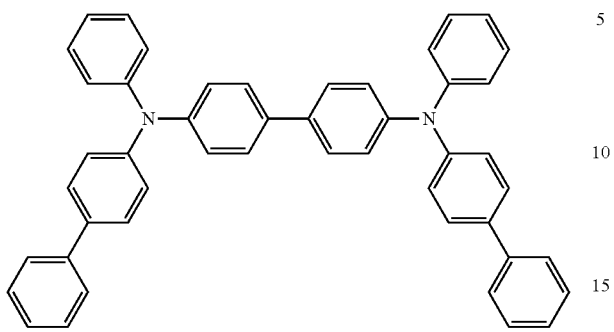

HT-1

HT-3 represents the following structure.

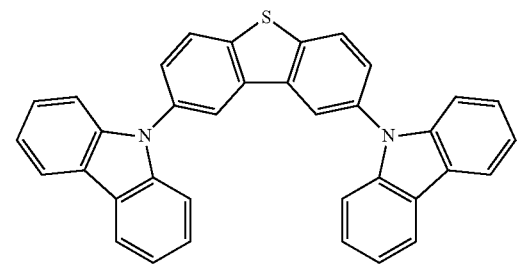

H-3

TABLE 5

| Element No. | Light emitting material | Relative external quantum efficiency | Chromaticity | Chromaticity after driving deterioration | Note |
|---|---|---|---|---|---|
| Element 4-1 | Compound 1 | 1.4 | ○ | ○ | The present invention |
| Element 4-2 | Compound 2 | 1.3 | ○ | ○ | The present invention |
| Element 4-3 | Compound 3 | 1.3 | ○ | ○ | The present invention |
| Element 4-4 | Compound 6 | 1.3 | ○ | ○ | The present invention |
| Element 4-5 | Compound 7 | 1.4 | ○ | ○ | The present invention |
| Element 4-6 | Compound 8 | 1.2 | ○ | ○ | The present invention |
| Element 4-7 | Compound 10 | 1.1 | ○ | ○ | The present invention |
| Element 4-8 | Compound 11 | 1.2 | Δ | ○ | The present invention |
| Element 4-9 | Compound 12 | 1.3 | Δ | ○ | The present invention |
| Element 4-10 | Compound 16 | 1.2 | Δ | ○ | The present invention |
| Element 4-11 | Compound 18 | 1.1 | ○ | ○ | The present invention |
| Element 4-12 | Compound 20 | 1.2 | Δ | ○ | The present invention |
| Element 4-13 | Compound 28 | 1.1 | Δ | ○ | The present invention |
| Element 4-14 | Compound 29 | 1.1 | ○ | ○ | The present invention |
| Element 4-15 | Compound 31 | 1.2 | ○ | ○ | The present invention |
| Comparative Element 4-1 | Comparative Material 1 | 1.0 | X | X | Comparative Example |
| Comparative Element 4-2 | Comparative Material 2 | 0.9 | X | X | Comparative Example |
| Comparative Element 4-3 | Comparative Material 3 | 0.9 | X | X | Comparative Example |

Example 5

Organic electroluminescent elements were fabricated in the same manner as that in Example 1, except that the layer configuration was changed to one shown below, and the evaluations were made in the same manners as those in Example 1. The results are shown in Table 6. Incidentally, the external quantum efficiency shown in Table 6 is shown as a relative value while taking the external quantum efficiency of the organic electroluminescent element using the Comparative Material 1 as 1.0.

First layer: HAT-CN: Film thickness: 10 nm
Second layer: HT-2: Film thickness: 30 nm
Third layer: H-4 and light emitting material (mass ratio: 93/7) shown in Table 1: Film thickness: 30 nm
Fourth layer: ET-2: Film thickness: 30 nm HT-4 represents the following structure.

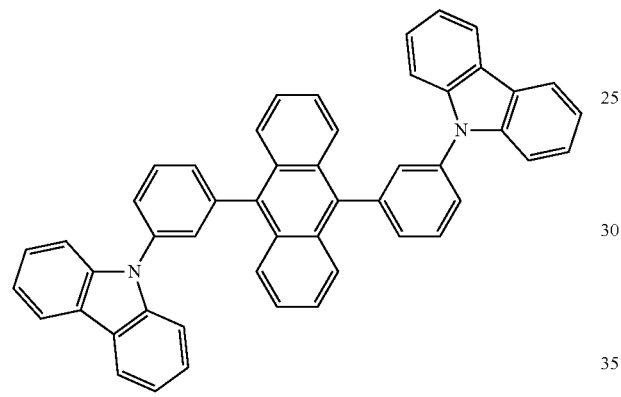

H-4

ET-2 represents the following structure.

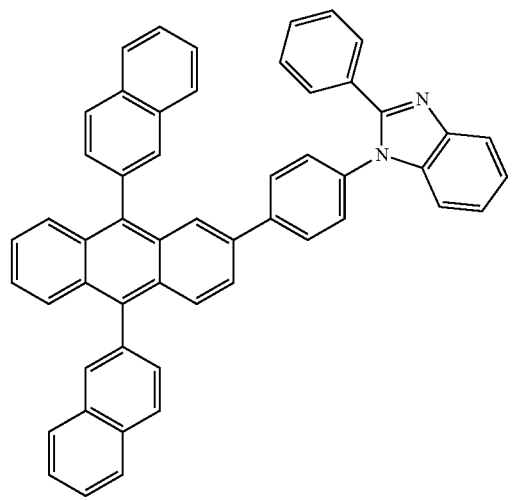

ET-2

TABLE 6

| Element No. | Light emitting material | Relative external quantum efficiency | Chromaticity | Chromaticity after driving deterioration | Note |
|---|---|---|---|---|---|
| Element 5-1 | Compound 1 | 1.3 | ○ | ○ | The present invention |
| Element 5-2 | Compound 2 | 1.3 | ○ | ○ | The present invention |
| Element 5-3 | Compound 3 | 1.3 | ○ | ○ | The present invention |
| Element 5-4 | Compound 6 | 1.2 | ○ | ○ | The present invention |
| Element 5-5 | Compound 7 | 1.3 | ○ | ○ | The present invention |
| Element 5-6 | Compound 8 | 1.3 | Δ | ○ | The present invention |
| Element 5-7 | Compound 10 | 1.1 | ○ | ○ | The present invention |
| Element 5-8 | Compound 11 | 1.2 | Δ | ○ | The present invention |
| Element 5-9 | Compound 12 | 1.3 | Δ | ○ | The present invention |
| Element 5-10 | Compound 16 | 1.3 | Δ | ○ | The present invention |
| Element 5-11 | Compound 18 | 1.2 | ○ | ○ | The present invention |
| Element 5-12 | Compound 20 | 1.2 | Δ | ○ | The present invention |
| Element 5-13 | Compound 28 | 1.1 | Δ | ○ | The present invention |
| Element 5-14 | Compound 29 | 1.1 | Δ | ○ | The present invention |

TABLE 6-continued

| Element No. | Light emitting material | Relative external quantum efficiency | Chromaticity | Chromaticity after driving deterioration | Note |
|---|---|---|---|---|---|
| Element 5-15 | Compound 31 | 1.1 | ○ | ○ | The present invention |
| Comparative Element 5-1 | Comparative Material 1 | 1.0 | X | Δ | Comparative Example |
| Comparative Element 5-2 | Comparative Material 2 | 1.0 | X | Δ | Comparative Example |
| Comparative Element 5-3 | Comparative Material 3 | 0.9 | X | Δ | Comparative Example |

Example 6

Evaluation of Organic Electroluminescent Element (Coating)

—Preparation of Coating Solution for Forming Light Emitting Layer—

Compound 4 (0.05% by mass) and Host Material PH-1 (0.95% by mass) were mixed with methyl ethyl ketone (99.0% by mass) to obtain Coating Solution 1 for forming a light emitting layer.

Coating Solutions 2 and 3 for forming a light emitting layer were prepared in the same manner as that in the preparation of the Coating Solution 1 for forming a light emitting layer, except that the Compound 4 was changed to Compounds 10 and 24, respectively.

In addition, Coating Solutions 4 to 6 for forming a light emitting layer were prepared in the same manners as those in the preparation of the Coating Solutions 1 to 3 for forming a light emitting layer, except that in the Coating Solutions 1 to 3 for forming a light emitting layer, the Host Material PH-1 was changed to Host Material H-2.

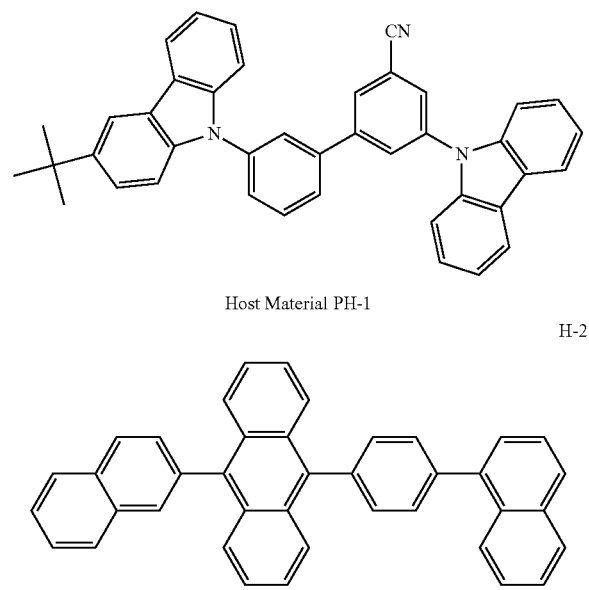

Host Material PH-1

H-2

In addition, as comparative examples, Comparative Coating Solutions 1 and 2 for forming a light emitting layer were prepared in the same manners as those in the preparation of the Coating Solutions 1 and 4 for forming a light emitting layer, except that in the Coating Solutions 1 and 4 for a light emitting layer, the Compound 4 was changed to Comparative Material 1.

(Procedures of Element Fabrication)

—Fabrication of Organic Electroluminescent Element—

ITO was deposited in a thickness of 150 nm on a glass substrate at 25 mm×25 mm×0.7 mm, thereby forming a film. The film was taken as a transparent supporting substrate. This transparent supporting substrate was etched and washed.

On this ITO glass substrate, 2 parts by mass of PTPDES-2 represented by the following structural formula (manufactured by Chemipro Kasei Kaisha, Ltd., Tg=205° C.) was dissolved in 98 parts by mass of cyclohexanone for the electronics industry use (manufactured by Kanto Chemical Co., Inc.) and spin coated in a thickness of about 40 nm (at 2,000 rpm for 20 seconds). Thereafter, the coated ITO glass substrate was dried at 120° C. for 30 minutes and subjected to an annealing treatment at 160° C. for 10 minutes, thereby forming a hole injecting layer.

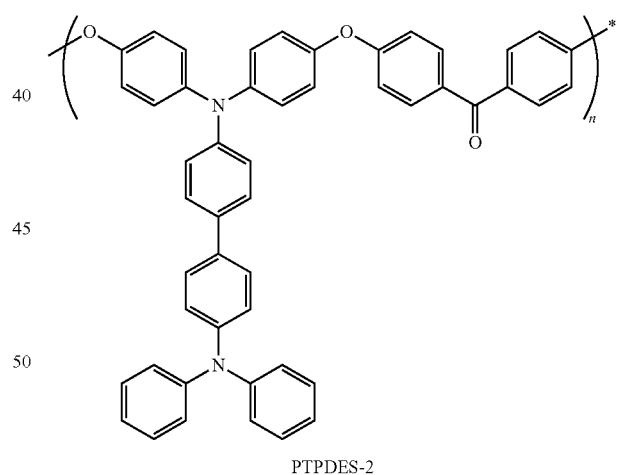

PTPDES-2

The Coating Solution 1 for forming a light emitting layer was spin coated in a thickness of about 40 nm on this hole injecting layer (at 1,300 rpm, 30 seconds), thereby obtaining a light emitting layer.

Subsequently, BAlq (bis-(2-methyl-8-quinolato)-4-(phenyl-phenolate)-aluminum (III)) represented by the following structural formula was formed in a thickness of 40 nm as an electron transporting layer on the light emitting layer by a vacuum deposition method.

Lithium fluoride (LiF) was formed in a thickness of 1 nm as an electron injecting layer on the electron transporting layer by a vacuum deposition method. Metallic aluminum was further deposited in a thickness of 70 nm thereon, thereby forming a cathode.

The thus-fabricated laminate was put in a globe box purged with an argon gas and then sealed with a sealing can made of stainless steel and an ultraviolet ray-curable adhesive (XNR5516HV, manufactured by Nagase-CIBA Ltd.), thereby fabricating Organic Electroluminescent Element P1.

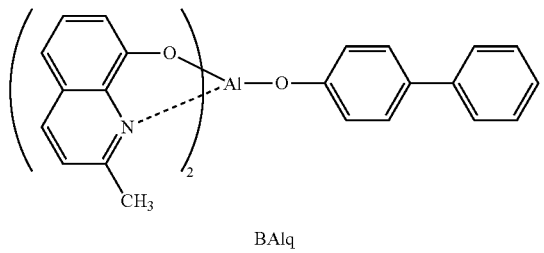

BAlq

Organic Electroluminescent Elements P2 to P6 were fabricated in the same manner as that in the fabrication of the Organic Electroluminescent Element P1, except that in the Organic Electroluminescent Element P1, the Coating Solution 1 for forming a light emitting layer was changed to the Coating Solutions 2 to 6 for forming a light emitting layer, respectively.

In addition, as comparative examples, Organic Electroluminescent Elements P7 and P8 were fabricated in the same manners as those in the preparation of the Organic Electroluminescent Elements P1 and P4, except that in the Organic Electroluminescent Elements P1 and P4, the Coating Solutions 1 and 4 for forming a light emitting layer were changed to the Comparative Coating Solutions 1 and 2 for forming a light emitting layer, respectively.

The evaluations were made in the same manners as those in Example 1. The results are shown in Table 7. Incidentally, the external quantum efficiency shown in Table 7 is shown as a relative value while taking the external quantum efficiency of the organic electroluminescent element using the Comparative Material 1 as 1.0.

It is noted from the above-described Tables 2 to 7 that the organic electroluminescent element according to the present invention is capable of realizing a high blue color purity, improving the durability, enhancing the luminous efficiency, and reducing the chromaticity change during driving of the organic electroluminescent element.

The invention claimed is:

1. An organic electroluminescent element comprising:
a substrate;
a pair of electrodes including an anode and a cathode, disposed on the substrate; and
at least one organic layer including a light emitting layer, disposed between the electrodes,
wherein the organic layer includes a compound represented by the following General Formula (2), General Formula (2)

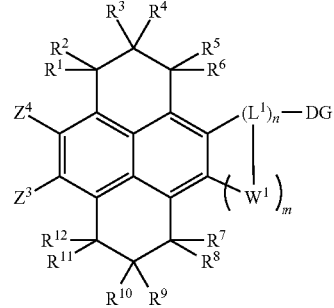

wherein, in General Formula (2), $R^1$ to $R^{12}$ each independently represents a hydrogen atom or a substituent and which may be bound to each other to form a non-aromatic ring,
wherein $L^1$ represents a divalent or higher linking group, $W^1$ represents O, S, $CY^8Y^9$ or $NY^6$ where $Y^6$, $Y^8$ and $Y^9$ each independently represent an alkyl group, a silyl group, an aryl group or a heteroaryl group, and which may further have substituents,
wherein $Z^3$ and $Z^4$ each independently represent a hydrogen atom or a substituent,
wherein $L^1$ and $W^1$, and $Z^3$ and $Z^4$ may be bound to each other to form a ring,
wherein DG represents a donor group,

TABLE 7

| Organic electroluminescent element | Light emitting layer | Host material | Relative external quantum efficiency | Chromaticity | Chromaticity change after driving deterioration | Note |
|---|---|---|---|---|---|---|
| P1 | Compound 4 | PH-1 | 1.2 | ○ | ○ | The present invention |
| P2 | Compound 10 | PH-1 | 1.2 | ○ | ○ | The present invention |
| P3 | Compound 24 | PH-1 | 1.3 | ○ | ○ | The present invention |
| P7 | Comparative Material 1 | PH-1 | 1.0 | X | X | Comparative Example |
| P4 | Compound 4 | H-2 | 1.3 | ○ | ○ | The present invention |
| P5 | Compound 10 | H-2 | 1.1 | ○ | ○ | The present invention |
| P6 | Compound 24 | H-2 | 1.2 | ○ | ○ | The present invention |
| P8 | Comparative Material 1 | H-2 | 1.0 | X | X | Comparative Example | wherein n represents an integer of 1 or 2, wherein m represents 0 or 1 such that when m is 0, $L^1$ and $W^1$ are not bound to each other.

2. The organic electroluminescent element according to claim 1, wherein the compound represented by the General Formula (2) is a compound represented by the following General Formula (3), General Formula (3)

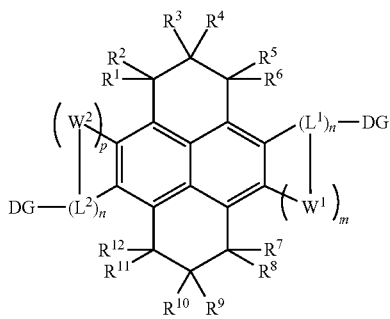

wherein, in General Formula (3), $R^1$ to $R^{12}$ each independently represents a hydrogen atom or a substituent which may be bound to each other to form a non-aromatic ring, wherein $L^1$ and $L^2$ each independently represents a divalent or higher linking group, wherein $W^1$ and $W^2$ each independently represents O, S, $CY^8Y^9$ or $NY^6$ where $Y^6$, $Y^8$ and $Y^9$ each independently represents an alkyl group, a silyl group, an aryl group or a heteroaryl group, and which may further have substituents, wherein $L^1$ and $W^1$, and $L^2$ and $W^2$ may be bound to each other to form a ring, wherein DG represents a donor group, wherein n represents an integer of 1 or 2, and wherein m and p represent an integer of 0 or 1 such that when m or p is 0, $L^1$ and $W^1$, and $L^2$ and $W^2$ are not bonded to each other.

3. The organic electroluminescent element according to claim 1, wherein, in the General Formula (2), the donor group represents $-NY^1Y^2$, $-OY^3$ or $SY^4$ where $Y^1$ to $Y^4$ each independently represents an alkyl group, an aryl group or a heteroaryl group, and which may further have substituents, or the donor group is represented by the following General Formula (A)

General Formula (A)

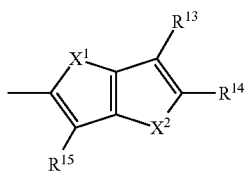

wherein, in General Formula (A), $X^1$ and $X^2$ each independently represents O, S or $NY^5$, $R^{13}$ to $R^{15}$ each independently represents a hydrogen atom, an alkyl group, a silyl group, an aryl group, a heteroaryl group, $-NY^1Y^2$, $-OY^3$ or $-SY^4$ where $Y^1$ to $Y^5$ each independently represents an alkyl group, an aryl group or a heteroaryl group, and which may further have substituents.

4. The organic electroluminescent element according to claim 2, wherein in the General Formula (3) L1 and L2 each independently represents an arylene group or a heteroarylene group.

5. The organic electroluminescent element according to claim 2, wherein in the General Formula (3) $L^1$ and $L^2$ are each independently represented by any one of the following General Formulae (4) to (7) where a substituent with a Hammett substituent constant $\sigma_p$ value of 0.1 or more is not included in the linking groups represented by the Formulae (4) to (7), General Formula (4)

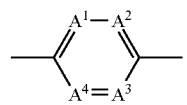

wherein, in General Formula (4), $A^1$ to $A^4$ each independently represents $CY^7$ or N and may be condensed in $A^1$ and A and form an aromatic ring, $Y^7$ represents a hydrogen atom, an alkyl group, an aryl group or a heteroaryl group, and which may further have substituents, $W^1$ is bound to $A^4$ when m in the General Formula (2) is 1, and $W^1$ and $W^2$ are bound to $A^4$ when m and p in the General Formula (3) each independently represents 1, General Formula (5)

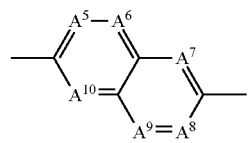

wherein, in General Formula (5), $A^5$ to $A^{10}$ each independently represents $CY^7$ or N, $Y^7$ represents a hydrogen atom, an alkyl group, an aryl group or a heteroaryl group, and which may further have substituents, $W^1$ is bound to $A^5$ or $A^{10}$ when m in the General Formula (2) is 1, and $W^1$ and W are bound to $A^5$ or $A^{10}$ when m and p in the General Formula (3) each independently represents 1, General Formula (6)

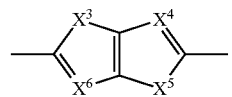

wherein, in General Formula (6), $X^3$ and $X^5$ each independently represents O, S or $NY^6$, $X^4$ and $X^6$ each independently represents $CY^7$ or N, $Y^6$ and $Y^7$ each independently represents a hydrogen atom, an alkyl group, an aryl group or a heteroaryl group, and which may further have substituents, and m and p in the General Formulae (2) or (3) are 0, General Formula (7)

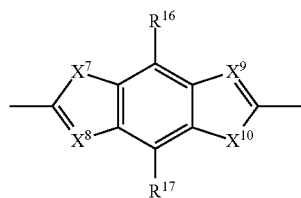

wherein, in General Formula (7), $X^7$ and $X^{10}$ each independently represents O, S or $NY^6$, $X^8$ and $X^9$ each independently represents $CY^7$ or N, $Y^6$ and $Y^7$ each independently represents a hydrogen atom, an alkyl group, an aryl group or a heteroaryl group, and which may further have substituents, $R^{16}$ and $R^{17}$ each independently represents a hydrogen atom, a fluorine atom, an alkyl group, a silyl group, an aryl group, a heteroaryl group, $-NY^1Y^2$, $-OY^3$ or $-SY^4$ where $Y^1$ to $Y^4$ each independently represent an alkyl group, an aryl group or a heteroaryl group, and which may further have substituents, and m and p in the General Formula (2) or (3) are 0.

6. The organic electroluminescent element according to claim 1, wherein the compound represented by the General Formula (2) is a compound represented by any one of the following General Formulae (8) to (11), General Formula (8)

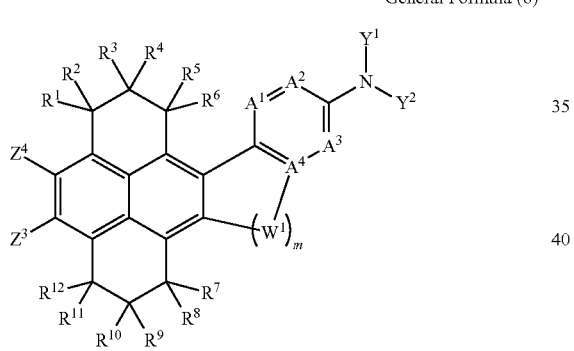

wherein, in General Formula (8), $R^1$ to $R^{12}$ each independently represents a hydrogen atom or a substituent and which may be bound to each other to form a non-aromatic ring, $A^1$ to $A^4$ each independently represent $CY^7$ or N and may be condensed in $A^1$ and $A^2$ and form an aromatic ring, $Y^7$ represents a hydrogen atom, an alkyl group, an aryl group or a heteroaryl group, and which may further have substituents, $Y^1$ and $Y^2$ each independently represents an alkyl group, an aryl group or a heteroaryl group, and which may further have substituents and may be bound to each other to form a ring, $W^1$ represents O, S, $CY^8Y^9$ or $NY^6$ where $Y^6$, $Y^8$ and $Y^9$ each independently represents an alkyl group, a silyl group, an aryl group or a heteroaryl group, and which may further have substituents, $Z^3$ and $Z^4$ each independently represents a hydrogen atom or a substituent, $A^4$ and $W^1$, and $Z^3$ and $Z^4$ may be bound to each other to form a ring, and m represents 0 or 1 where $A^4$ and $W^1$ are not bound to each other when m is 0, General Formula (9)

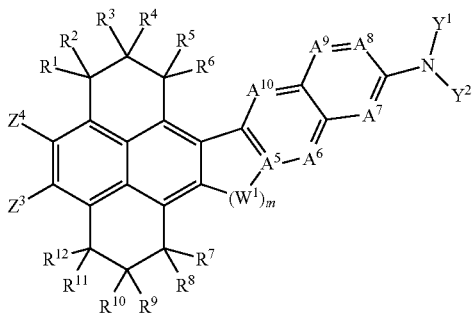

wherein, in General Formula (10), $R^1$ to $R^{12}$ each independently represents a hydrogen atom or a substituent and which may be bound to each other to form a non-aromatic ring, $X^3$ and $X^5$ each independently represents O, S or $NY^6$, $X^4$ and $X^6$ each independently represents $CY^7$ or N, $Y^6$ and $Y^7$ each independently represents a hydrogen atom, an alkyl group, an aryl group or a heteroaryl group, and which may further have substituents, $Y^1$ and $Y^2$ each independently represent an alkyl group, an aryl group or a heteroaryl group, and which may further have substituents and may be bound to each other to form a ring, $Z^2$ to $Z^4$ each independently represent a hydrogen atom or a substituent, and $Z^3$ and $Z^4$ may be bound to each other to form a ring, General Formula (11)

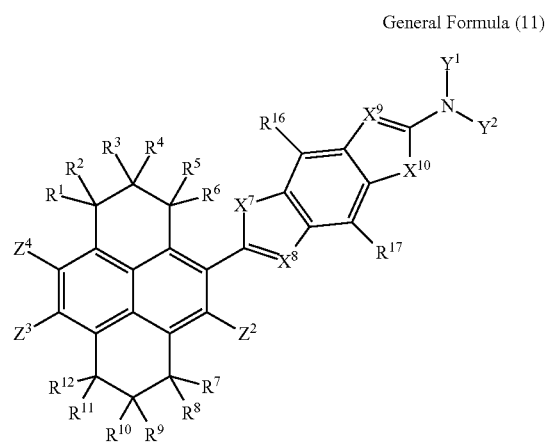

wherein, in General Formula (11), $R^1$ to $R^{12}$ each independently represents a hydrogen atom or a substituent and which may be bound to each other to form a non-aromatic ring, $X^7$ and $X^{10}$ each independently represents O, S or $NY^6$, $X^8$ and $X^9$ each independently represents $CY^7$ or N, $Y^6$ and $Y^7$ each independently represents a hydrogen atom, an alkyl group, an aryl group or a heteroaryl group, and which may further have substituents, $R^{16}$ and $R^{17}$ each independently represents a hydrogen atom, a fluorine atom, an alkyl group, a silyl group, an aryl group, a heteroaryl group, $-NY^1Y^2$, $-OY^3$ or $-SY^4$ where $Y^1$ to $Y^4$ each independently represent an alkyl group, an aryl group or a heteroaryl group, and which may further have substituents, $Y^1$ and $Y^2$ each independently represent an alkyl group, an aryl group or a heteroaryl group, and which may further have substituents and may be bound to each other to form a ring, $Z^2$ to $Z^4$ each independently represents a hydrogen atom or a substituent, and $Z^3$ and $Z^4$ may be bound to each other to form a ring.

7. The organic electroluminescent element according to claim 6, wherein the compound represented by the General Formula (8) is a compound represented by the following General Formula (12)

General Formula (12)

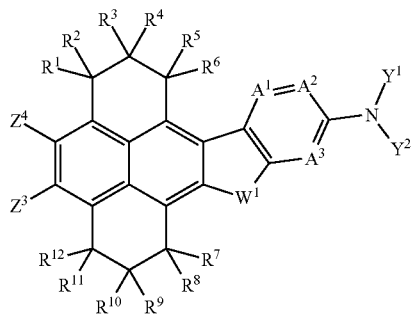

wherein, in General Formula (12), $R^1$ to $R^{12}$ each independently represents a hydrogen atom or a substituent and which may be bound to each other to form a non-aromatic ring, $A^1$ to $A^4$ each independently represents $CY^7$ or N, may be condensed in $A^1$ and $A^2$ and form an aromatic ring, $Y^7$ represents a hydrogen atom, an alkyl group, an aryl group or a heteroaryl group, and which may further have substituents, $Y^1$ and $Y^2$ each independently represents an alkyl group, an aryl group or a heteroaryl group, and which may further have substituents and may be bound to each other to form a ring, $W^1$ represents O, S, $CY^8Y^9$ or $NY^6$ where $Y^6$, $Y^8$ and $Y^9$ each independently represents an alkyl group, a silyl group, an aryl group or a heteroaryl group, and which may further have substituents, $Z^3$ and $Z^4$ each independently represents a hydrogen atom or a substituent, and $Z^3$ and $Z^4$ may be bound to each other to form a ring.

8. The organic electroluminescent element according to claim 6, wherein the compound represented by the General Formula (9) is a compound represented by the following General Formula (13), General Formula (13)

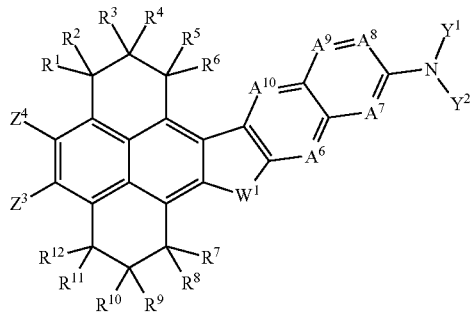

wherein, in General Formula (13), $R^1$ to $R^{12}$ each independently represents a hydrogen atom or a substituent and which may be bound to each other to form a non-aromatic ring, $A^5$ to $A^{10}$ each independently represents $CY^7$ or N, $Y^7$ represents a hydrogen atom, an alkyl group, an aryl group or a heteroaryl group, and which may further have substituents, $Y^1$ and $Y^2$ each independently represents an alkyl group, an aryl group or a heteroaryl group, and which may further have substituents and may be bound to each other to form a ring, $W^1$ represents O, S, $CY^8Y^9$ or $NY^6$ where $Y^6$, $Y^8$ and $Y^9$ each independently represents an alkyl group, a silyl group, an aryl group or a heteroaryl group, and which may further have substituents, $Z^3$ and $Z^4$ each independently represent a hydrogen atom or a substituent, and $Z^3$ and $Z^4$ may be bound to each other to form a ring.

9. The organic electroluminescent element according to claim 1, wherein the compound represented by the General Formula (2) is a compound represented by any one of the following General Formulae (8') to (11'), General Formula (8')

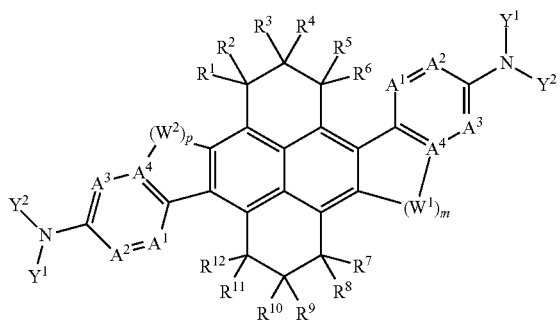

wherein, in General Formula (8'), $R^1$ to $R^{12}$ each independently represents a hydrogen atom or a substituent and which may be bound to each other to form a non-aromatic ring, $A^1$ to $A^4$ each independently represents $CY^7$ or N, may be condensed in $A^1$ and $A^2$ and form an aromatic ring, $Y^7$ represents a hydrogen atom, an alkyl group, an aryl group or a heteroaryl group, and which may further have substituents, $Y^1$ and $Y^2$ each independently represent an alkyl group, an aryl group or a heteroaryl group, and which may further have substituents and may be bound to each other to form a ring, $W^1$ and $W^2$ each independently represents O, S, $CY^8Y^9$ or $NY^6$ where $Y^6$, $Y^8$ and $Y^9$ each independently represent an alkyl group, a silyl group, an aryl group or a heteroaryl group, and which may further have substituents, m represents 0 or 1 where $A^4$ and $W^1$ are not bound to each other when m is 0, p represents 0 or 1 where $A^4$ and $W^2$ are not bound to each other when p is 0, General Formula (9')

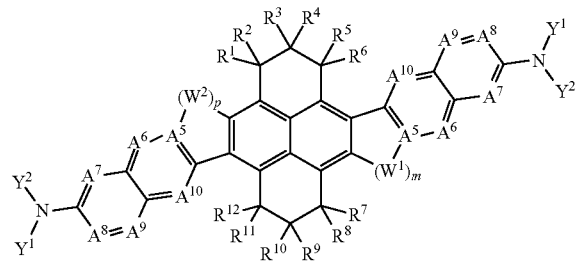

wherein, in General Formula (9'), $R^1$ to $R^{12}$ each independently represents a hydrogen atom or a substituent and which may be bound to each other to form a non-aromatic ring, $A^5$ to $A^{10}$ each independently represents $CY^7$ or N, $Y^7$ represents a hydrogen atom, an alkyl group, an aryl group or a heteroaryl group, and which may further have substituents, $Y^1$ and $Y^2$ each independently represents an alkyl group, an aryl group or a heteroaryl group, and which may further have substituents and may be bound to each other to form a ring, $W^1$ and $W^2$ each independently represents O, S, $CY^8Y^9$ or $NY^6$ where $Y^6$, $Y^8$ and $Y^9$ each independently represent an alkyl group, a silyl group, an aryl group or a heteroaryl group, and which may further have substituents, m represents 0 or 1 where $A^5$ and $W^1$ are not bound to each other when m is 0, p represents 0 or 1 where $A^5$ and $W^2$ are not bound to each other when p is 0, General Formula (10')

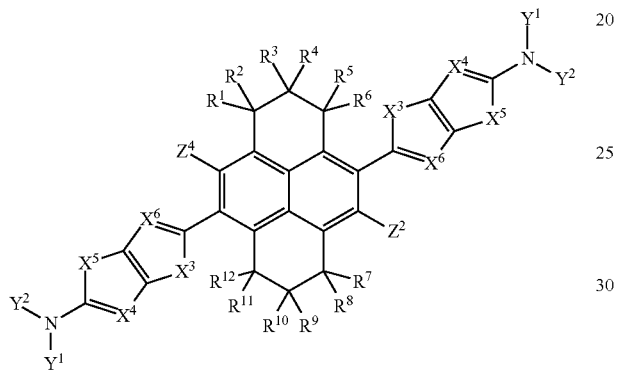

wherein, in General Formula (10'), $R^1$ to $R^{12}$ each independently represents a hydrogen atom or a substituent and which may be bound to each other to form a non-aromatic ring, $X^3$ and $X^5$ each independently represents O, S or $NY^6$, $X^4$ and $X^6$ each independently represents $CY^7$ or N, $Y^6$ and $Y^7$ each independently represent a hydrogen atom, an alkyl group, an aryl group or a heteroaryl group, and which may further have substituents, $Y^1$ and $Y^2$ each independently represent an alkyl group, an aryl group or a heteroaryl group, and which may further have substituents and may be bound to each other to form a ring, and $Z^2$ and $Z^4$ each independently represents a hydrogen atom or a substituent, General Formula (11')

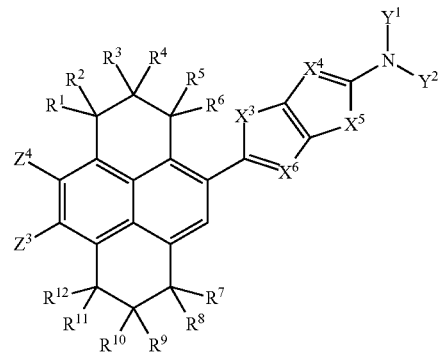

wherein, in General Formula (9), $R^1$ to $R^{12}$ each independently represents a hydrogen atom or a substituent and which may be bound to each other to form a non-aromatic ring, $A^5$ to $A^{10}$ each independently represents $CY^7$ or N, $Y^7$ represents a hydrogen atom, an alkyl group, an aryl group or a heteroaryl group, and which may further have substituents, $Y^1$ and $Y^2$ each independently represents an alkyl group, an aryl group or a heteroaryl group, and which may further have substituents and may be bound to each other to form a ring, $W^1$ represents O, S, $CY^8Y^9$ or $NY^6$ where $Y^6$, $Y^8$ and $Y^9$ each independently represents an alkyl group, a silyl group, an aryl group or a heteroaryl group, and which may further have substituents, $Z^3$ and $Z^4$ each independently represents a hydrogen atom or a substituent, $A^5$ and $W^1$, and $Z^3$ and $Z^4$ may be bound to each other to form a ring, m represents 0 or 1 where $A^5$ and $W^1$ are not bound to each other when m is 0, General Formula (10)

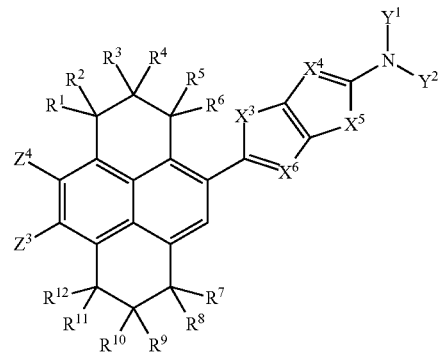

wherein, in General Formula (11'), $R^1$ to $R^{19}$ each independently represents a hydrogen atom or a substituent and which may be bound to each other to form a non-aromatic ring, $X^7$ and $X^{10}$ each independently represents O, S or $NY^6$, $X^8$ and $X^9$ each independently represents $CY^7$ or N, $Y^6$ and $Y^7$ each independently represents a hydrogen atom, an alkyl group, an aryl group or a heteroaryl group, and which may further have substituents, $R^{16}$ and $R^{17}$ each independently represents a hydrogen atom, a fluorine atom, an alkyl group, a silyl group, an aryl group, a heteroaryl group, $—NY^1Y^2$, $—OY^3$ or $—SY^4$ where $Y^1$ to $Y^4$ each independently represents an alkyl group, an aryl group or a heteroaryl group, and which may further have substituents, $Y^1$ to $Y^2$ each independently represents an alkyl group, an aryl group or a heteroaryl group, and which may further have substituents and may be bound to each other to form a ring, and $Z^2$ and $Z^4$ each independently represents a hydrogen atom or a substituent.

10. The organic electroluminescent element according to claim 9, wherein the compound represented by the General Formula (8') is a compound represented by the following General Formula (14), General Formula (14)

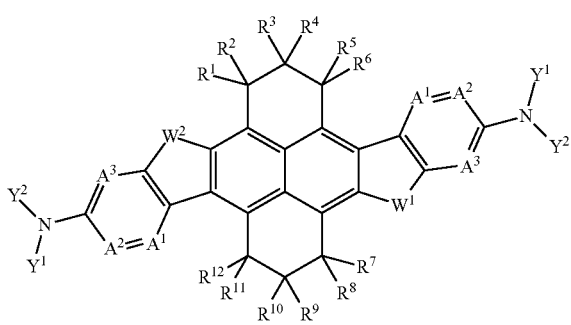

wherein, in General Formula (14), $R^1$ to $R^{12}$ each independently represents a hydrogen atom or a substituent and which may be bound to each other to form a non-aromatic ring, $A^1$ to $A^3$ each independently represents $CY^7$ or N, may be condensed in $A^1$ and $A^2$ and form an aromatic ring, $Y^7$ represents a hydrogen atom, an alkyl group, an aryl group or a heteroaryl group, and which may further have substituents, $Y^1$ and $Y^2$ each independently represent an alkyl group, an aryl group or a heteroaryl group, and which may further have substituents and may be bound to each other to form a ring, $W^1$ and $W^2$ each independently represents O, S, $CY^8Y^9$ or $NY^6$ where $Y^6$, $Y^8$ and $Y^9$ each independently represents an alkyl group, a silyl group, an aryl group or a heteroaryl group, and which may further have substituents.

11. The organic electroluminescent element according to claim 9, wherein the compound represented by the General Formula (9') is a compound represented by the following General Formula (15), General Formula (15)

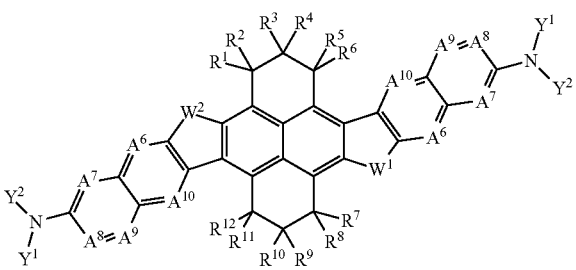

wherein, in General Formula (15), $R^1$ to $R^{12}$ each independently represents a hydrogen atom or a substituent and which may be bound to each other to form a non-aromatic ring, $A^5$ to $A^{10}$ each independently represents $CY^7$ or N, $Y^7$ represents a hydrogen atom, an alkyl group, an aryl group or a heteroaryl group, and which may further have substituents, $Y^1$ and $Y^2$ each independently represents an alkyl group, an aryl group or a heteroaryl group, and which may further have substituents and may be bound to each other to form a ring, and $W^1$ and $W^2$ each independently represents O, S, $CY^8Y^9$ or $NY^6$ where $Y^6$, $Y^8$ and $Y^9$ each independently represents an alkyl group, a silyl group, an aryl group or a heteroaryl group, and which may further have substituents.

12. The organic electroluminescent element according to claim 1, wherein the light emitting layer includes an anthracene-based host material.

13. The organic electroluminescent element according to claim 1, wherein the light emitting layer is formed by a vacuum deposition process.

14. The organic electroluminescent element according to claim 1, wherein the light emitting layer is formed by a wet process.

15. A light emitting device comprising the organic electroluminescent element according to claim 1.

16. A display device comprising the organic electroluminescent element according to claim 1.

17. An illumination device comprising the organic electroluminescent element according to claim 1.

18. A material for an organic electroluminescent element represented by the following General Formula (2), General Formula (2)

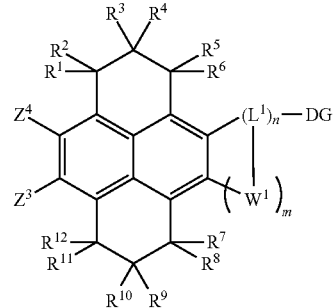

wherein, in General Formula (2), $R^1$ to $R^{12}$ each independently represents a hydrogen atom or a substituent and which may be bound to each other to form a non-aromatic ring, wherein $L^1$ represents a divalent or higher linking group, $W^1$ represents O, S, $CY^8Y^9$ or $NY^6$ where $Y^6$, $Y^8$ and $Y^9$ each independently represent an alkyl group, a silyl group, an aryl group or a heteroaryl group, and which may further have substituents, wherein $Z^3$ and $Z^4$ each independently represent a hydrogen atom or a substituent, wherein $L^1$ and $W^1$, and $Z^3$ and $Z^4$ may be bound to each other to form a ring, wherein DG represents a donor group, wherein n represents an integer of 1 or 2, wherein m represents 0 or 1 such that when m is 0, $L^1$ and $W^1$ are not bound to each other.

* * * * *